(12) United States Patent
Honda et al.

(10) Patent No.: US 8,105,230 B2
(45) Date of Patent: Jan. 31, 2012

(54) MEDICAL SYSTEM

(75) Inventors: Kazuki Honda, Hachioji (JP); Yasuhito Kura, Hachioji (JP); Takaaki Komiya, Akiruno (JP); Kazushi Murakami, Hino (JP); Hiroaki Ichikawa, Hachioji (JP); Tsutomu Okada, Tachikawa (JP); Yoshio Onuki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 920 days.

(21) Appl. No.: 11/825,742

(22) Filed: Jul. 9, 2007

(65) Prior Publication Data

US 2009/0018390 A1 Jan. 15, 2009

(51) Int. Cl.
*A61B 1/00* (2006.01)
(52) U.S. Cl. ........................................ 600/106; 600/104
(58) Field of Classification Search .................. 600/104, 600/106, 107, 114–118; 606/205–209, 95.01
See application file for complete search history.

(56) References Cited

U.S. PATENT DOCUMENTS
2005/0159644 A1* 7/2005 Takano .................. 600/115

FOREIGN PATENT DOCUMENTS
| JP | 57-190541 | 11/1982 |
| JP | 2000-000207 | 1/2000 |
| JP | 2007-117394 | 5/2007 |

* cited by examiner

*Primary Examiner* — Matthew J Kasztejna
*Assistant Examiner* — Ryan Henderson
(74) *Attorney, Agent, or Firm* — Scully, Scott, Murphy & Presser, P.C.

(57) ABSTRACT

A medical system according to the present invention includes: a medical instrument provided with a treatment portion for performing treatment operations on living body tissue; a treatment portion displacement mechanism for displacing the position of the treatment portion of the medical instrument; a treatment detection portion that detects whether the treatment portion is in a treatment state or a non-treatment state; and a control portion that controls displacement of the treatment portion by controlling the treatment portion displacement mechanism according to detection results from the treatment detection portion.

13 Claims, 29 Drawing Sheets

FIG.6

MEDICAL SYSTEM

BACKGROUND OF THE INVENTION

1. Field of the Invention

The present invention relates to a medical system provided with a treatment instrument that performs treatment on living body tissue, and more particularly, to a medical system provided with an endoscope to be inserted into a body cavity and various treatment instruments to be used in combination with the endoscope.

2. Description of the Related Art

As is generally known, endoscopes are widely used in the industrial field and the field of medicine. With endoscopes that are medical apparatuses used in the field of medicine, observations are made by inserting an insertion portion into a body cavity of a subject being tested.

In addition, with such an endoscope, various treatments may be performed by introducing treatment instruments via a treatment instrument insertion channel provided to the insertion portion. When performing treatment on a body cavity tissue using a treatment instrument, the operator introduces the treatment instrument into the body cavity via a treatment instrument insertion channel of the endoscope.

Normally, the treatment instrument is manually inserted into and pulled out by the operator from the treatment instrument insertion channel of the endoscope. In this light, for example, Japanese Patent Laid-Open No. S57-190541, Japanese Patent Laid-Open No. 2000-207, and Japanese Patent Laid-Open No. 2007-117394 disclose an apparatus capable of electrically operating a treatment instrument and which automatically inserts into and pulls out the treatment instrument from a treatment instrument insertion channel of an endoscope for the purpose of improving handleability of the treatment instrument.

A conventional apparatus includes: a treatment instrument insert/remove mode in which the treatment instrument is inserted to the treatment instrument insertion channel at high speed or pulled out from the treatment instrument insertion channel at high speed; and a treatment instrument advance/retreat mode in which treatment operations are facilitated by advancing/retreating the treatment instrument at low-speed in a state where the treatment instrument protrudes from the distal end of the endoscope. Switching between these modes is either performed manually using switching means provided separately, or automatically through the detection of the insertion length of the treatment instrument.

SUMMARY OF THE INVENTION

A medical system according to the present invention includes: a medical instrument having a treatment portion for performing treatment operations on living body tissue; a treatment portion displacement mechanism for displacing the position of the treatment portion of the medical instrument; a treatment detection portion that detects whether the treatment portion is in a treatment state or a non-treatment state; and a control portion that controls displacement of the treatment portion by controlling the treatment portion displacement mechanism according to detection results from the treatment detection portion.

The above and other objects, features and advantages of the invention will become more clearly understood from the following description referring to the accompanying drawings.

BRIEF DESCRIPTION OF THE DRAWINGS

FIG. 6 is a diagram including a block display of a configuration of an endoscopic system according to a second modification of the first embodiment to which a high-frequency snare has been set;

DETAILED DESCRIPTION OF THE PREFERRED EMBODIMENTS

Embodiments of the present invention will be described below with reference to the drawings.

First Embodiment

First, a first embodiment of the present invention will be described below with reference to FIGS. 1 to 3.

Figure 1:
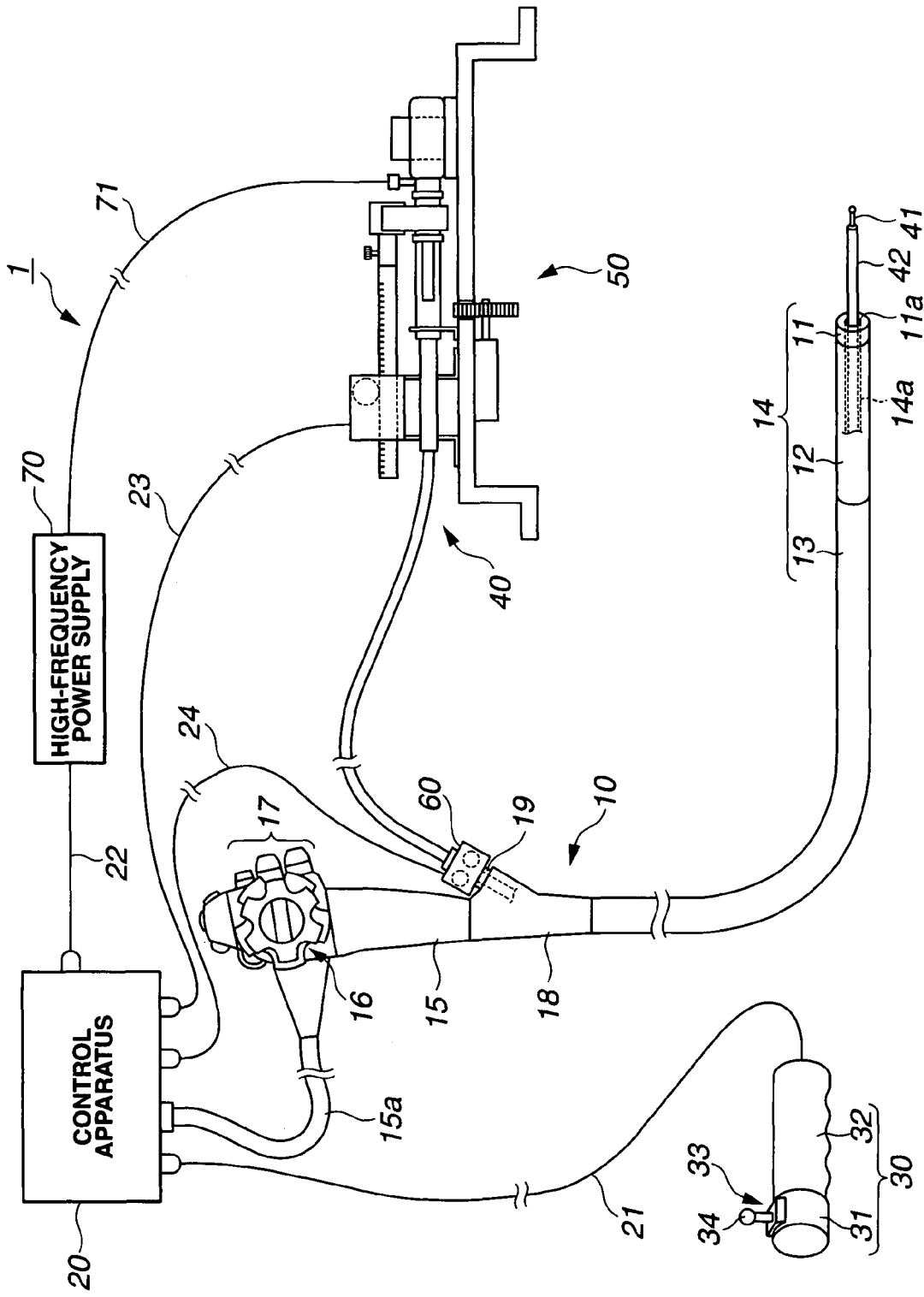
FIG. 1 is a diagram showing an overall configuration of an endoscopic system according to a first embodiment of the present invention to which a high-frequency knife has been set.
Figure 2:
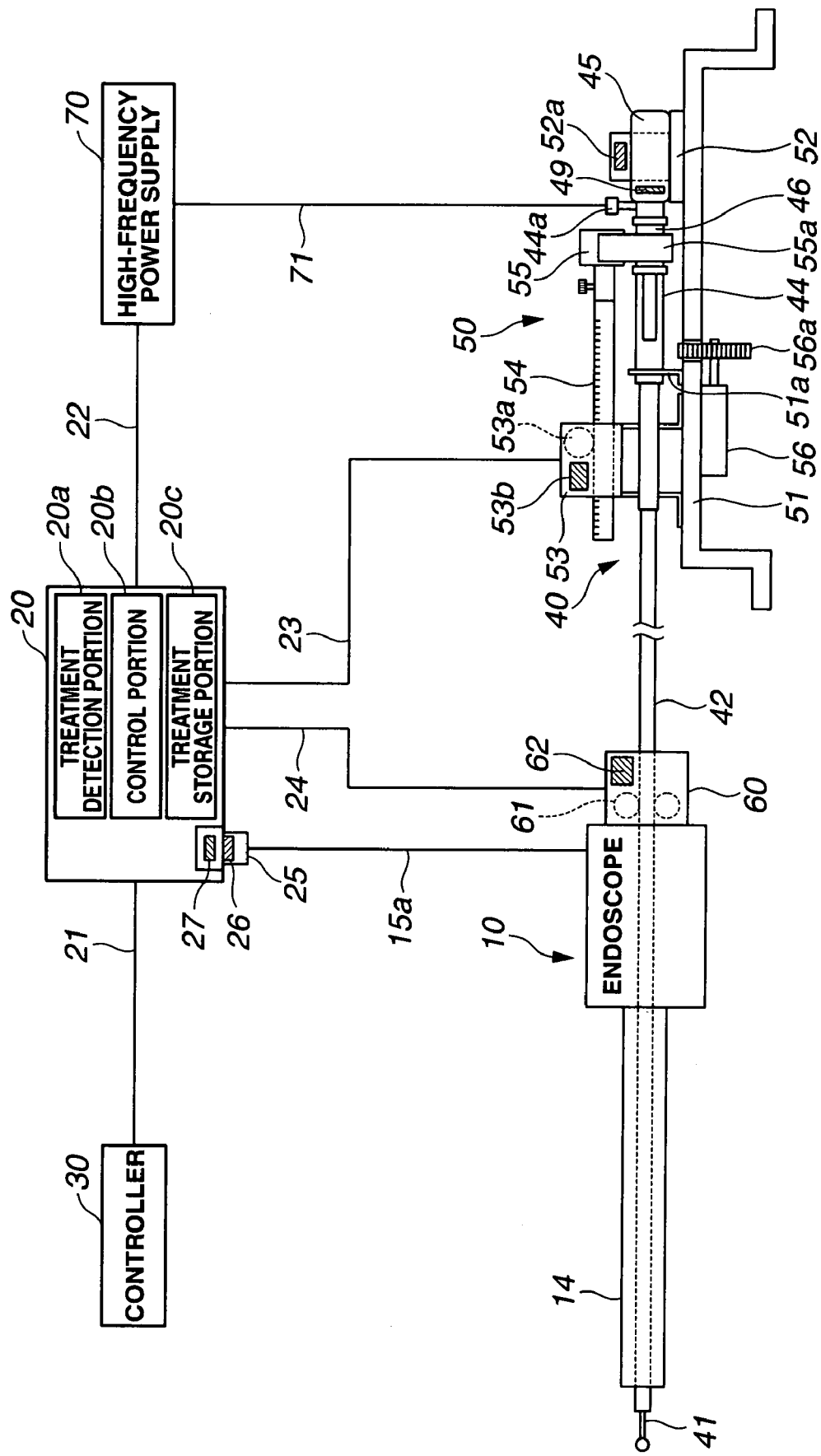
FIG. 2 is a diagram including a block display of a configuration of the endoscopic system shown in FIG. 1.
Figure 3:
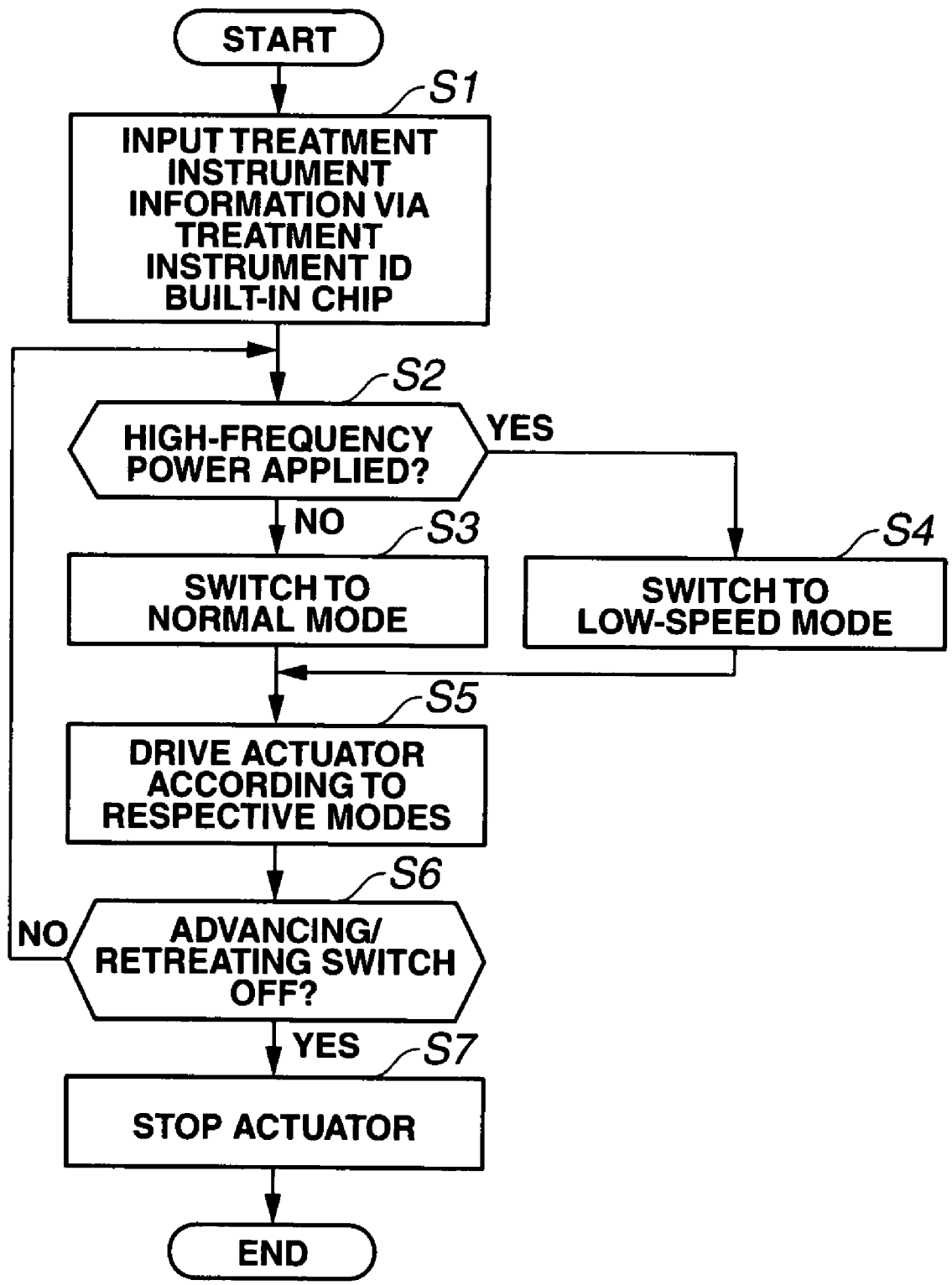
FIG. 3 is a flowchart illustrating control performed by a control apparatus of the endoscopic system shown in FIG. 1.

FIGS. 1 to 3 are drawings according to the first embodiment of the present invention, in which: FIG. 1 is a diagram showing an overall configuration of an endoscopic system to which a high-frequency knife has been set; FIG. 2 is a diagram including a block display of a configuration of the endoscopic system shown in FIG. 1; and FIG. 3 is a flowchart illustrating control performed by a control apparatus of the endoscopic system shown in FIG. 1.

As shown in FIG. 1, an endoscopic system 1 that is a medical system according to the present embodiment primarily comprises: an endoscope 10; a control apparatus 20 that also functions as a light source apparatus and a video processor; a controller 30 that is an operation instruction apparatus; a treatment instrument 40 that is an medical instrument provided with a treatment portion 41 that performs predetermined treatment on body cavity tissue; a treatment instrument electrical operation apparatus 50 that is a treatment portion operation apparatus that electrically operates the treatment portion 41; a treatment instrument insertion portion electrical advance/retreat apparatus (hereinafter simply described as the electrical advance/retreat apparatus) 60 that is a treatment portion displacement mechanism for advancing and retreating a sheath 42 of the treatment instrument 40; and a high frequency power supply 70 that applies high-frequency current to the treatment instrument 40.

The endoscope 10 shown in FIG. 1 is configured so as to comprise: an endoscope insertion portion (hereinafter abbreviated to the insertion portion) 14; an operation portion 15 to which the insertion portion 14 is connected; and a universal cord 15a detachable to the control apparatus 20.

The operation portion 15 of the endoscope 10 also functions as a grasping portion to an operator, and is provided on a proximal end-side of the insertion portion 14. The universal code 15a projects from a lateral side of the operation portion 15, and a connector portion of a proximal end thereof is detachably connected to the control apparatus 20.

The insertion portion 14 of the endoscope 10 is configured by consecutively installing, in order from the distal end side: a rigid distal end portion 11; a bendable bending portion 12; and a flexible tube portion 13 that is flexible. A distal end aperture 11a is provided at the distal end portion 11.

A bend preventing portion 18 to which is connected the proximal end of the flexible tube portion 13 is provided at the operation portion 15 of the endoscope 10. Provided at the operation portion 15 are: two bending knobs 16 for performing bend operations of the bending portion 12; function switches 17 including an air and water supply button for supplying air and water and a suction button for performing suction; and various switches for performing control on endoscopic images obtained through image pickup devices provided at the distal end portion 11, and the like.

Moreover, disposed at the insertion portion 14 of the endoscope 10 is a treatment instrument insertion channel 14a that opens at a treatment instrument insertion hole 19 provided on the bend preventing portion 18 and which communicates with the distal end aperture 11a.

The controller 30 shown in FIG. 1 has an approximately columnar shape. The controller 30 comprises: a rigid main body portion 31; and a grip body 32 consecutively installed to the main body portion 31 and which is, for example, an elastic member. In addition, a signal cable 21 projects from a proximal end face-side of the grip body 32. The proximal end-side of the signal cable 21 is detachably electrically connected to the control apparatus 20.

An operation instruction portion 33 is provided on a lateral peripheral face of the main body portion 31. The operation instruction portion 33 is provided with an operation lever 34 that is, for instance, of the joystick type. A tilt operation of the operation lever 34 by the operator to the distal end side causes an instruction signal for advancing the sheath 42 of the treatment instrument 40, to be described later, to be outputted from the operation instruction portion 33 to the control apparatus 20. A tilt operation of the operation lever 34 to the proximal end side causes an instruction signal for retreating the sheath 42 of the treatment instrument 40, to be described later, to be outputted from the operation instruction portion 33 to the control apparatus 20.

In addition, the operation instruction portion 33 is provided with a switch, not shown, for turning ON/OFF the high frequency power supply 70 that applies a high frequency to the treatment instrument 40 that performs treatment using high frequency.

Furthermore, the control apparatus 20 shown in FIG. 1 is provided with: a lamp (not shown) that supplies illumination; a signal processing circuit (not shown), and the like. The signal processing circuit performs: processing for generating a drive signal for driving an image pickup device (not shown) such as a CCD provided at the distal end portion of the endoscope; processing for generating a video signal from an electric signal transmitted from the image pickup device, and the like. A display apparatus such as a liquid crystal display (not shown) that displays endoscopic images is connected to the control apparatus 20.

In the present embodiment, the treatment instrument 40 shown in FIG. 1 is, for instance, a high-frequency knife (which hereinafter shall be described as the high-frequency knife 40 in the present embodiment), and is provided with the above-mentioned sheath 42 that is a flexible tube body having predetermined resilience.

The sheath 42 is provided at a distal end portion thereof with a treatment portion 41 that is, in this case, an electrical scalpel having a globular distal end insulated chip. In the present embodiment, the treatment portion 41 is electrically connected to a high-frequency power transmission cable, not shown, that is inserted to the sheath 42 and which transmits high frequency outputted from the high frequency power supply 70.

As shown in FIG. 2, a handle portion 44 of the high-frequency knife 40 comprises: a finger grip ring 45 and a slider 46. The finger grip ring 45 has a hole portion in which, for instance, a thumb of the operator is placed. The slider 46 is provided with a pair of flanges on which, during general use, a middle finger and a ring finger of the operator are placed. Moreover, the handle portion 44 is provided with a connector portion 44a for establishing electrical connection to the high frequency power supply 70 via the high-frequency cable 71.

It should be noted that the slider 46 of the high-frequency knife 40 is designed so that the operator may position his/her finger on the slider 46 for easy grasping, and in other treatment instruments to be described later, becomes operation means for operating the treatment portion 41. In other words, with the high-frequency knife 40 according to the present embodiment, the slider 46 is provided for easier grasping by the operator, and not necessarily for operating the treatment portion 41.

The electrical advance/retreat apparatus 60 shown in FIG. 2 is detachably provided at the treatment instrument insertion hole 19 (refer to FIG. 1) of the endoscope. The electrical advance/retreat apparatus 60 is electrically connected to the control apparatus 20 by an electric cable 24 having a signal line inserted therein. The electrical advance/retreat apparatus 60 advances or retreats the sheath 42 of the high-frequency knife 40 based on operations of the operation lever 34 (refer to FIG. 1) of the controller 30.

The electrical advance/retreat apparatus 60 includes two rotatable rollers 61 inside a chassis thereof. These two rollers 61 are respectively configured of elastic resin members, whereby one of the rollers 61 is driven by a motor, not shown, that is a driving source.

In other words, the sheath 42 of the high-frequency knife 40 is disposed between the two rollers 61. Accordingly, the exterior faces of the sheath 42 are pressed and held between the two rollers 61.

In addition, the other roller 61 that is rotated by a motor (not shown) that is a driving source and which is disposed within the electrical advance/retreat apparatus 60 advances/retreats the sheath 42 along a rotating direction by means of friction caused by pressing.

In other words, by driving the motor in a state where the sheath 42 is held between the two rollers 61, the sheath 42 that is held between the two rollers 61 is displaced in accordance with the rotation of one of the rollers 61. Drive-control of the rotating direction of the motor inside the electrical advance/retreat apparatus 60 advances or retreats the sheath 42 inside the treatment instrument insertion channel 14a of the endoscope 10.

In addition, the drive control of the motor of the electrical advance/retreat apparatus 60 is performed by the control apparatus 20 based on the operations of the operation lever 34 of the controller 30. The respective rollers 61 are rotatably supported by a rotating shaft securely installed on the chassis or the motor shaft of the motor so that the respective roller faces are spaced at a predetermined interval.

Furthermore, a rotation detection sensor 62 that is a detection portion that detects the revolutions of the roller 61 is built into the electrical advance/retreat apparatus 60. The detected value of the rotation detection sensor 62 is outputted to the control apparatus 20 via the electric cable 24. In other words, the control apparatus 20 calculates the displacement (amount of projection) of the sheath 42 of the high-frequency knife 40 based on the detected value from the rotation detection sensor 62. Moreover, the sensor for detecting a displacement (amount of projection) of the sheath 42 of the high-frequency knife 40 need not be limited to the rotation detection sensor 62 that detects revolution of the roller 61. For example, an optical sensor may be used which counts indexes provided at regular intervals on the sheath 42, whereby the displacement (amount of projection) of the sheath 42 of the high-frequency knife 40 is calculated based on the detected results.

The electrical operation apparatus 50 shown in FIGS. 1 and 2 has a base body 51. The base body 51 comprises: a ring holding portion 52; a retaining box 53; and a motor 56 having a gear 56a that is a spur gear.

The retaining box 53 is securely installed on the base body 51 via a leg portion. A rack 54 forming a linear tooth profile is rectilinearly retained by the retaining box 53 so as to be advanceable and retreatable. A pinion gear 53a that meshes with the linear tooth profile of the rack 54 is arranged in the retaining box 53.

The pinion gear 53a is securely installed on the motor shaft of a motor, not shown. In other words, the motor is rotated in a state where the pinion gear 53a meshes with the linear tooth profile provided on the rack 54. This causes the pinion gear 53a securely installed on the motor shaft to rotate, thereby advancing/retreating the rack 54.

One end of the composite cable 23 is connected to the retaining box 53, while the other end of the composite cable 23 is detachably electrically connected to the control apparatus 20.

In addition, a slider holding portion 55 having a retaining portion 55a is fixed by a screw to an end portion of the rack 54. The retaining portion 55a of the slider holding portion 55 holds a slider 46 provided on the handle portion 44 of the high-frequency knife 40. More specifically, the retaining portion 55a performs retention so as to hold a body portion between a pair of flanges provided on the slider 46.

Moreover, although unused in the present invention, drive instructions to the motor inside the retaining box 53 are performed by leftward or rightward tilt operations of the operation lever 34 of the controller 30. As an example, tilting the operation lever 34 rightwards while facing the front of the controller 30 causes the slider 46 to move in a direction in which the rack 54 pushes out forward the operation wire for operating the treatment portion 41 which is used for other treatment instruments 40 from the retaining box 53. Conversely, tilting the operation lever 34 leftwards while facing the front causes the slider 46 to move in a direction in which the rack 54 pushes out the operation wire backwards from the retaining box 53.

In addition, a slide detection sensor 53b that detects advance/retreat displacement of the rack 54 to detect displacement of the slider 46 is provided in the retaining box 53. The detected value that is detected by the slide detection sensor 53b is outputted to the control apparatus 20 via the composite cable 23.

Moreover, a hole portion of the finger grip ring 45 provided on the handle portion 44 of the high-frequency knife 40 is inserted to and arranged at the ring holding portion 52. As a result, the handle portion 44 of the high-frequency knife 40 is integrally securely retained by the electrical operation apparatus 50.

At this point, the handle portion 44 is retained and fixed by a treatment instrument fixing portion 51a securely installed on a front face of the base body 51. In addition, as shown in FIG. 2, the handle portion 44 of the high-frequency knife 40 is disposed parallel to and separated from the base body 51 by a predetermined distance by the treatment instrument fixing portion 51a.

A gear 56a is provided on the motor shaft of the motor 56 provided on a rear face side of the base body 51. The gear 56a is provided so as to slightly protrude to the front face side of the base body 51 from a hole portion provided on the base body 51. Moreover, in the present embodiment, the motor 56 is not driven and is instead used to rotate the treatment portions 41 of other treatment instruments 40 around a shaft.

In addition, the control apparatus 20 of the present embodiment is provided with an endoscope ID read sensor 27 in the connector 25 which, when the connector 25 of the universal cord 15a of the endoscope 10 is connected thereto, reads endoscope information and which, in this case, is a read portion of RFID (Radio Frequency Identification).

The endoscope ID read sensor 27 reads model information of the connected endoscope 10, the length of the insertion portion 14, the channel length of the treatment instrument insertion channel 14a disposed in the insertion portion 14, and the like from an endoscope ID internal IC chip 26 built into the connector 25 of the universal cord 15a.

Furthermore, the ring holding portion 52 of the electrical operation apparatus 50 is provided with a treatment instrument ID read sensor 52a which, when the finger grip ring 45 is inserted into and disposed in a predetermined state on the ring holding portion 52, reads treatment instrument information and which, in this case, is a read portion of RFID (Radio Frequency Identification).

This treatment instrument ID read sensor 52a reads model information of the disposed high-frequency knife 40, the length of the sheath 42 and the like from a treatment instrument ID internal IC chip 49 that is an integrated circuit and the like built into the finger grip ring 45 of the high-frequency knife 40. In addition, information which, in this case, is model information of the high-frequency knife 40 and the like that is read by the treatment instrument ID read sensor 52a is outputted to the control apparatus 20 via the composite cable 23.

In addition, the electrical operation apparatus 50 performs electrical exchange with the control apparatus 20 via the composite cable 23. In other words, the composite cable 23 supplies to and receives from the control apparatus 20: a motor drive current inside the retaining box 53 of the electrical operation apparatus 50; a drive current of the motor 56; a model information signal from the treatment instrument ID read sensor 52a; and a detected value from the slide detection sensor 53b.

Moreover, provided within the control apparatus 20 are a treatment detection portion 20a, a control portion 20b and a treatment storage portion 20c which are respectively electrically connected.

The treatment detection portion 20a is a sensor that detects output of drive signals to the electrical operation apparatus 50, the electrical advance/retreat apparatus 60 and the high frequency power supply 70, and also detects input of detection signals from various sensors. In addition, the control portion 20b is a CPU that performs control of the control apparatus 20. Furthermore, the treatment storage portion 20c is a memory that stores drive histories of the electrical operation apparatus 50, the electrical advance/retreat apparatus 60 and the high frequency power supply 70 that electrically perform treatment operations of the various treatment instruments.

The high frequency power supply 70 is connected to a communication cable 22 that is electrically connected to the control apparatus 20 and a high-frequency cable 71 connected to a connector portion 44a of the high-frequency knife 40. When a switch (not shown) of the controller 30 is turned on, the high frequency power supply 70 applies high frequency to the high-frequency knife 40 via the control apparatus 20.

When advancing/retreating the high-frequency knife 40, the endoscopic system 1 according to the present embodiment configured as described above is arranged to perform advance/retreat control of the sheath 42 in accordance with the treatment state where high frequency is applied to the treatment portion 41.

In addition, based on an inputted control table, the control apparatus 20 performs control according to the routine of the flowchart shown in FIG. 3. More specifically, in a state where the high-frequency knife 40 is not yet inserted into the treatment instrument insertion channel 14a of the endoscope 10, the endoscopic system 1 is first set to a state where various devices are electrically connected as shown in FIGS. 1 and 2.

First, when introducing the high-frequency knife 40 to the treatment instrument insertion channel 14a of the endoscope 10, the operation lever 34 of the controller 30 is tilt-operated in a forward direction. In response, the control apparatus 20 drives the electrical advance/retreat apparatus 60. Then, the operator sends in the sheath 42 of the high-frequency knife 40 into the treatment instrument insertion channel 14a of the endoscope 10 by means of the two rollers 61 that hold the sheath 42 therebetween.

At this point, a drive instruction signal from the operation lever 34 of the controller 30 acts as a trigger and causes the control apparatus 20 to perform control based on the routine (steps) of the flowchart shown in FIG. 3.

First, as shown in FIG. 3, the control apparatus 20 reads treatment instrument information of the high-frequency knife 40 inputted from the treatment instrument ID read sensor 52a and stored in the treatment instrument ID internal IC chip 49 at the treatment detection portion 20a. The treatment instrument information is inputted from the treatment detection portion 20a to the control portion 20b (S1). At this point, in the case where the treatment instrument is the high-frequency knife 40, the control apparatus 20 performs control in accordance with the respective steps of the flowchart shown in FIG. 3.

Moreover, in the present embodiment, while the control apparatus 20 is configured to detect a treatment instrument set to the electrical advance/retreat apparatus 60, the control apparatus 20 is not limited to this configuration. Instead, the present invention may be arranged so that the user arbitrarily inputs the treatment instrument to be used to the control apparatus 20.

Then, the control portion 20b of the control apparatus 20 judges whether the high frequency power supply 70 has been energized (S2). At this point, when the high frequency power supply 70 is in an OFF state, the control portion 20b switches to the normal mode (S3).

In this case, the normal mode refers to a normal advance/retreat mode in which the sheath 42 of the high-frequency knife 40 advances/retreats at a preset, predetermined speed. In other words, a state where high-frequency is not applied to the high-frequency knife 40 is a state where only an operation to advance/retreat the sheath 42 of the high-frequency knife 40 is performed.

On the other hand, when the high frequency power supply 70 is in an ON state in step S2, the control portion 20b switches to low-speed mode (S4). In this case, low-speed mode refers to a low-speed advance/retreat mode in which the sheath 42 of the high-frequency knife 40 advances/retreats at a preset, predetermined speed that is slower than the normal advance/retreat mode.

In other words, when an ON signal is inputted from the switch of the controller 30, the control portion 20b drives the high frequency power supply 70 so as to enable dissection of living body tissue at a high frequency by the treatment portion 41 of the high-frequency knife 40. In this state where an ON signal is inputted from the switch of the controller 30, the control portion 20b switches to the low-speed mode in step S4.

Next, in accordance with each switched mode, the control portion 20b drives the electrical advance/retreat apparatus 60 that is an actuator (S5). More specifically, when a transition is made to step S3, the control portion 20b switches to the normal mode and drives the electrical advance/retreat apparatus 60 in correspondence to a predetermined speed at which the sheath 42 of the high-frequency knife 40 advances/retreats. On the other hand, when a transition is made to step S4, the control portion 20b switches to low-speed mode and drives the electrical advance/retreat apparatus 60 in correspondence to a predetermined speed that is slower than the normal mode at which the sheath 42 of the high-frequency knife 40 advances/retreats.

In other words, the control portion 20b variably outputs voltage to the motor that rotationally drives the roller 61 of the electrical advance/retreat apparatus 60 according to preset rotary speeds of the respective modes. As a result, the advance/retreat speed of the sheath 42 of the high-frequency knife 40 varies according to the ON/OFF state of the high frequency power supply 70.

To elaborate, during a simple advance/retreat operation of the sheath 42 in a non-treatment state where high frequency is not applied to the treatment portion 41 of the high-frequency knife 40, advance/retreat of the sheath 42 is executed at a set, relatively high speed by the electrical advance/retreat apparatus 60. On the other hand, during an advance/retreat operation of the sheath 42 in a treatment state where high frequency is applied to the treatment portion 41 of the high-frequency knife 40, advance/retreat of the sheath 42 is executed by the electrical advance/retreat apparatus 60 at a speed that is lower than the normal mode.

In addition, during driving of the electrical advance/retreat apparatus 60 according to the respective modes in step S5, the control portion 20b judges whether the operation lever 34 of the controller 30 is in an advance/retreat switch OFF state where the operation lever 34 is no longer operated (S6).

In other words, a neutral state of the operation lever 34 of the controller 30 where the operation lever 34 is neither tilted forward nor backward is a state where no instruction signals for driving the electrical advance/retreat apparatus 60 are inputted to the control portion 20b. In this state, the control portion 20b judges that the advance/retreat switch is turned OFF. In addition, when the operation lever 34 of the controller 30 is being continuously tilted forward or backwards, the control portion 20b judges that the advance/retreat switch is turned ON.

Furthermore, when the control portion 20b judges that the advance/retreat switch is turned ON, the control portion 20b returns to step S2 to repeat the routine of steps S2 to S6. On the other hand, when the control portion 20b judges that the advance/retreat switch is turned OFF, the control portion 20b suspends output of the drive signal of the electrical advance/retreat apparatus 60 that is an actuator and stops the electrical advance/retreat apparatus 60 (S7), thereby stopping the advance/retreat of the sheath 42 of the high-frequency knife 40 and concluding the control flowchart shown in FIG. 3.

As seen, since the endoscopic system 1 according to the present embodiment controls the advance/retreat speed of the sheath 42 of the high-frequency knife 40 during high-frequency application that is a treatment state to be used for endoscopic submucosal dissection (ESD) to a low speed, a configuration is realized that allows easier treatment operations for dissection of living mucosa. In addition, since the endoscopic system 1 controls the advance/retreat speed of the sheath 42 of the high-frequency knife 40 to a speed that is higher than the treatment state when high-frequency from the high frequency power supply 70 is not applied to the high-frequency knife 40, a configuration is realized that allows the high-frequency knife 40 to be inserted to and retracted from the treatment instrument insertion channel 14a of the endoscope 10 in a speedy manner, and approaches to treatment target areas to be performed in a speedy manner.

Moreover, using the control apparatus 20, the user may set the advance/retreat speed of the sheath 42 of the high-frequency knife 40 according to the above-described electrical advance/retreat apparatus 60 to a desired arbitrary speed for each mode in the non-treatment and treatment states.

First Modification

Next, a first modification of the present embodiment will be described below with reference to FIGS. 4 and 5. Note that the present modification uses a different treatment instrument 40 for the endoscopic system 1, and now uses a high-frequency hemostatic forceps that is used for arresting hemorrhage of living body tissue (hereinafter, this treatment instrument shall be described as the high-frequency hemostatic forceps 40). Accordingly, like reference characters shall be used for the various configurations of the endoscopic system. 1 described above and descriptions thereof will be omitted. Only different configurations and effects shall be described.

Figure 4:
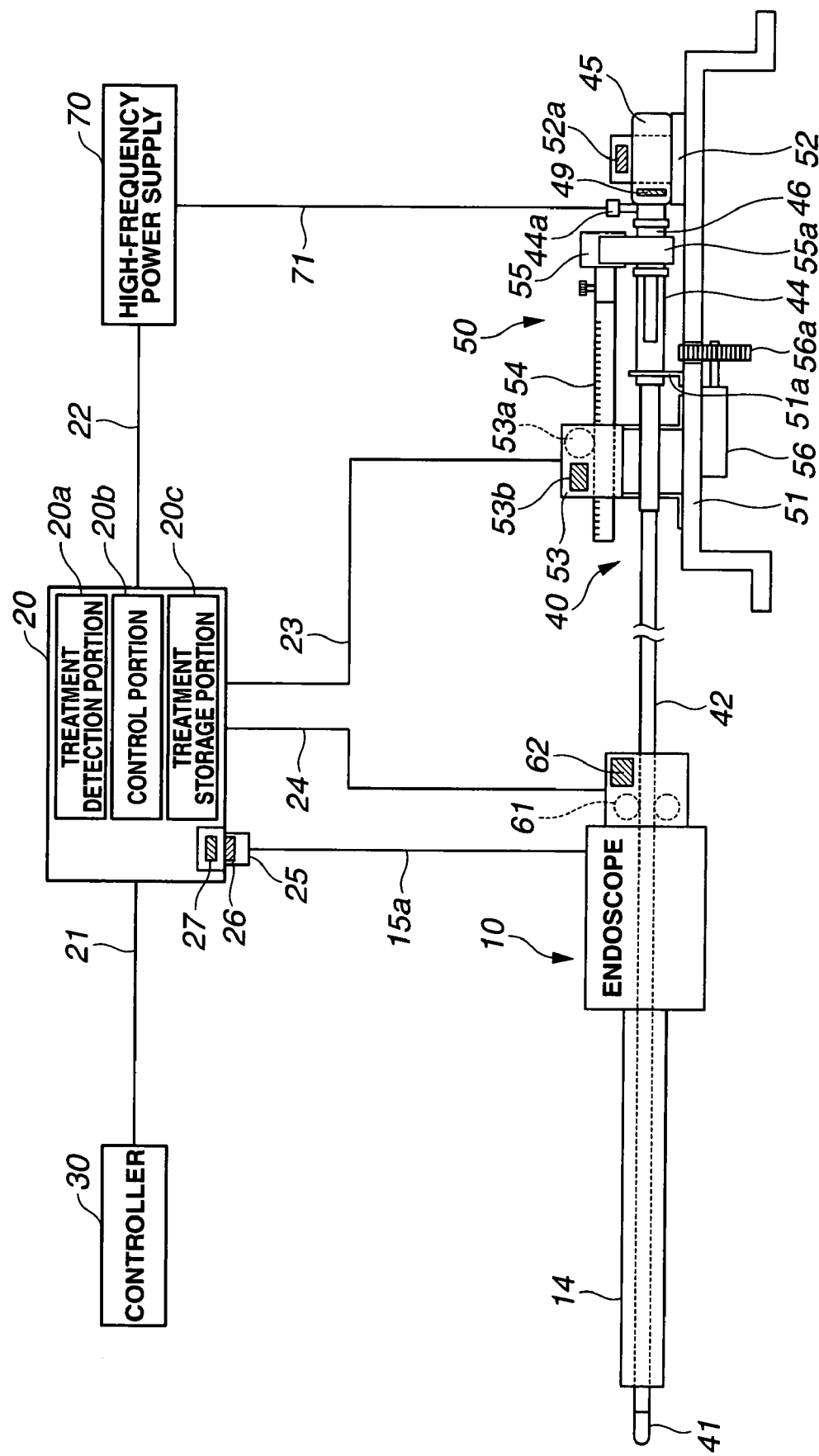
FIG. 4 is a diagram including a block display of a configuration of an endoscopic system according to a first modification of the first embodiment to which a high-frequency hemostatic forceps has been set.
Figure 5:
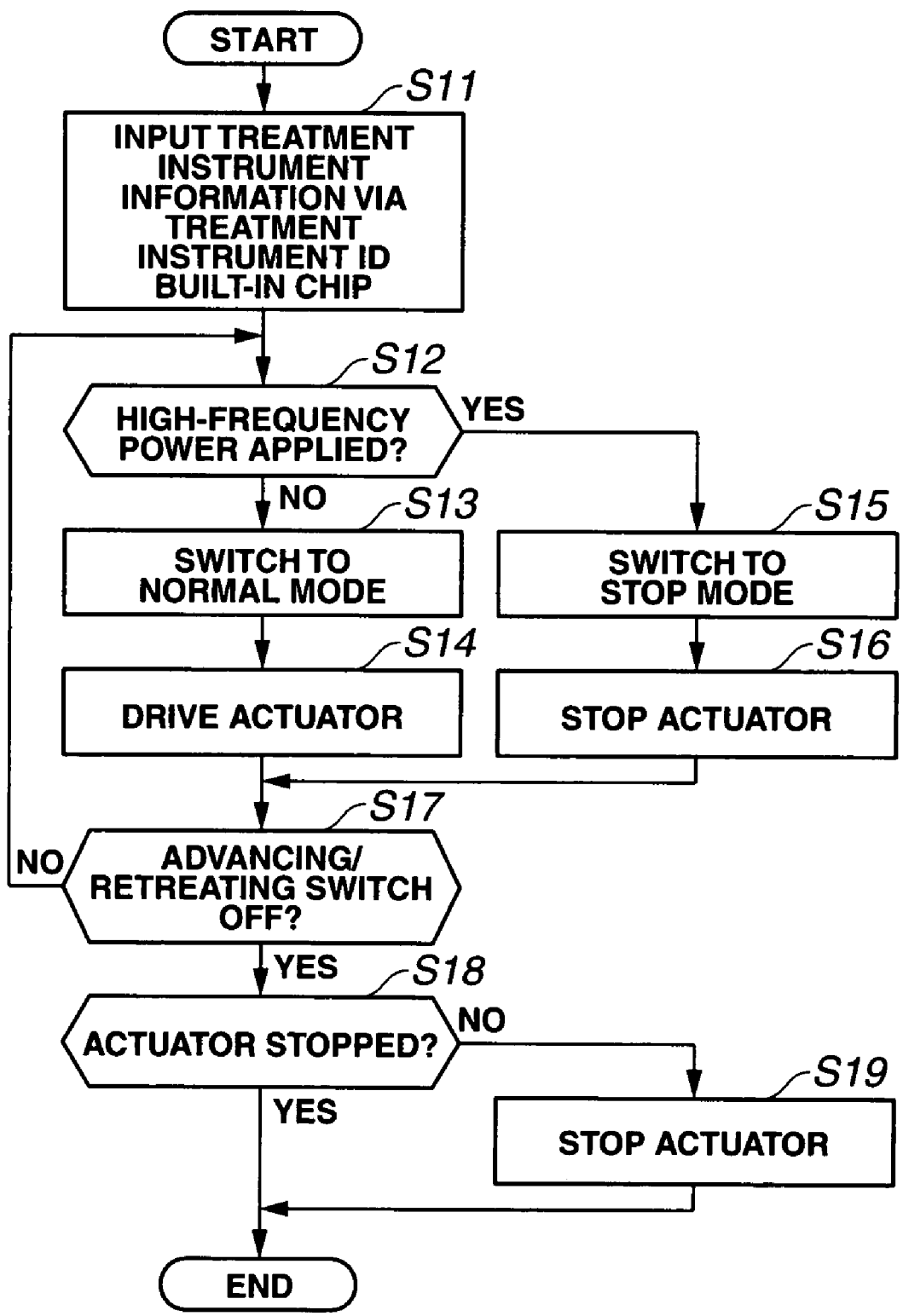
FIG. 5 is a flowchart illustrating control performed by a control apparatus of the endoscopic system shown in FIG. 4.

In addition, FIGS. 4 and 5 show the first modification of the present invention, in which: FIG. 4 is a diagram including a block display of a configuration of an endoscopic system to which a high-frequency hemostatic forceps has been set; while FIG. 5 is a flowchart illustrating control performed by a control apparatus of the endoscopic system shown in FIG. 4.

As shown in FIG. 4, a high-frequency hemostatic forceps 40 is set to the endoscopic system 1 according to the present modification. This high-frequency hemostatic forceps 40 is a treatment instrument for arresting hemorrhage of the living body tissue by means of a treatment portion 41 to which high frequency is applied. Other configurations of the high-frequency hemostatic forceps 40 are the same as the high-frequency knife described above.

With the high-frequency hemostatic forceps 40, the treatment portion 41 is placed against the hemorrhagic area, a high-frequency current is applied thereto and the tissue is coagulated and hemorrhage is arrested using heat generated locally at the hemorrhagic area. The high-frequency hemostatic forceps 40 is used by gently pressing the treatment portion 41 against the periphery of a blood vessel. In this case, the hemostatic effect may be improved by pressing the treatment portion 41 against the tissue for a period of time during high-frequency irradiation. In other words, the treatment portion 41 of the high-frequency hemostatic forceps 40 in a treatment state where high frequency is applied must be momentarily fixed at the position of the hemostasis target.

For this reason, during advance/retreat operations of the high-frequency hemostatic forceps 40, the endoscopic system 1 according to the present modification executes the control example illustrated by the flowchart of FIG. 5 using the control apparatus 20. Similarly, in this case, a drive instruction signal from the operation lever 34 of the controller 30 acts as a trigger and causes the control apparatus 20 to perform control based on the routine (steps) of the flowchart shown in FIG. 5.

More specifically, as shown in FIG. 5, the control apparatus 20 first reads treatment instrument information of the high-frequency knife 40 inputted from the treatment instrument ID read sensor 52*a* and stored in the treatment instrument ID internal IC chip 49 at the treatment detection portion 20*a*. The treatment instrument information is inputted from the treatment detection portion 20*a* to the control portion 20*b* (S11). At this point, in the case where the treatment instrument is the high-frequency hemostatic forceps 40, the control apparatus 20 performs control in accordance with the respective steps of the flowchart shown in FIG. 3.

Then, the control portion 20*b* of the control apparatus 20 judges whether the high frequency power supply 70 has been energized (S12). At this point, when the high frequency power supply 70 is in an OFF state, the control portion 20*b* switches to a normal mode (S13).

In this case, in the same manner as described above, the normal mode refers to a normal advance/retreat mode in which the sheath 42 of the high-frequency hemostatic forceps heat probe 40 advances/retreats at a preset, predetermined speed.

Next, in accordance with the normal mode, the control portion 20*b* drives the electrical advance/retreat apparatus 60 that is an actuator (S14). More specifically, when a transition is made to step S13, the control portion 20*b* switches to the normal mode and drives the electrical advance/retreat apparatus 60 in correspondence to a predetermined speed at which the sheath 42 of the high-frequency hemostatic forces 40 advances/retreats.

On the other hand, when the high frequency power supply 70 is in an ON state in step S12, the control portion 20*b* switches to a stop mode (S15). In this case, the stop mode refers to a mode in which the advance/retreat of the sheath 42 of the high-frequency hemostatic forceps 40 is stopped. The control portion 20*b* then stops the electrical advance/retreat apparatus 60 that is an actuator (S16).

In other words, when an ON signal is inputted from the switch of the controller 30, the control portion 20*b* drives the high frequency power supply 70 so as to enable high-frequency hemostasis of the living body tissue by the treatment portion 41 of the high-frequency hemostatic forceps 40. In this state where an ON signal is inputted from the switch of the controller 30, the control portion 20*b* switches to the stop mode in step S15.

In other words, the control portion 20*b* outputs drive signals or stops output thereof to the motor that rotationally drives the roller 61 of the electrical advance/retreat apparatus 60 according to the respective modes. As a result, according to the ON/OFF state of the high frequency power supply 70, the advance/retreat of the sheath 42 of the high-frequency hemostatic forceps 40 is driven or stopped.

To elaborate, during a simple advance/retreat operation of the sheath 42 in a non-treatment state where high frequency is not applied to the treatment portion 41 of the high-frequency hemostatic forceps 40, advance/retreat of the sheath 42 is executed at a set speed by the electrical advance/retreat apparatus 60. On the other hand, during an advance/retreat operation of the sheath 42 in a treatment state where high frequency is applied to the treatment portion 41 of the high-frequency hemostatic forceps heat probe 40, the driving of the electrical advance/retreat apparatus 60 is stopped so that advance/retreat of the sheath 42 cannot be performed by the electrical advance/retreat apparatus 60.

In addition, during driving or stopping of the electrical advance/retreat apparatus 60 according to the respective modes, the control portion 20*b* judges whether the operation lever 34 of the controller 30 is in an advance/retreat switch OFF state where the operation lever 34 is no longer operated (S17).

In other words, in a neutral state of the operation lever 34 of the controller 30 where the operation lever 34 is neither tilted forward nor backward that is a state where no instruction signals for driving the electrical advance/retreat apparatus 60 are inputted to the control portion 20*b*, the control portion 20*b* judges that the advance/retreat switch is OFF. In addition, when the operation lever 34 of the controller 30 is being continuously tilted forward or backwards, the control portion 20*b* judges that the advance/retreat switch is turned ON.

Furthermore, when the control portion 20*b* judges that the advance/retreat switch is turned ON, the control portion 20*b* returns to step S12 to repeat the routine of steps S12 to S17. On the other hand, if the control portion 20*b* judges that the advance/retreat switch is turned OFF, the control portion 20*b* judges whether the electrical advance/retreat apparatus 60 that is an actuator is stopped (S18).

In this ease, when the electrical advance/retreat apparatus 60 is driven or, in other words, when a drive signal is being outputted to the electrical advance/retreat apparatus 60, the control portion 20*b* suspends output of the drive signal to the electrical advance/retreat apparatus 60 and stops the electrical advance/retreat apparatus 60 (S19). This stops the advance/retreat of the sheath 42 of the high-frequency hemostatic forceps 40, thereby concluding the control flowchart in FIG. 5.

On the other hand, in step S18, when the electrical advance/retreat apparatus 60 is stopped or, in other words, when a drive signal is not being outputted to the electrical advance/retreat apparatus 60, the control portion 20*b* concludes the control flowchart shown in FIG. 5 as is.

As a result of the above, when a treatment instrument of the high-frequency hemostatic forceps 40 is used, the endoscopic system 1 according to the present embodiment performs control to stop advance/retreat of the sheath 42 during high-frequency irradiation. Therefore, the endoscopic system 1 is configured so that, in a treatment state where high frequency is applied to the treatment portion 41 of the high-frequency hemostatic forceps 40, hemostatic effects on the hemostasis target tissue area may be improved by securely maintaining a state where the treatment portion 41 is pressed against the tissue even when the operation lever 34 of the controller 30 is operated.

Second Modification

Next, a second modification of the present embodiment will be described below with reference to FIGS. 6 to 10. Note that the present modification also uses a different treatment instrument 40 for the endoscopic system 1, and now uses a high-frequency snare that is used for endoscopic polypectomy (hereinafter, this treatment instrument shall be described as the high-frequency snare 40). Accordingly, like reference characters shall be used for the various configurations of the endoscopic system 1 described above and descriptions thereof will be omitted. Only different configurations and effects shall be described.

Figure 6:
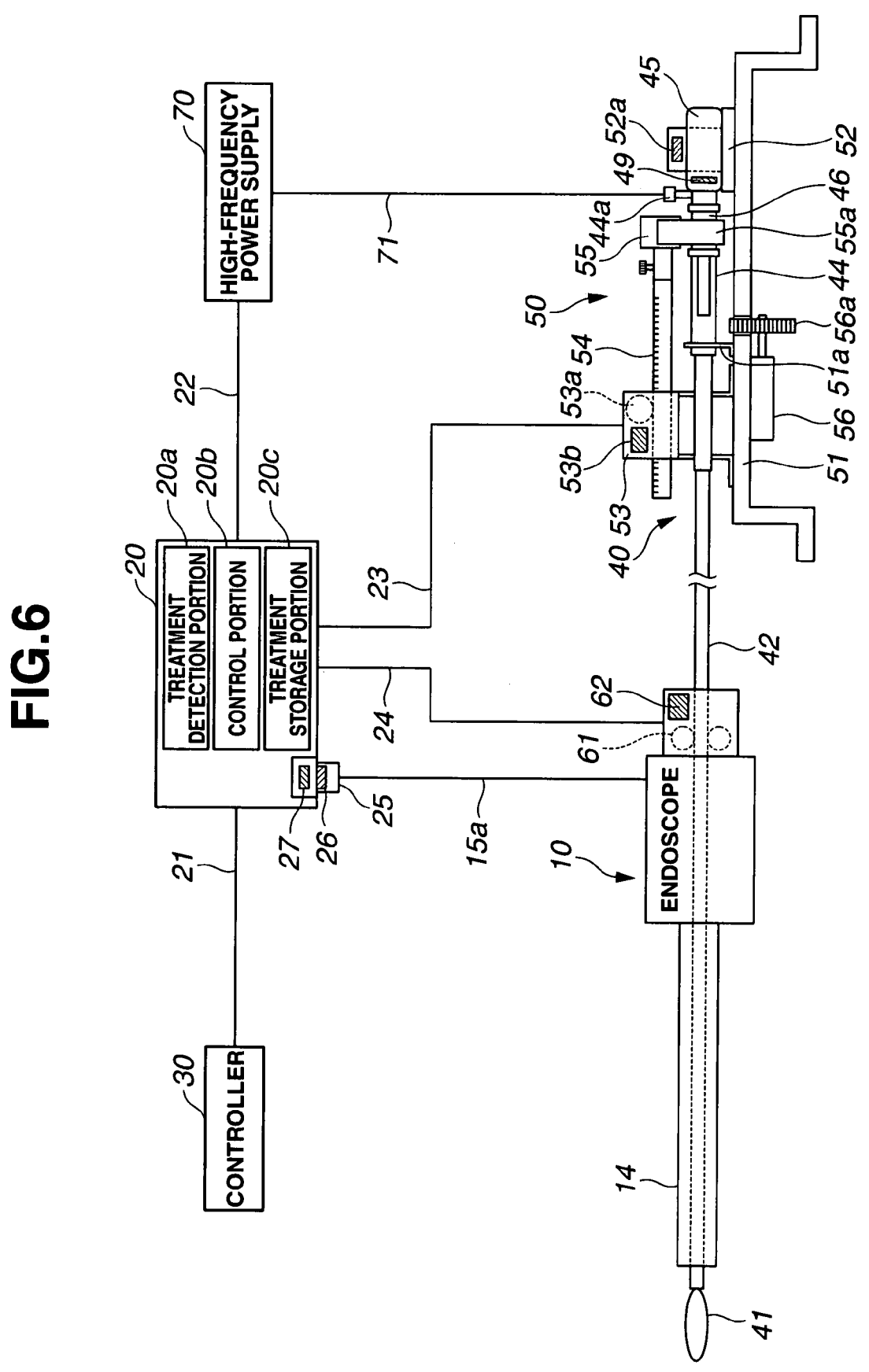
Figure 7:
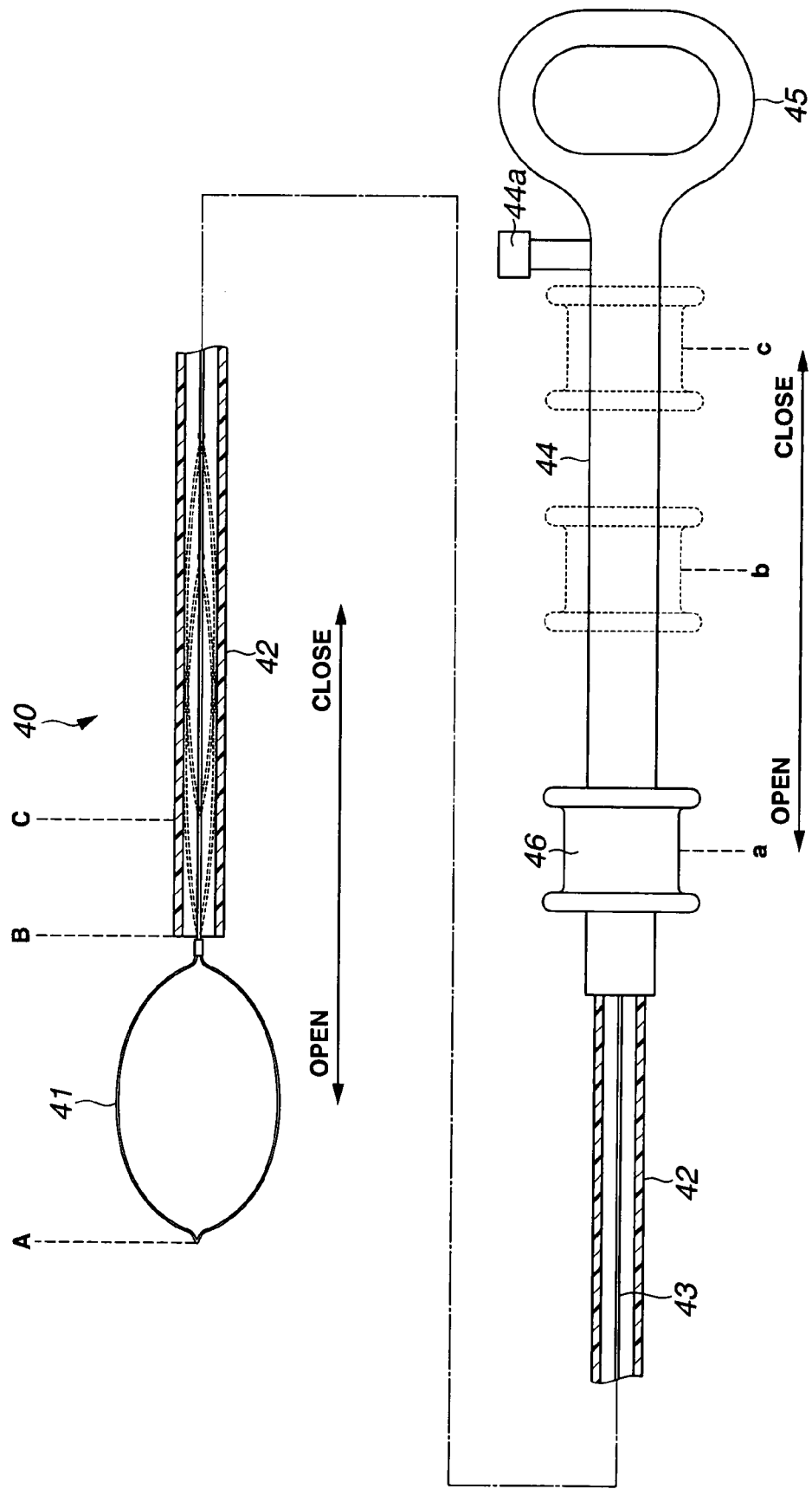
FIG. 7 is a cross sectional diagram showing a configuration of a high-frequency snare.
Figure 8:
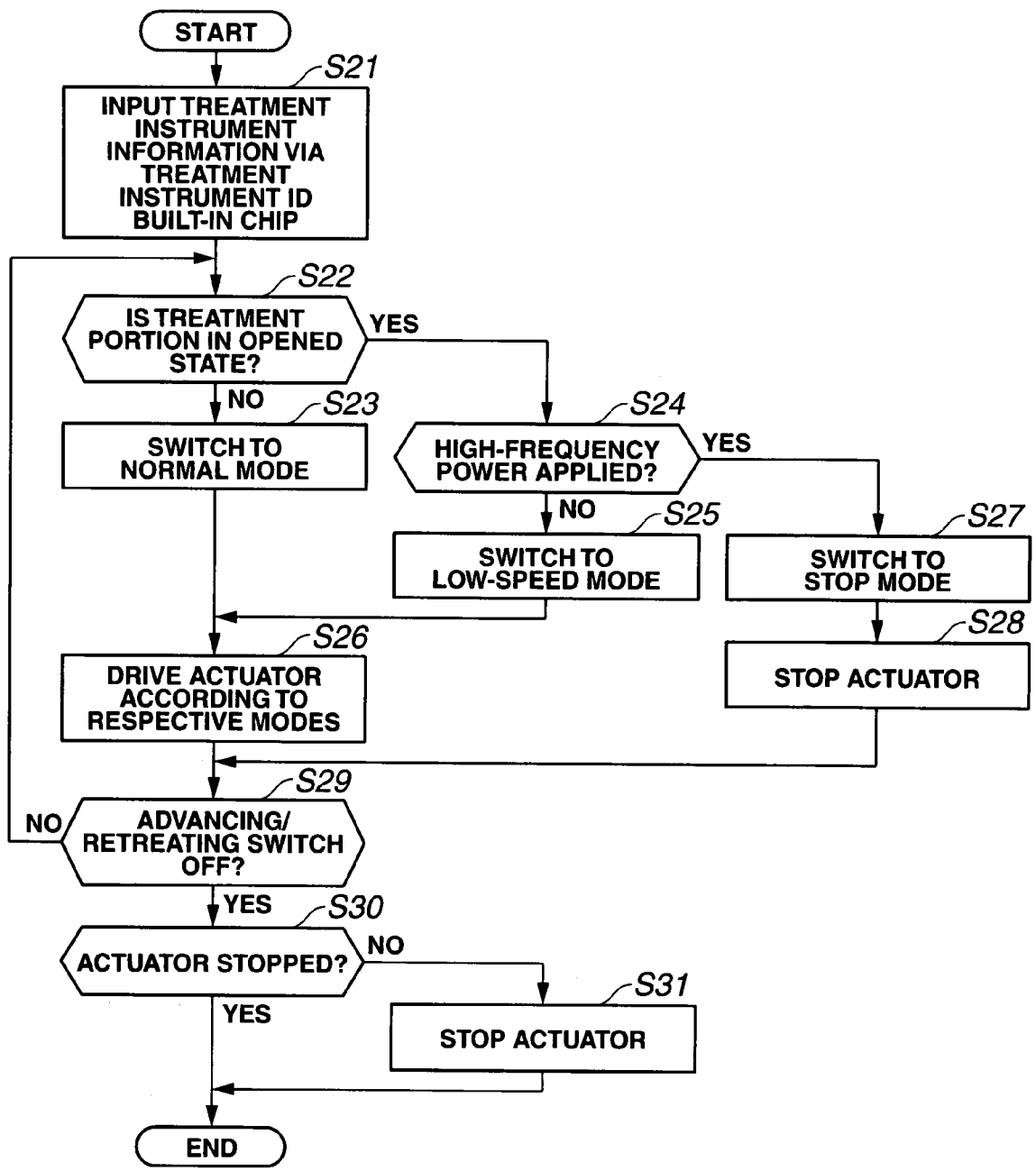
FIG. 8 is a flowchart illustrating control performed by a control apparatus of the endoscopic system shown in FIG. 6.
Figure 9:
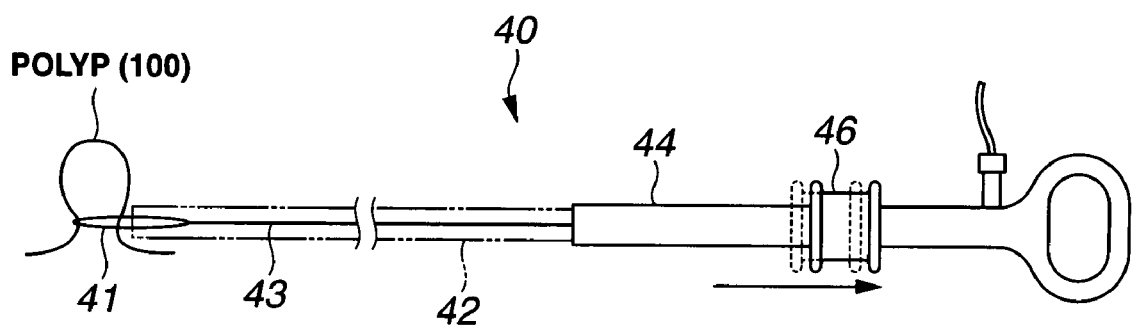
FIG. 9 is a diagram showing a state where a treatment portion of a high-frequency snare is constricting a polyp.
Figure 10:
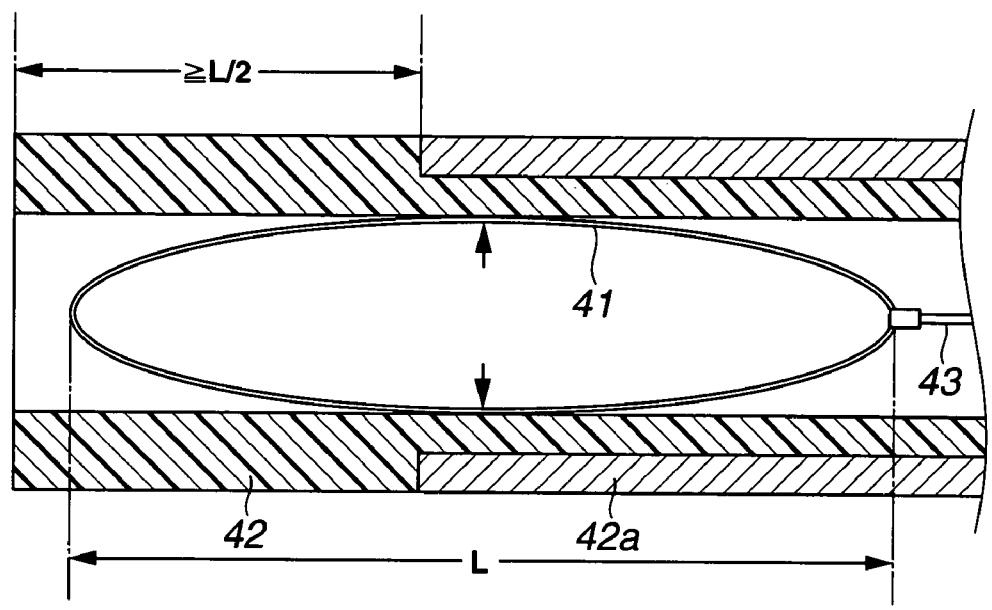
FIG. 10 is a cross sectional diagram showing a pressure sensor allocated on a sheath of a high-frequency snare.

FIGS. 6 to 10 show the second modification of the present invention, in which: FIG. 6 is a diagram including a block display of a configuration of an endoscopic system to which a high-frequency snare has been set; FIG. 7 is a cross sectional diagram showing a configuration of a high-frequency snare; FIG. 8 is a flowchart illustrating control performed by the control apparatus of the endoscopic system shown in FIG. 6; FIG. 9 is a diagram showing a state where the treatment portion of the high-frequency snare is constricting a polyp; and FIG. 10 is a cross sectional diagram showing a pressure sensor arranged on a sheath of the high-frequency snare.

As shown in FIG. 6, a high-frequency snare 40 is set to the endoscopic system 1 according to the present modification. This high-frequency snare 40 is a treatment instrument for removing polyps developed on living body tissue using a treatment portion 41 to which high frequency is applied.

More specifically, with the high-frequency snare 40, as shown in FIG. 7, a treatment portion 41 that is a snare wire made of metallic wire and which, in this case, has an elliptic looped shape is connected to the distal end of an operation wire 43. This metallic operation wire 43 is inserted into the sheath 42, and is pulled or relaxed in accordance with the displacement of the slider 46 of the handle portion 44. In addition, in order to apply high frequency outputted from the high frequency power supply 70 to the treatment portion 41, the operation wire 43 is configured so as to be electrically connected to the connector portion 44a of the handle portion 44.

In other words, in accordance with the advance/retreat of the operation wire 43 that is interlocked with the slider 46, as shown in FIG. 7, the treatment portion 41 spreads out in an elliptical shape during an open state. During a closed state, the treatment portion 41 transforms itself into a shape that allows housing inside a distal end portion of the sheath 42 and is introduced to or removed from the distal end portion of the sheath 42. Moreover, in the present embodiment, a slide detection sensor 53b inside the retaining box 53 detects an open/closed state of the treatment portion 41 of the high-frequency snare 40 from the advance/retreat displacement position of the slider 46 of the handle portion 44.

This judgment of the open/closed state of the treatment portion 41 uses as a border a position B, as shown in FIG. 7, at which the distal end of the treatment portion 41 is the same as the aperture surface of the sheath 42 in a state where the position of the slider 46 is represented by the reference character b and the dashed line. In other words, a state where the distal end of the treatment portion 41 protrudes even if only slightly past the aperture face of the sheath 42 shall be considered to be an open state of the treatment portion 41, while a state where the distal end of the treatment portion 41 is housed inside the sheath 42 shall be considered to be a closed state.

In addition, when the high-frequency snare 40 is in a state where the treatment portion 41 protrudes from the sheath 42, the displacement position a of the slider 46 represented by the solid line in FIG. 7 is the maximum open state where the distal end of the treatment portion 41 reaches position A. Furthermore, when the high-frequency snare 40 is in a state where the treatment portion 41 is housed in the sheath 42, the displacement position c of the slider 46 represented by the dashed line in FIG. 7 is the maximum closed state where the distal end of the treatment portion 41 is at position C.

According to the configuration described above, the endoscopic system 1 according to the present modification executes the control example illustrated by the flowchart of FIG. 8 using the control apparatus 20 during advance/retreat operations of the high-frequency snare 40. Similarly, in this case, a drive instruction signal from the operation lever 34 of the controller 30 acts as a trigger and causes the control apparatus 20 to perform control based on the routine (steps) of the flowchart shown in FIG. 8.

More specifically, as shown in FIG. 8, the control apparatus 20 first reads treatment instrument information of the high-frequency snare 40 inputted from the treatment instrument ID read sensor 52a and stored in the treatment instrument ID internal IC chip 49 at the treatment detection portion 20a. The treatment instrument information is inputted from the treatment detection portion 20a to the control portion 20b (S21). At this point, in the case where the treatment instrument is the high-frequency snare 40, the control portion 20b of the control apparatus 20 performs control in accordance with the respective steps of the flowchart shown in FIG. 8.

Then, based on the advance/retreat displacement position of the slider 46 of the handle portion 44 obtained from the detected signal of the slide detection sensor 53b in the retaining box 53, the control portion 20b judges whether the treatment portion 41 of the high-frequency snare 40 is in the open state (S22).

At this point, when the control portion 20b judges that the treatment portion 41 is in a closed state, the control portion 20b switches to a normal mode (S23).

In this case, the normal mode refers to a normal advance/retreat mode in which the sheath 42 of the high-frequency snare 40 advances/retreats at a preset, predetermined speed. In other words, a closed state of the treatment portion 41 of the high-frequency snare 40 is simply a state where only an operation to advance/retreat the sheath 42 of the high-frequency snare 40 is performed.

On the other hand, when the control portion 20b judges in step S22 that the treatment portion 41 is in an open state, the control portion 20b judges whether the high frequency power supply 70 is energized (S24). At this point, when the high frequency power supply 70 is in an OFF state, the control portion 20b switches to low-speed mode (S25).

In this case, low-speed mode refers to a low-speed advance/retreat mode in which the sheath 42 of the high-frequency snare 40 advances/retreats at a preset, predetermined speed that is slower than the normal advance/retreat mode. In other words, when the treatment portion 41 is in the open state, the advance/retreat speed of the sheath 42 is set to low speed.

Next, in accordance with each switched mode, the control portion 20b drives the electrical advance/retreat apparatus 60 that is an actuator (S26). More specifically, when a transition is made to step S23, the control portion 20b switches to the normal mode and drives the electrical advance/retreat apparatus 60 in correspondence to a predetermined speed at which the sheath 42 of the high-frequency snare 40 advances/retreats. On the other hand, when a transition is made to step S25, the control portion 20b switches to low-speed mode and drives the electrical advance/retreat apparatus 60 in correspondence to a predetermined speed that is slower than the normal mode at which the sheath 42 of the high-frequency snare 40 advances/retreats.

In addition, when the high frequency power supply 70 is in an ON state in step S24, the control portion 20b switches to stop mode (S27). Then, the control portion 20b stops the electrical advance/retreat apparatus 60 that is an actuator (S28).

In other words, the control portion 20b outputs drive signals or stops output thereof to the motor that rotationally drives the roller 61 of the electrical advance/retreat apparatus 60 according to the respective modes. As a result, according to the ON/OFF state of the high frequency power supply 70, the advance/retreat of the sheath 42 of the high-frequency snare 40 is driven or stopped. Therefore, when an ON signal is inputted from the switch of the controller 30, the control portion 20b drives the high frequency power supply 70 so as to enable constriction and dissection of living body tissue at a high frequency by the treatment portion 41 of the high-frequency snare 40.

Next, during driving of the electrical advance/retreat apparatus 60 according to the respective modes, the control portion 20b judges whether the operation lever 34 of the controller 30 is in an advance/retreat switch OFF state where the operation lever 34 is no longer operated (S29).

In other words, in the same manner as in the above-described first embodiment, a neutral state of the operation lever 34 of the controller 30 where the operation lever 34 is neither tilted forward nor backward is a state where no instruction signals for driving the electrical advance/retreat apparatus 60 are inputted to the control portion 20b. In this state, the control portion 20b judges that the advance/retreat switch is turned OFF. In addition, when the operation lever 34 of the controller 30 is being continuously tilted forward or backwards, the control portion 20b judges that the advance/retreat switch is turned ON.

Furthermore, when the control portion 20b judges that the advance/retreat switch is turned ON, the control portion 20b returns to step S22 to repeat the routine of steps S22 to S28. On the other hand, if the control portion 20b judges that the advance/retreat switch is turned OFF, the control portion 20b judges whether the electrical advance/retreat apparatus 60 that is an actuator is stopped (S30).

In this case, when the electrical advance/retreat apparatus 60 is driven or, in other words, when a drive signal is being outputted to the electrical advance/retreat apparatus 60, the control portion 20b suspends output of the drive signal to the electrical advance/retreat apparatus 60 and stops the electrical advance/retreat apparatus 60 (S31). This stops the advance/retreat of the sheath 42 of the high-frequency snare 40, thereby concluding the control flowchart in FIG. 8.

On the other hand, in step S30, when the electrical advance/retreat apparatus 60 is stopped or, in other words, when a drive signal is not being outputted to the electrical advance/retreat apparatus 60, the control portion 20b concludes the control flowchart shown in FIG. 8 as is.

As a result, in a case where the treatment instrument of the high-frequency snare 40 is used in the endoscopic system 1, if the treatment portion 41 is in a closed state, a polyp may be approached in a speedy manner at a normal displacement speed of the sheath 42.

Additionally, in a state where an advance/retreat operation signal is being inputted from the controller 30, as shown in FIG. 9, the displacement speed of the sheath 42 becomes slower during constriction of a polyp 100 which is an open state of the treatment portion 41 of the high-frequency snare 40.

Furthermore, in a state where an advance/retreat operation signal is being inputted from the controller 30, the displacement of the sheath 42 stops at a predetermined position during polyp dissection upon which high frequency is applied to the treatment portion 41 of the high-frequency snare 40.

Therefore, the endoscopic system 1 of the present embodiment is capable of recreating advance/retreat speeds of the sheath 42 that improve operability in accordance with various operation scenes of the high-frequency snare 40 by merely performing simple operations of the controller 30. As a result, smooth polypectomy and easier treatment are realized.

Moreover, as shown in FIG. 10, the control portion 20b of the control apparatus 20 may perform judgment of the open/closed state of the treatment portion 41 in the above-described step S22 using a pressure sensor 42a provided on the sheath 42 of the high-frequency snare 40.

More specifically, the pressure sensor 42a is disposed on the outer periphery of the distal end portion of the sheath 42. One end of a signal cable, not shown, inserted into the sheath 42 is connected to the pressure sensor 42a. The communication cable has its other end connected to the control apparatus 20, and transfers detected signals from the pressure sensor 42a to the control apparatus 20.

In addition, when the treatment portion 41 of the high-frequency snare 40 is housed in the sheath 42, if the longitudinal length is represented by L, the pressure sensor 42a is set so that the distal end position thereof is distanced by at least L/2 from the distal end of the sheath 42.

The pressure sensor 42a detects the pressure with which the treatment portion 41 presses the inner face of the sheath 42, and outputs the result to the control apparatus 20 via the signal cable. In other words, the control portion 20b of the control apparatus 20 is capable of judging the closed state where the treatment portion 41 is housed in the sheath 42 by the detection of a pressing force of the treatment portion 41 by the pressure sensor 42a.

That is, as shown in FIG. 9, when the operation wire 43 is extended by tension applied to the operation wire 43 during constriction of the polyp 100, the control portion 20b recognizes a closed state even when a judgment based solely on the position of the slider 46 results in an open state of the treatment portion 41.

As a result, by performing judgment based on detected values of the pressure sensor 42a, the control portion 20b is able to judge the closed state of the treatment portion 41 in a stable manner.

Third Modification

Figure 11:
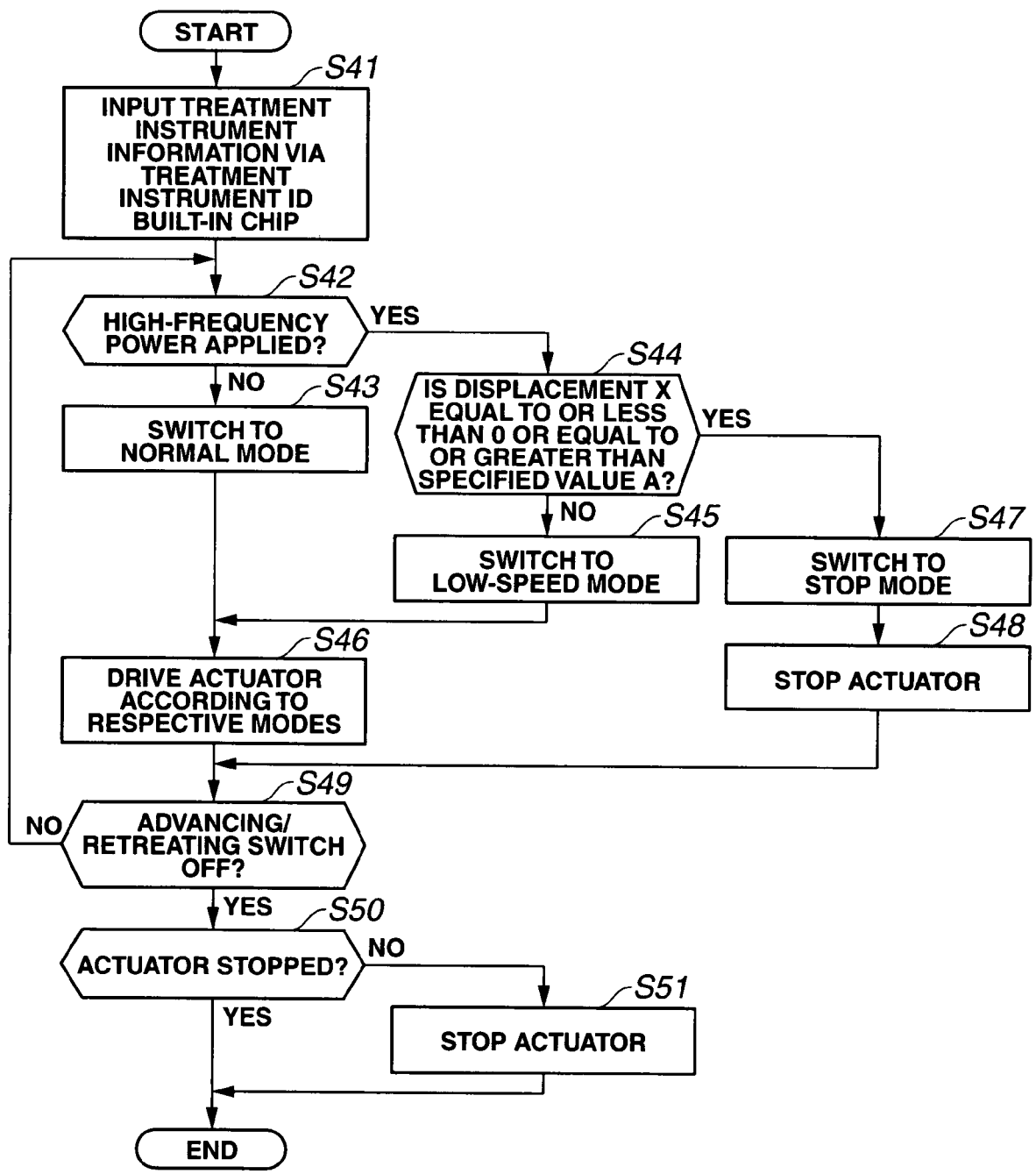
FIG. 11 is a flowchart illustrating control performed by a control apparatus of an endoscopic system according to a third modification of the first embodiment.

Next, a third modification of the present embodiment will be described below with reference to FIGS. 2 and 11. Moreover, for the present modification, the treatment instrument used in the endoscopic system 1 is a high-frequency knife 40 (refer to FIG. 2) in a manner similar to the above-described first embodiment, and the present modification is an example of control performed by the control portion 20b of the control apparatus 20. Therefore, the various configurations of the above-described endoscopic system 1 are represented by like reference characters and descriptions thereof will be omitted. Only different configurations and effects will be described. Moreover, FIG. 11 is a third modification of the first embodiment, and shows a flowchart illustrating control performed by the control apparatus of the endoscopic system.

The present example is a control example in which the displacement of the sheath 42 of the high-frequency knife 40 is regulated by the control apparatus 20 of the endoscopic system 1.

First, a specified value (A) for regulating the displacement (X) by which the sheath 42 of the high-frequency knife 40 projects from the insertion portion 14 of the endoscope 10 during energization to the treatment portion 41 may be arbitrarily registered to the treatment storage portion 20c that is built into the control apparatus 20 according to the present embodiment. In other words, a user may register to the control apparatus 20, in advance, an arbitrarily specified value (A) of the length by which the sheath 42 of the high-frequency knife 40 to be used projects from the distal end portion 11 of the endoscope 10.

In addition, when the endoscope 10 is connected, the control apparatus 20 reads a channel length and the like of the treatment instrument insertion channel 14a disposed in the insertion portion 14 of the connected endoscope 10 from the endoscope ID internal IC chip 26 built into the connector 25, and stores the length in the treatment storage portion 20c. Then, the control apparatus 20 recognizes the position at which the sheath 42 of the high-frequency knife 40 reaches the distal end aperture 11a of the treatment instrument insertion channel 14a of the distal end portion 11 of the endoscope 10 as 0 (zero).

In other words, the control apparatus 20 calculates a position at which the sheath 42 of the high-frequency knife 40 is advanced and inserted into the treatment instrument insertion channel 14a by the electrical advance/retreat apparatus 60, and reaches the distal end aperture 11a of the distal end portion 11, and sets that position to 0 (zero).

Then, based on the registered and set arbitrary specified value (A) and the position 0 (zero), the control portion 20b of the control apparatus 20 executes a control example such as shown in FIG. 11. Similarly, in this case, a drive instruction signal from the operation lever 34 of the controller 30 acts as a trigger and causes the control apparatus 20 to perform control based on the routine (steps) of the flowchart shown in FIG. 11.

More specifically, as shown in FIG. 11, the control apparatus 20 first reads treatment instrument information of the high-frequency knife 40 inputted from the treatment instrument ID read sensor 52a and stored in the treatment instrument ID internal IC chip 49 at the treatment detection portion 20a. The treatment instrument information is inputted from the treatment detection portion 20a to the control portion 20b (S41). At this point, in the case where the treatment instrument is the high-frequency knife 40, the control portion 20b of the control apparatus 20 performs control in accordance with the respective steps of the flowchart shown in FIG. 11.

Then, the control portion 20b of the control apparatus 20 judges whether the high frequency power supply 70 is energized (S42). At this point, when the high frequency power supply 70 is in an OFF state, the control portion 20b switches to the normal mode (S43).

On the other hand, when the high frequency power supply 70 is in an ON state, the control portion 20b judges whether the advance/retreat displacement X of the sheath 42 of the high-frequency knife 40 is not greater than 0 (zero), and whether the advance/retreat displacement X is equal to or greater than a specified value A (X≧A) registered in advance in the treatment storage portion 20c (S44). Moreover, for this judgment, the control portion 20b compares the advance/retreat displacement X of the sheath 42 of the high-frequency knife 40 that is calculated by the treatment detection portion 20a based on detected signals from the rotation detection sensor 62 built into the electrical advance/retreat apparatus 60 with a specified value A that is registered in the treatment storage portion 20c.

When the displacement X of the high-frequency knife 40 is not position 0 (zero) and is less than the specified value A, the control portion 20b switches to low-speed mode (S45).

As seen, in accordance with the respective modes including the normal mode and the low-speed mode, the control portion 20b drives the electrical advance/retreat apparatus 60 that is an actuator (S46). More specifically, when a transition is made to step S43, the control portion 20b switches to the normal mode and drives the electrical advance/retreat apparatus 60 in correspondence to a predetermined speed at which the sheath 42 of the high-frequency knife 40 advances/retreats. On the other hand, when a transition is made to step S45, the control portion 20b switches to low-speed mode and drives the electrical advance/retreat apparatus 60 in correspondence to a predetermined speed that is slower than the normal mode at which the sheath 42 of the high-frequency knife 40 advances/retreats. Subsequently, the control portion 20b makes a transition to step S49, which will be described later.

In addition, when the displacement X of the sheath 42 of the high-frequency knife 40 is not greater than 0 (zero) or is equal to or more than the specified value A in step S44, the control portion 20b switches to stop mode (S47). Furthermore, the control portion 20b stops power supply to the electrical advance/retreat apparatus 60 that is an actuator even if an advance/retreat drive instruction signal is inputted from the controller 30, and stops the advance/retreat of the sheath 42 of the high-frequency knife 40 (548). Subsequently, the control portion 20b makes a transition to step S49.

Moreover, at this point, when the displacement X of the sheath 42 of the high-frequency knife 40 is at a position that is smaller than 0 (zero) or, in other words, when the treatment portion 41 is at a position to be housed in the treatment instrument insertion channel 14a, the control portion 20b is arranged to either turn high-frequency energization OFF, or to stop power supply to the electrical advance/retreat apparatus 60.

Then, in step S49, during driving of the electrical advance/retreat apparatus 60 according to the respective modes, the control portion 20b judges whether the operation lever 34 of the controller 30 is in an advance/retreat switch OFF state where the operation lever 34 is no longer operated (S49).

At this point, when the control portion 20b judges that the advance/retreat switch is turned ON, the control portion 20b returns to step S42 to repeat the routine of steps S42 to S48. On the other hand, if the control portion 20b judges that the advance/retreat switch is turned OFF, the control portion 20b judges whether the electrical advance/retreat apparatus 60 that is an actuator is stopped (S50).

In this case, when the electrical advance/retreat apparatus 60 is driven or, in other words, when a drive signal is being outputted to the electrical advance/retreat apparatus 60, the control portion 20b suspends output of the drive signal to the electrical advance/retreat apparatus 60 and stops the electrical advance/retreat apparatus 60 (S51). This stops the advance/retreat of the sheath 42 of the high-frequency knife 40, thereby concluding the control flowchart in FIG. 11.

On the other hand, in step S50, when the electrical advance/retreat apparatus 60 is stopped or, in other words, when a drive signal is not being outputted to the electrical advance/retreat apparatus 60, the control portion 20b concludes the control flowchart shown in FIG. 11 as is.

As a result, in a case where the treatment instrument of the high-frequency knife 40 is used in the present modification, the endoscopic system 1 advances/retreats the sheath 42 at low-speed mode during treatment of living body tissue upon which a high-frequency current is applied to the treatment portion 41 when the displacement X of the sheath 42 projected from the insertion portion 14 of the endoscope 10 is more than 0 (zero) and lower than a set specified value A.

In addition, during treatment of living body tissue upon which a high-frequency current is applied to the treatment portion 41, when the displacement X of the sheath 42 projected from the insertion portion 14 of the endoscope 10 is equal to or greater than the specified value A, the endoscopic system I switches to stop mode and stops the advance/retreat of the sheath 42.

As a result, since the endoscopic system 1 does not advance the sheath 42 beyond a preset specified value A even if an inadvertent operation of the controller 30 is performed when a high-frequency current is being applied to the treatment portion 41, a configuration is realized that enables a position of dissection of living body tissue using the high-frequency knife 40 to be set at intended positions. In addition, since the endoscopic system 1 controls the sheath 42 of the high-frequency knife 40 to prevent the sheath 42 from being housed into the treatment instrument insertion channel 14a of the endoscope 10 when a high-frequency current is being applied to the treatment portion 41, damages to the treatment instrument insertion channel 14a due to high frequency may be prevented.

Second Embodiment

Figure 12:
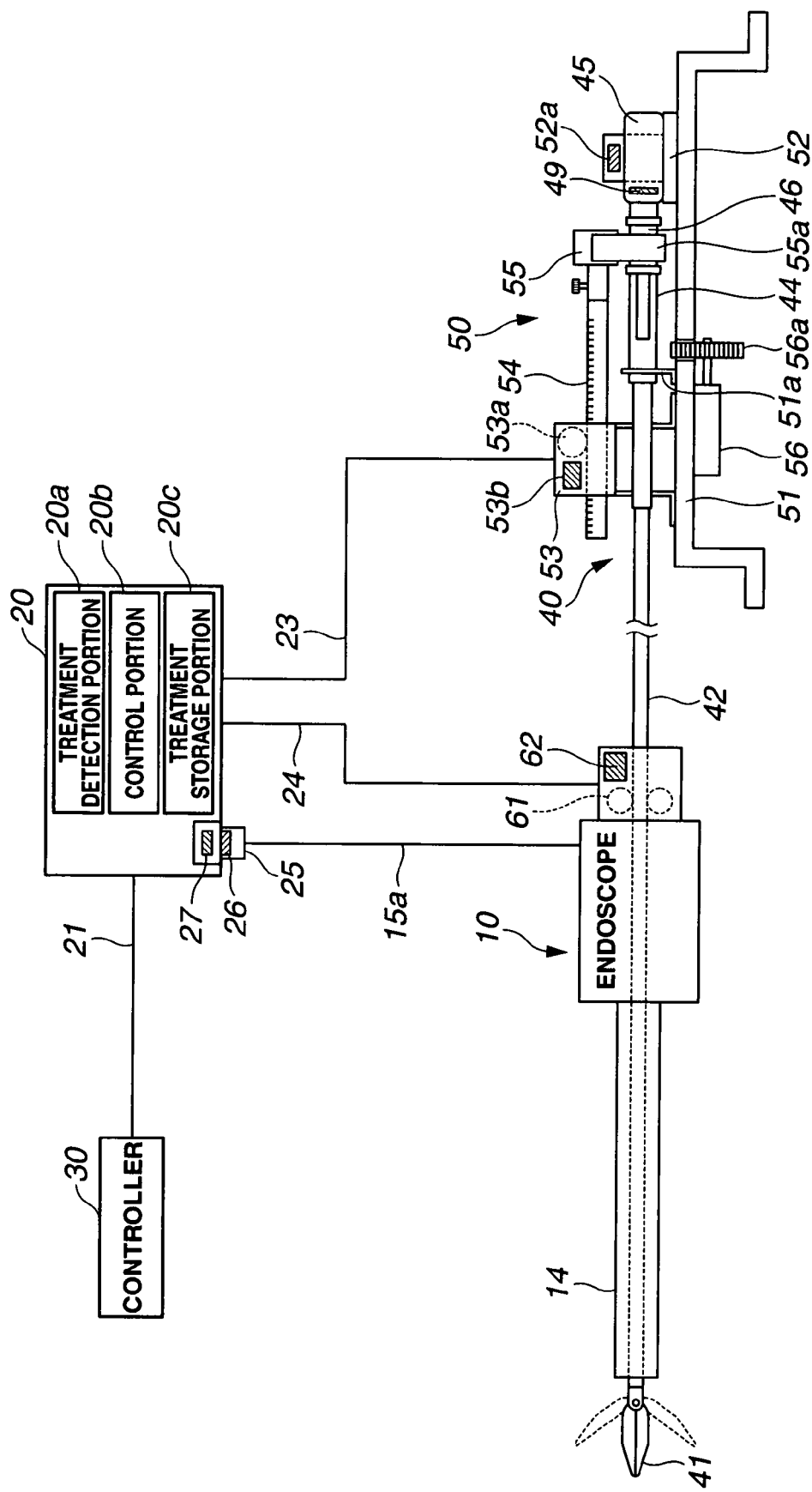
FIG. 12 is a diagram including a block display of a configuration of an endoscopic system according to a second embodiment of the present invention to which grasping forceps have been set.
Figure 13:
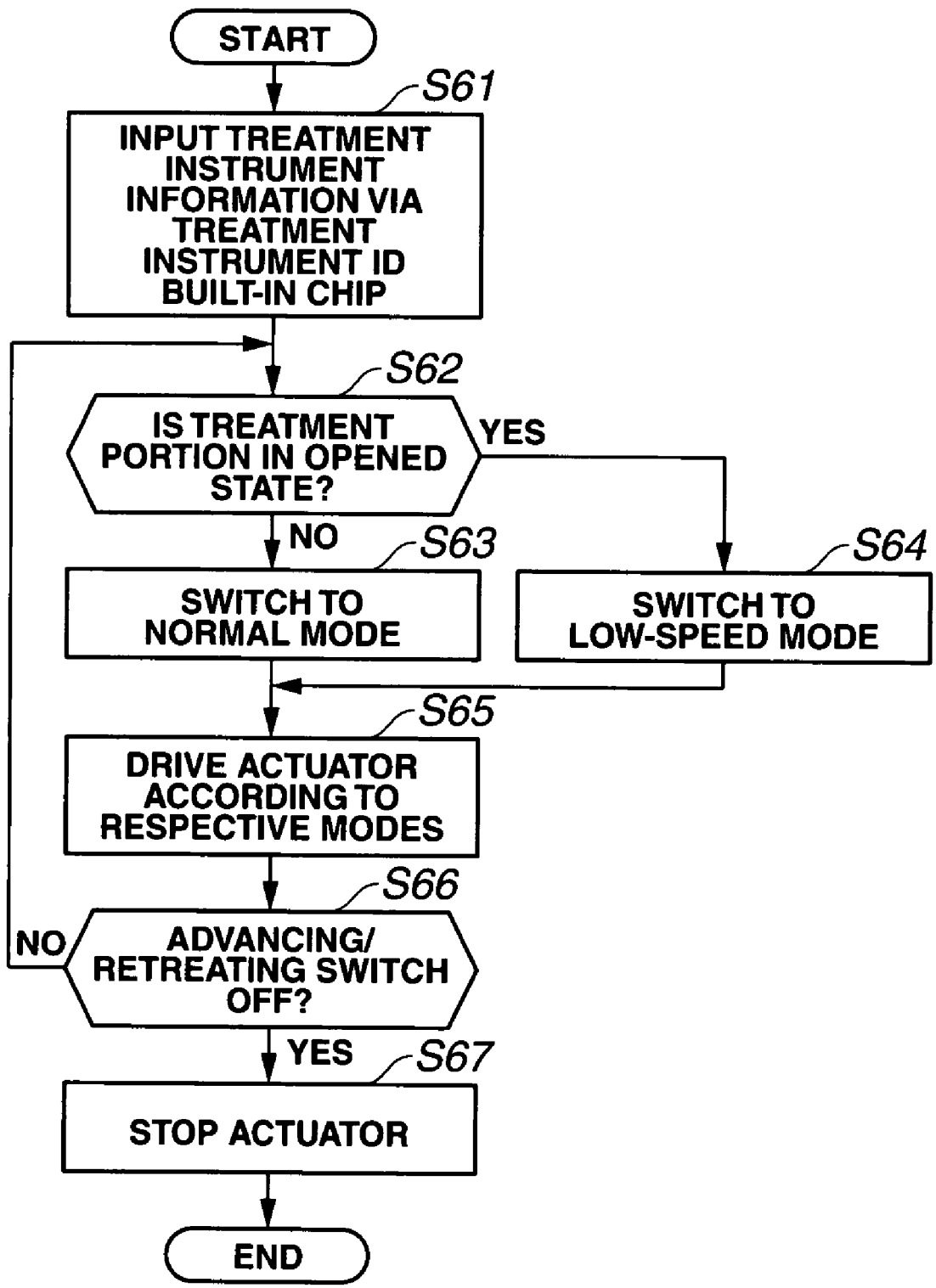
FIG. 13 is a flowchart illustrating control performed by a control apparatus of the endoscopic system shown in FIG. 12.

Next, a second embodiment of the present invention will be described below with reference to FIGS. 12 and 13. Moreover, FIGS. 12 and 13 show the second embodiment of the present invention, in which: FIG. 12 is a diagram including a block display of a configuration of an endoscopic system to which grasping forceps have been set; while FIG. 13 is a flowchart illustrating control performed by the control apparatus of the endoscopic system shown in FIG. 12.

A treatment instrument that does not perform treatment using high frequency power is used in the endoscopic system 1 according to the present embodiment, and a case will be described where, for example, grasping forceps (hereinafter described as the grasping forceps 40) are used. Moreover, as well known, the grasping forceps 40 are configured such that a cup-like treatment portion 41 opens/closes in accordance with advance/retreat operations of a slider 46.

Furthermore, since the grasping forceps 40 according to the present embodiment are not treatment instruments that use high-frequency, a high frequency power supply 70 is not shown in FIG. 12.

Moreover, in the present embodiment, since the treatment instruments 40 that are used in the endoscopic system 1 are the grasping forceps 40, like reference characters will be used for the various configurations of the above-described endoscopic system 1 and descriptions thereof will be omitted. Only different configurations and effects shall be described.

Meanwhile, the open/closed state of the treatment portion 41 of the grasping forceps 40 is varied by the pulling/relaxing of the operation wire (having a similar configuration as the high-frequency snare presented in the second modification of the first embodiment) inserted into the sheath 42. In other words, the grasping forceps 40 is configured so that the cup-like treatment portion 41 is opened/closed by forward and backward advance/retreat operations of the slider 46 of the handle portion 44.

As seen, during advance/retreat operations of the grasping forceps 40, the endoscopic system 1 according to the present embodiment to which the grasping forceps are installed executes the control example illustrated by the flowchart of FIG. 13 using the control apparatus 20. Similarly, in this case, a drive instruction signal from the operation lever 34 of the controller 30 acts as a trigger and causes the control apparatus 20 to perform control based on the routine (steps) of the flowchart shown in FIG. 13.

In addition, as represented by the respective steps of the flowchart shown in FIG. 13, the present embodiment is a control example in which only the judgment performed in step S62 differs from that of the first embodiment. In other words, while the control apparatus 20 judges whether a high-frequency current is being applied to the treatment portion 41 in step S2 of the first embodiment, in step S62 of the present embodiment, the control apparatus 20 judges the open/closed state of the treatment portion 41 and performs control in accordance with the state.

Therefore, since the control apparatus 20 of the endoscopic system 1 performs in step S61 and steps S63 to S67 shown in FIG. 13 the same controls as those in step S1 and steps S3 to S7 of the first embodiment shown in FIG. 3, descriptions on such controls shall be omitted from the following description for the sake of simplicity.

First, when treatment instrument information informing that the treatment instrument to be used in step S61 are grasping forceps 40 is inputted (S61), the control portion 20b of the control apparatus 20 judges whether the treatment portion 41 of the grasping forceps 40 is in an open state (S62). For this judgment, the control portion 20b judges the open/closed state of the treatment portion 41 of the grasping forceps 40 by the advance/retreat displacement position of the slider 46 of the handle portion 44 from detected signals of the slide detection sensor 53b of the retaining box 53.

Then, when the control portion 20b judges that the treatment portion 41 of the grasping forceps 40 is not an open state and is a closed state instead, the control portion 20b switches the advance/retreat speed of the sheath 42 to a normal mode that is a normal speed (S63). On the other hand, when the control portion 20b judges that the treatment portion 41 of the grasping forceps 40 is in an open state, the control portion 20b switches the advance/retreat speed of the sheath 42 to a low-speed mode that is a predetermined speed slower than the normal mode (S64).

Next, in accordance with each switched mode, the control portion 20b drives the electrical advance/retreat apparatus 60 that is an actuator (S65). More specifically, when a transition is made to step S63, the control portion 20b switches to the normal mode and drives the electrical advance/retreat apparatus 60 in correspondence to a predetermined speed at which the sheath 42 of the grasping forceps 40 advances/retreats. On the other hand, when a transition is made to step S64, the control portion 20b switches to low-speed mode and drives the electrical advance/retreat apparatus 60 in correspondence to a predetermined speed that is slower than the normal mode at which the sheath 42 of the grasping forceps 40 advances/retreats.

In other words, the control portion 20b variably outputs voltage to the motor that rotationally drives the roller 61 of the electrical advance/retreat apparatus 60 according to preset rotary speeds of the respective modes. As a result, the advance/retreat speed of the sheath 42 of the grasping forceps 40 varies according to the open/closed state of the grasping forceps 40.

As a result, in the endoscopic system 1 according to the present embodiment, since the sheath 42 advances/retreats at a low speed in an open state of the treatment portion 41 of the grasping forceps 40, approachability to living body tissue that is the object treatment area may be improved. In addition, since the endoscopic system 1 ensures that the sheath 42 is not advanced/retreated at a relatively high normal speed in an open state of the treatment portion 41 of the grasping forceps 40, inadvertent retracting of the treatment portion 41 by the operator during housing to the treatment instrument insertion channel 14a of the insertion portion 14 of the endoscope 10 may be prevented. As a result, the endoscopic system 1 according to the present embodiment is capable of preventing damage to the insertion portion 14 and the treatment instrument insertion channel 14a by the treatment portion 41 of the grasping forceps 40.

Third Embodiment

Figure 14:
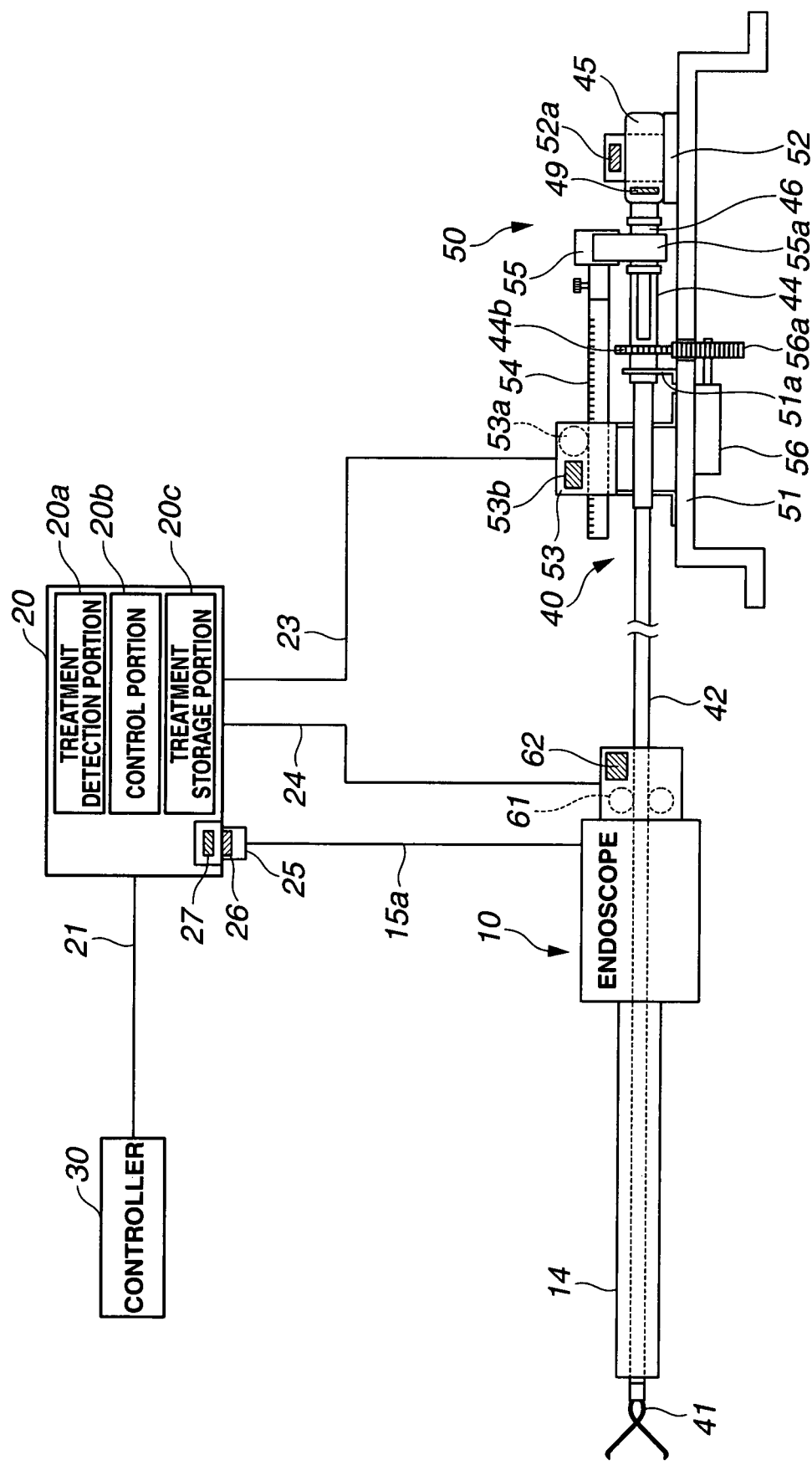
FIG. 14 is a diagram including a block display of a configuration of an endoscopic system according to a third embodiment of the present invention to which a rotating clip apparatus has been set.
Figure 15:
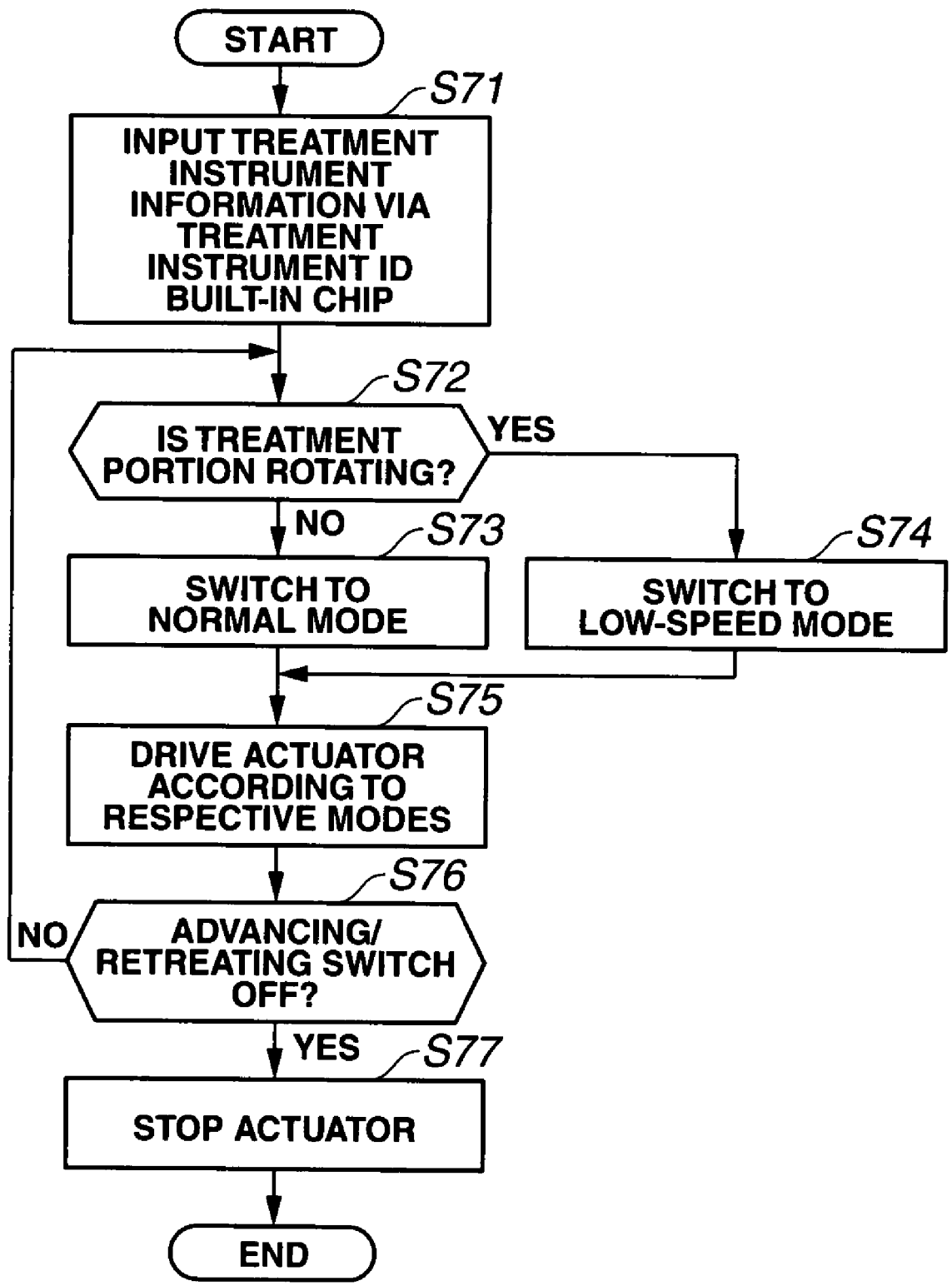
FIG. 15 is a flowchart illustrating control performed by a control apparatus of the endoscopic system shown in FIG. 14.

Next, a third embodiment of the present invention will be described below with reference to FIGS. 14 and 15. Moreover, FIGS. 14 and 15 show the third embodiment of the present invention, in which: FIG. 14 is a diagram including a block display of a configuration of an endoscopic system to which a rotating clip apparatus has been set; while FIG. 15 is a flowchart illustrating control performed by a control apparatus of the endoscopic system shown in FIG. 14.

A treatment instrument that does not perform treatment using high frequency power is also used in the endoscopic system 1 according to the present embodiment, and a case will be described where, for example, a rotating clip apparatus (hereinafter described as the rotating clip apparatus 40) that is a treatment apparatus is used. Moreover, as well known, the rotating clip apparatus 40 is configured so that a treatment portion 41 that is a surgical hemostatic clip rotates, and mucosa and blood vessels in a living body are mechanically grasped or constricted by the treatment portion 41.

In addition, a spur gear 44b is disposed on the handle portion 44 of the rotating clip apparatus 40. When the handle portion 44 of the rotating clip apparatus 40 is disposed on the treatment instrument electrical operation apparatus 50, the gear 44b meshes with the gear 56a of the motor 56 provided on a rear face side of the base body 51 of the treatment instrument electrical operation apparatus 50.

In other words, during driving of the motor 56, the treatment instrument electrical operation apparatus 50 transfers the rotation of the gear 56a to the gear 44b of the rotating clip apparatus 40. As a result, the endoscopic system 1 according to the present embodiment is configured so that the treatment portion 41 of the rotating clip apparatus 40 rotates together with the sheath 42.

In addition, since the rotating clip apparatus 40 according to the present embodiment is also a treatment instrument that does not use high-frequency, a high frequency power supply 70 is not shown in FIG. 15.

Moreover, since the only difference of the present embodiment is that the treatment instrument 40 to be used in the endoscopic system 1 is the rotating clip apparatus 40, like reference characters will be used for the various configurations of the endoscopic system 1 according to the respective embodiments described above, and descriptions thereof will be omitted. Only different configurations and effects shall be described.

As seen, during advance/retreat operations of the rotating clip apparatus 40, the endoscopic system 1 according to the present embodiment to which the rotating clip apparatus is installed executes the control example illustrated by the flowchart of FIG. 15 using the control apparatus 20. Similarly, in this case, a drive instruction signal from the operation lever 34 of the controller 30 acts as a trigger and causes the control apparatus 20 to perform control based on the routine (steps) of the flowchart shown in FIG. 15.

In addition, as represented by the respective steps of the flowchart shown in FIG. 15, the present embodiment is also a control example in which only the judgment performed in step S72 differs from that of the first embodiment. In other words, while the control apparatus 20 judges whether a high-frequency current is being applied to the treatment portion 41 in step S2 of the first embodiment, in the present embodiment, the control apparatus 20 judges in step S72 the rotating state of the treatment instrument 41 and performs control in accordance with the state.

Therefore, since the control apparatus 20 of the endoscopic system 1 performs in step S71 and steps S73 to S77 shown in FIG. 15 the same controls as those in step S1 and steps S3 to S7 of the first embodiment shown in FIG. 3, descriptions on such controls shall be omitted from the following description for the sake of simplicity.

First, when treatment instrument information informing that the treatment instrument to be used in step S71 is a rotating clip apparatus is inputted (S71), the control portion 20b of the control apparatus 20 judges whether the treatment portion 41 of the rotating clip apparatus 40 is in rotation (S72). For this judgment, the control portion 20b judges whether the treatment portion 41 of the rotating clip apparatus 40 is in a rotating state based on the energization state of drive power to the motor 56 provided in the treatment instrument electrical operation apparatus 50.

Then, when the control portion 20b judges that the treatment portion 41 of the rotating clip apparatus 40 is in a non-rotating state, the control portion 20b switches the advance/retreat speed of the sheath 42 to a normal mode that is a normal speed (S73). On the other hand, when the control portion 20b judges that the treatment portion 41 of the rotating clip apparatus 40 is in a rotating state, the control portion 20b switches the advance/retreat speed of the sheath 42 to a low-speed mode that is a predetermined speed slower than the normal mode (S74).

Next, in accordance with each switched mode, the control portion 20b drives the electrical advance/retreat apparatus 60 that is an actuator (S75). More specifically, when a transition is made to step S73, the control portion 20b switches to the normal mode and drives the electrical advance/retreat apparatus 60 in correspondence to a predetermined speed at which the sheath 42 of the rotating clip apparatus 40 advances/retreats. On the other hand, when a transition is made to step S74, the control portion 20b switches to low-speed mode and drives the electrical advance/retreat apparatus 60 in correspondence to a predetermined speed that is slower than the normal mode at which the sheath 42 of the rotating clip apparatus 40 advances/retreats.

In other words, the control portion 20b variably outputs voltage to the motor that rotationally drives the roller 61 of the electrical advance/retreat apparatus 60 according to preset rotary speeds of the respective modes. As a result, the advance/retreat speed of the sheath 42 of the rotating clip apparatus 40 varies according to the rotating state of the rotating clip apparatus 40.

As a result, in the endoscopic system 1 according to the present embodiment, since the sheath 42 advances/retreats at a low speed when the treatment portion 41 of the rotating clip apparatus 40 is in a rotating state, approachability to a mucosal tissue that is the object treatment area or a blood vessel on which hemostasis is to be performed may be improved.

Fourth Embodiment

Figure 16:
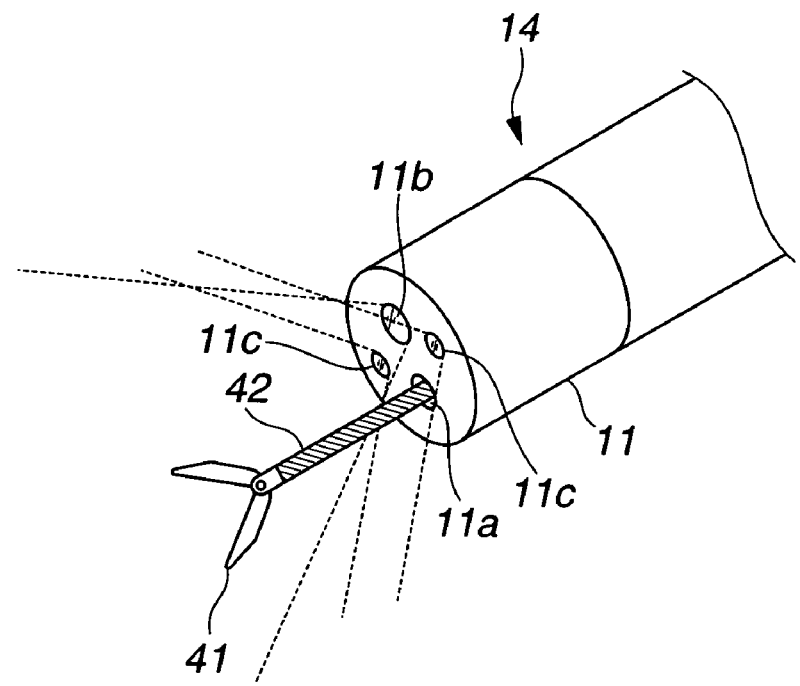
FIG. 16 is a perspective view according to a fourth embodiment of the present invention showing a state where grasping forceps project from the distal end portion of an endoscope.
Figure 17:
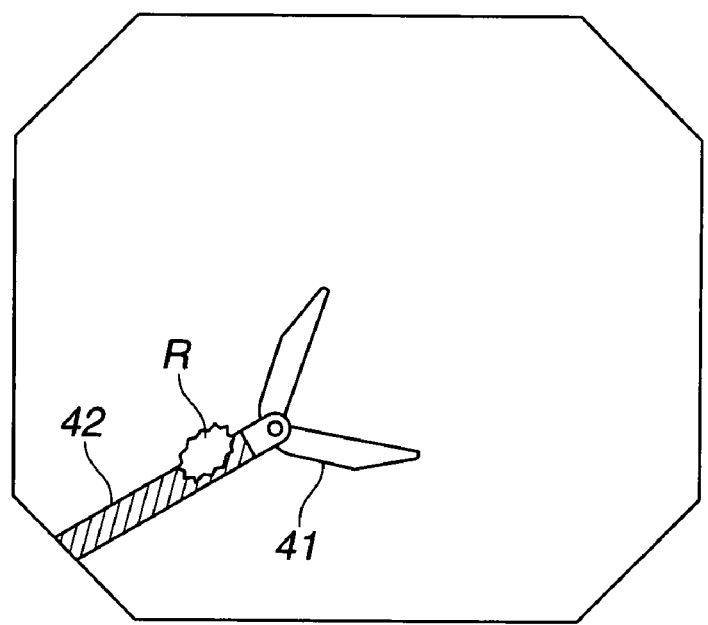
FIG. 17 is a diagram showing a display on a monitor screen corresponding to FIG. 16.
Figure 18:
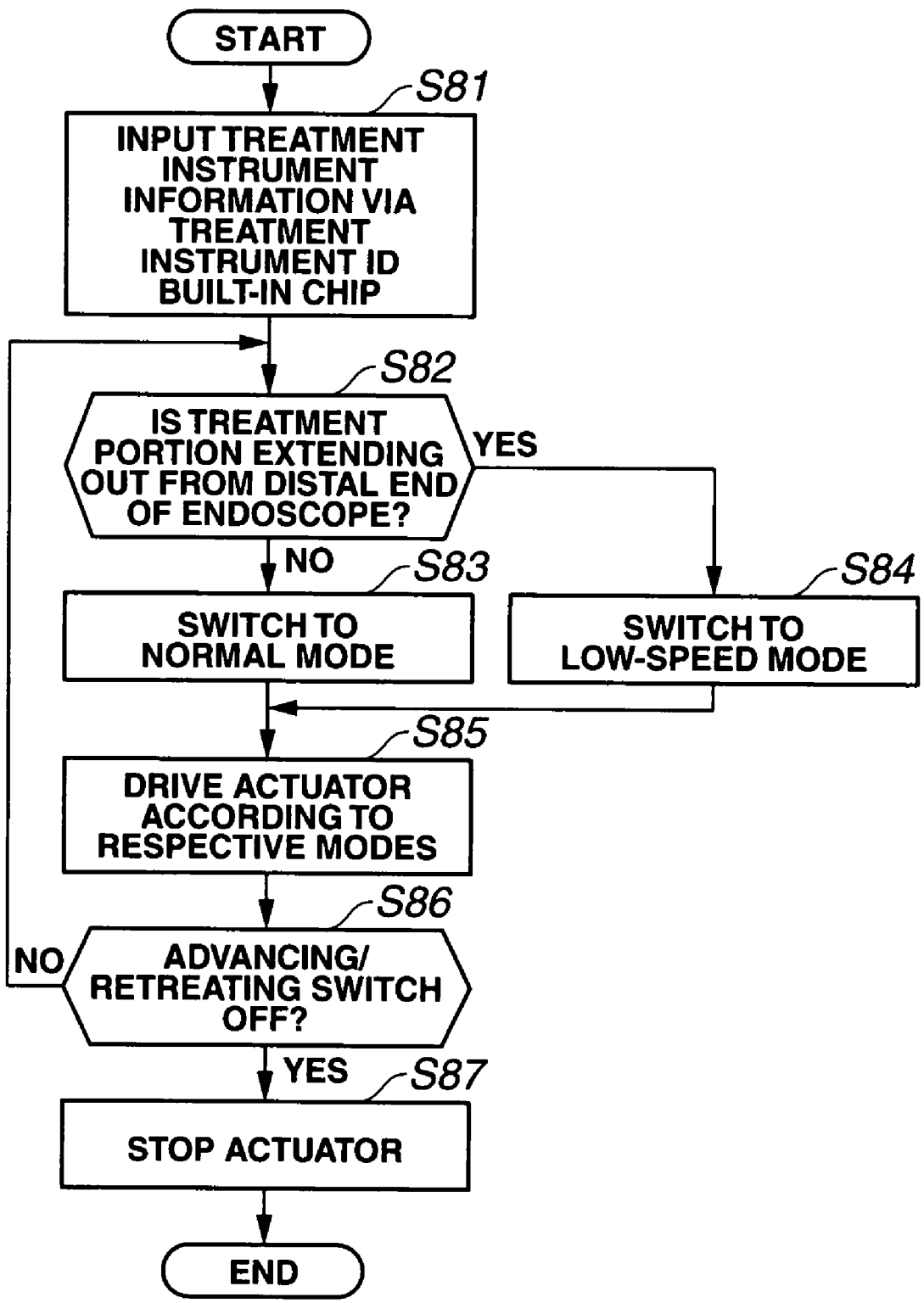
FIG. 18 is a flowchart illustrating control performed by a control apparatus of an endoscopic system.

Next, a fourth embodiment of the present invention will be described below with reference to FIGS. 16 to 18. FIGS. 16 and 17 show the fourth embodiment of the present invention, in which: FIG. 16 is a perspective view showing a state where grasping forceps project from the distal end portion of an endoscope; FIG. 17 is a diagram showing a display on a monitor screen in the state shown in FIG. 16; and FIG. 18 is a flowchart illustrating control performed by the control apparatus of an endoscopic system.

An endoscopic system 1 according to the present embodiment is an embodiment that utilizes functions normally included in conventional endoscopic apparatuses. More specifically, the control apparatus 20 that is a CCU is provided with a function for recognizing luminescent points of reflected light in endoscopic images from the endoscope 10 as conditions of light modulation.

For example, as shown in FIG. 16, in a state where the treatment instrument, which, in this case, is the grasping forceps 40, projects from the distal end portion 11 of the insertion portion 14 of the endoscope 10, the endoscopic image shows a luminescent point R that is illuminating light reflecting off the sheath 42 of the grasping forceps 40 or the like, as shown in FIG. 17. Incidentally, reference character 11b in FIG. 16 denotes an image pickup window while reference character 11c denotes an illumination window.

Light modulation performed by the control apparatus 20 on the image using the luminescent point R as a reference results in excessively darkening the periphery of the luminescent point R. Therefore, the control apparatus 20 recognizes the luminescent point R on the image and exempts the luminescent point R from the conditions of light modulation control. In other words, this light modulation control is a function that is also included in conventional endoscopic apparatuses. Thus, the present embodiment is a control example in which control is performed using this light modulation function.

Moreover, while a case where, for instance, grasping forceps (hereinafter described as the grasping forceps 40) is used will be described for the endoscopic system 1 according to the present embodiment, it is obvious that the present embodiment is applicable to any kind of treatment instrument.

As seen, during advance/retreat operations of the grasping forceps 40, the endoscopic system 1 according to the present embodiment to which the grasping forceps 40 are installed executes the control example illustrated by the flowchart of FIG. 18 using the control apparatus 20. Similarly, in this case, a drive instruction signal from the operation lever 34 of the controller 30 acts as a trigger and causes the control apparatus 20 to perform control based on the routine (steps) of the flowchart shown in FIG. 18.

In addition, as represented by the respective steps of the flowchart shown in FIG. 18, the present embodiment is also a control example in which only the judgment performed in step S82 differs from that of the first embodiment. In other words, while the control apparatus 20 according to the first embodiment judges whether a high-frequency current is being applied to the treatment portion 41 in step S2, in the present embodiment, the control apparatus 20 performs control by judging in step S82 the luminescent point R reflecting off the treatment instrument 40 and judging whether the treatment instrument 40 projects from the distal end portion 11 of the endoscope 10.

Therefore, since the control apparatus 20 of the endoscopic system 1 performs in step S81 and steps S83 to S87 shown in FIG. 18 the same controls as those in step S1 and steps S3 to S7 of the first embodiment shown in FIG. 3, descriptions on such controls shall be omitted from the following description for the sake of simplicity.

First, when treatment instrument information informing that the treatment instrument to be used in step S81 are grasping forceps is inputted (S81), the control portion 20b of the control apparatus 20 judges whether the treatment portion 41 of the grasping forceps 40 is projecting from the distal end portion 11 of the endoscope 10 (S82). For this judgment, as described above, the control portion 20b judges whether the treatment portion 41 of the grasping forceps 40 projects from the distal end portion 11 of the endoscope 10 according to the recognition of a luminescent point reflecting off the sheath 42 and the like. Moreover, since the control apparatus 20 according to the present embodiment is capable of controlling any kind of treatment instrument, the inputting of treatment instrument information of step S81 need not be particularly performed.

Then, when the control portion 20b judges that the grasping forceps 40 are in a non-projection state with respect to the distal end portion 11 of the endoscope 10, the control portion 20b switches the advance/retreat speed of the sheath 42 to a normal mode that is a normal speed (S83). On the other hand, when the control portion 20b judges that the grasping forceps 40 project from the distal end portion 11 of the endoscope 10, the control portion 20b switches the advance/retreat speed of the sheath 42 to a low-speed mode that is a predetermined speed slower than the normal mode (S84).

Next, in accordance with each switched mode, the control portion 20b drives the electrical advance/retreat apparatus 60 that is an actuator (S85). More specifically, when a transition is made to step S83, the control portion 20b switches to the normal mode and drives the electrical advance/retreat apparatus 60 in correspondence to a predetermined speed at which the sheath 42 of the grasping forceps 40 advances/retreats. On the other hand, when a transition is made to step S84, the control portion 20b switches to low-speed mode and drives the electrical advance/retreat apparatus 60 in correspondence to a predetermined speed that is slower than the normal mode at which the sheath 42 of the grasping forceps 40 advances/retreats.

In other words, the control portion 20b variably outputs voltage to the motor that rotationally drives the roller 61 of the electrical advance/retreat apparatus 60 according to preset rotary speeds of the respective modes. As a result, the advance/retreat speed of the sheath 42 varies depending on whether the grasping forceps 40 are in a treatment state where the grasping forceps 40 projects from the distal end portion 11 or a non-treatment state where the grasping forceps 40 are housed in the insertion portion 14.

As seen, with the endoscopic system 1 according to the present embodiment, the sheath 42 advances/retreats at a relatively high speed until the grasping forceps 40 project from the distal end portion 11 of the endoscope 10, and advances/retreats at a low speed once the grasping forceps 40 project from the distal end portion 11 of the endoscope 10. In other words, with the endoscopic system 1 according to the present embodiment, the grasping forceps 40 advances/retreats at a low speed once the grasping forceps 40 project from the distal end portion 11 of the endoscope 10 even in a case where slippage occurs between the sheath 42 of the grasping forceps 40 and the roller 61 of the electrical advance/retreat apparatus 60 or in a case where the insertion portion 14 of the endoscope 10 is bended in a complicated fashion.

As a result, with the endoscopic system 1 according to the present embodiment, when various treatment instruments, which was described above using grasping forceps as an example, are in a non-treatment mode that is a state where the treatment instruments are housed in the insertion portion 14 of the endoscope 10, the used treatment instrument 40 moves in a normal, relatively high advance/retreat speed and the time required for feeding out and retracting may be reduced. On the other hand, in a treatment state where the various treatment instruments 40 project from the distal end portion 11 of the endoscope 10, since the used treatment instrument 40 moves slower than the normal advance/retreat speed, approachability to treatment areas in the body cavity may be improved.

Fifth Embodiment

Figure 19:
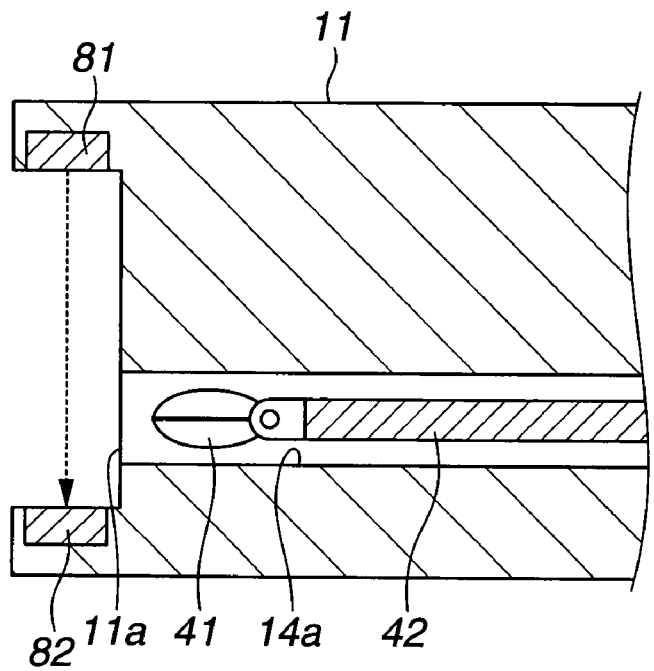
FIG. 19 is a cross sectional diagram according to a fifth embodiment of the present invention showing a state where grasping forceps are housed in a treatment instrument insertion channel.
Figure 20:
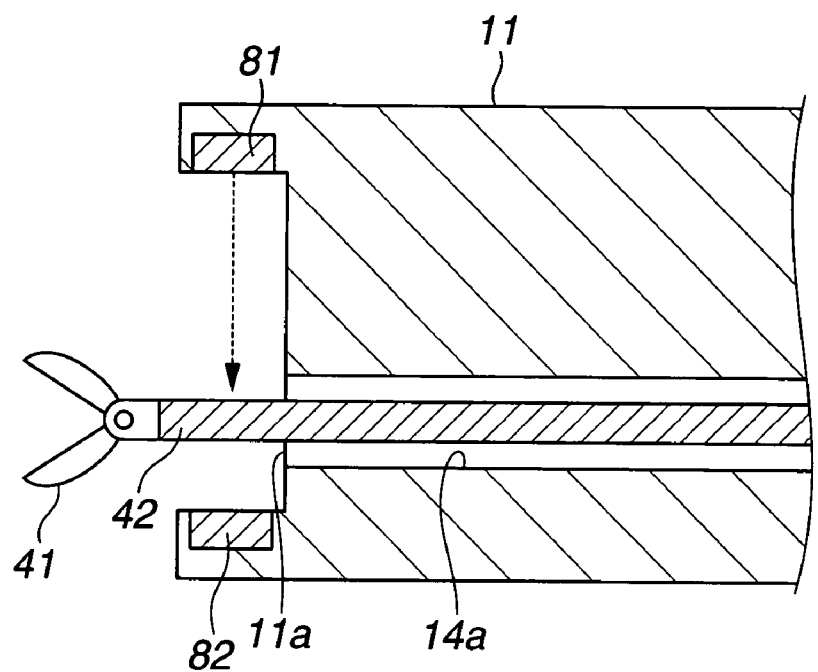
FIG. 20 is a cross sectional diagram showing a distal end portion of an endoscope having an optical sensor and showing a state where grasping forceps project from the distal end portion.

Next, a fifth embodiment of the present invention will be described below with reference to FIGS. 19 and 20. FIGS. 19 and 20 show the fifth embodiment of the present invention, in which: FIG. 19 is a cross sectional diagram showing a distal end portion of an endoscope provided with an optical sensor and which shows a state where grasping forceps are housed in a treatment instrument insertion channel; and FIG. 20 is a cross sectional diagram showing a distal end of an endoscope provided with an optical sensor and showing a state where grasping forceps project from the distal end.

Among the controls performed by the control apparatus 20 of the endoscopic system 1 described with respect to the fourth embodiment, the endoscopic system 1 according to the present embodiment differs in the configuration of the sensor that judges in step S82 whether the treatment portion 41 of the grasping forceps 40 projects from the distal end portion 11 of the endoscope 10 as shown in FIG. 18. Accordingly, since the present embodiment executes the control example shown in FIG. 18 that is performed by the control apparatus 20 in the fourth embodiment, detailed descriptions of the configurations and effects will be omitted. Only different portions shall be described below.

To elaborate, as shown in FIG. 19, the distal end portion 11 of the insertion portion 14 of the endoscope 10 according to the present embodiment is provided with an optical sensor comprising: a light emitting portion 81; and a light receiving portion 82 that receives and detects light from the light emitting portion 81. The light emitting portion 81 and the light receiving portion 82 are provided on the distal end portion 11 on a section protruding from the distal end face thereof, and are electrically connected to the control apparatus 20 via a signal cable, not shown, inserted into the insertion portion 14 of the endoscope 10. Moreover, the optical sensor comprising the light emitting portion 81 and the light receiving portion 82 may be configured to be detachable with respect to the distal end portion 11.

The endoscopic system 1 according to the present embodiment performs the judgment (S82) by the control portion 20b of the control apparatus 20 on whether the treatment portion 41 of the grasping forceps 40 projects from the distal end portion 11 of the endoscope 10 using light from the light emitting portion 81 that is detected by the light receiving portion 82.

In other words, as shown in FIG. 19, since light from the light emitting portion 81 illuminates the light receiving portion 82, the control portion 20b determines that the treatment instrument, which, in this case, are the grasping forceps 40, is in a state where the treatment instrument is housed in the treatment instrument insertion channel 14a of the endoscope 10. On the other hand, as shown in FIG. 20, when light from the light emitting portion 81 is not illuminating the light receiving portion 82, the control portion 20b determines that the treatment instrument, which, in this case, are the grasping forceps 40, is in a state where the treatment instrument is not housed in the treatment instrument insertion channel 14a of the endoscope 10. Other effects are the same as those of the fourth embodiment.

Sixth Embodiment

Figure 21:
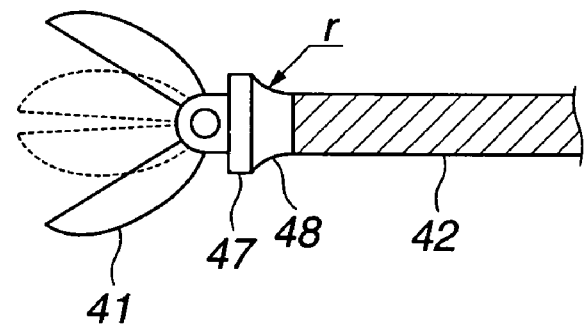
FIG. 21 is a diagram according to a sixth embodiment of the present invention showing a configuration of a distal end portion of grasping forceps that are a treatment instrument having a light reflective portion at a rear end portion of a treatment portion thereof.
Figure 22:
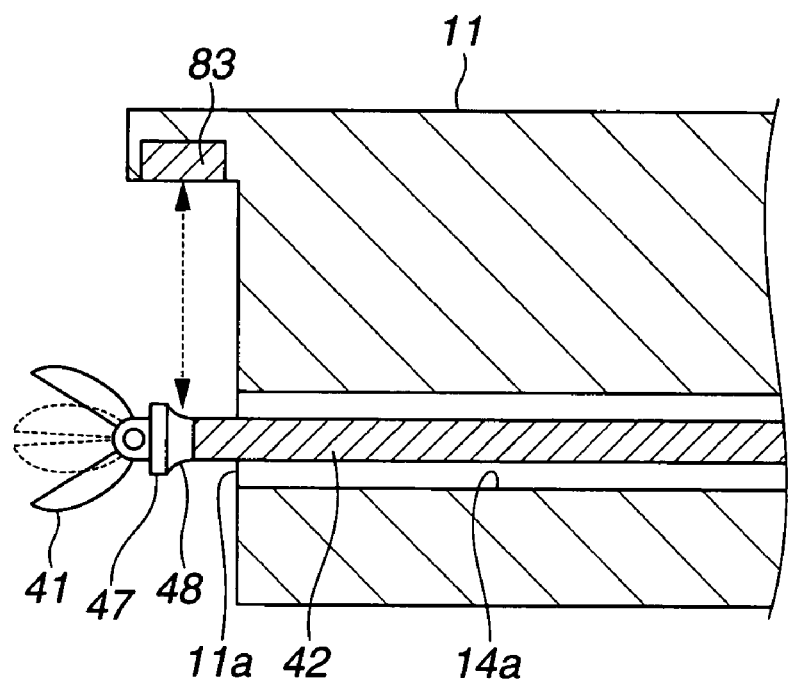
FIG. 22 is a cross sectional diagram showing a distal end portion of an endoscope having an optical sensor and which shows a state where grasping forceps project from the distal end portion.
Figure 23:
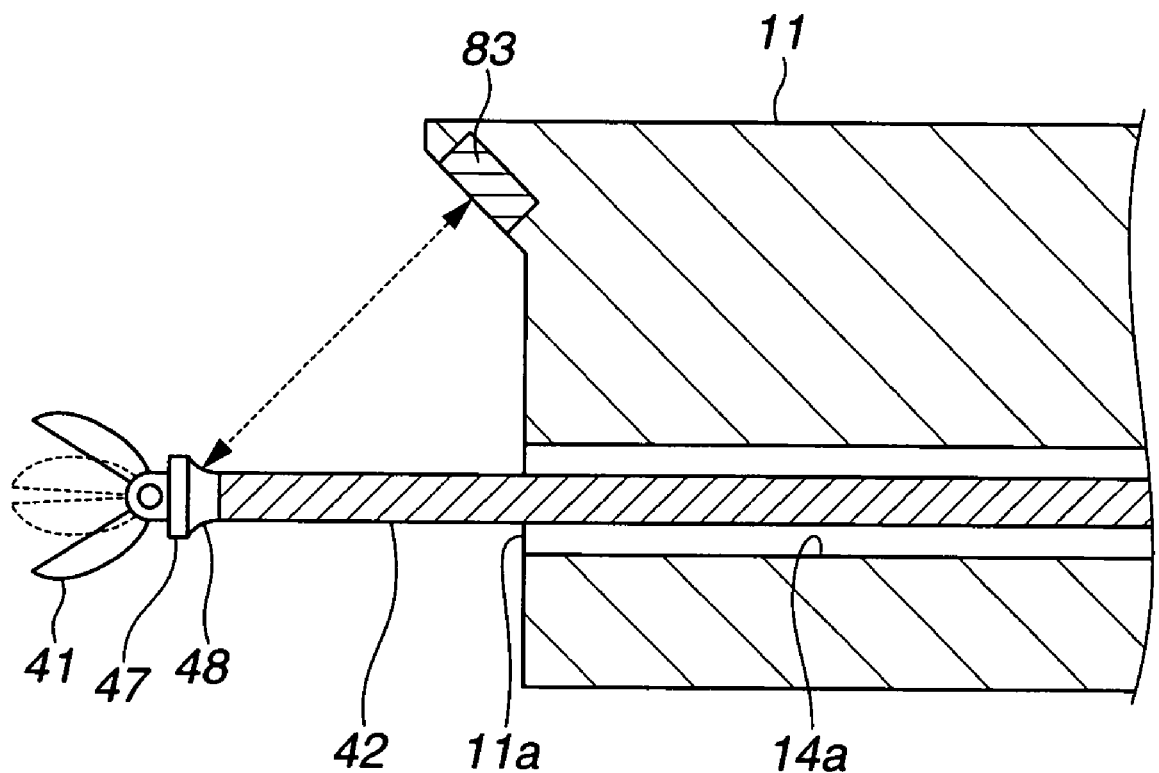
FIG. 23 shows a modification and is a cross sectional diagram showing a distal end portion of an endoscope having an optical sensor and which shows a state where grasping forceps project from the distal end portion.
Figure 24:
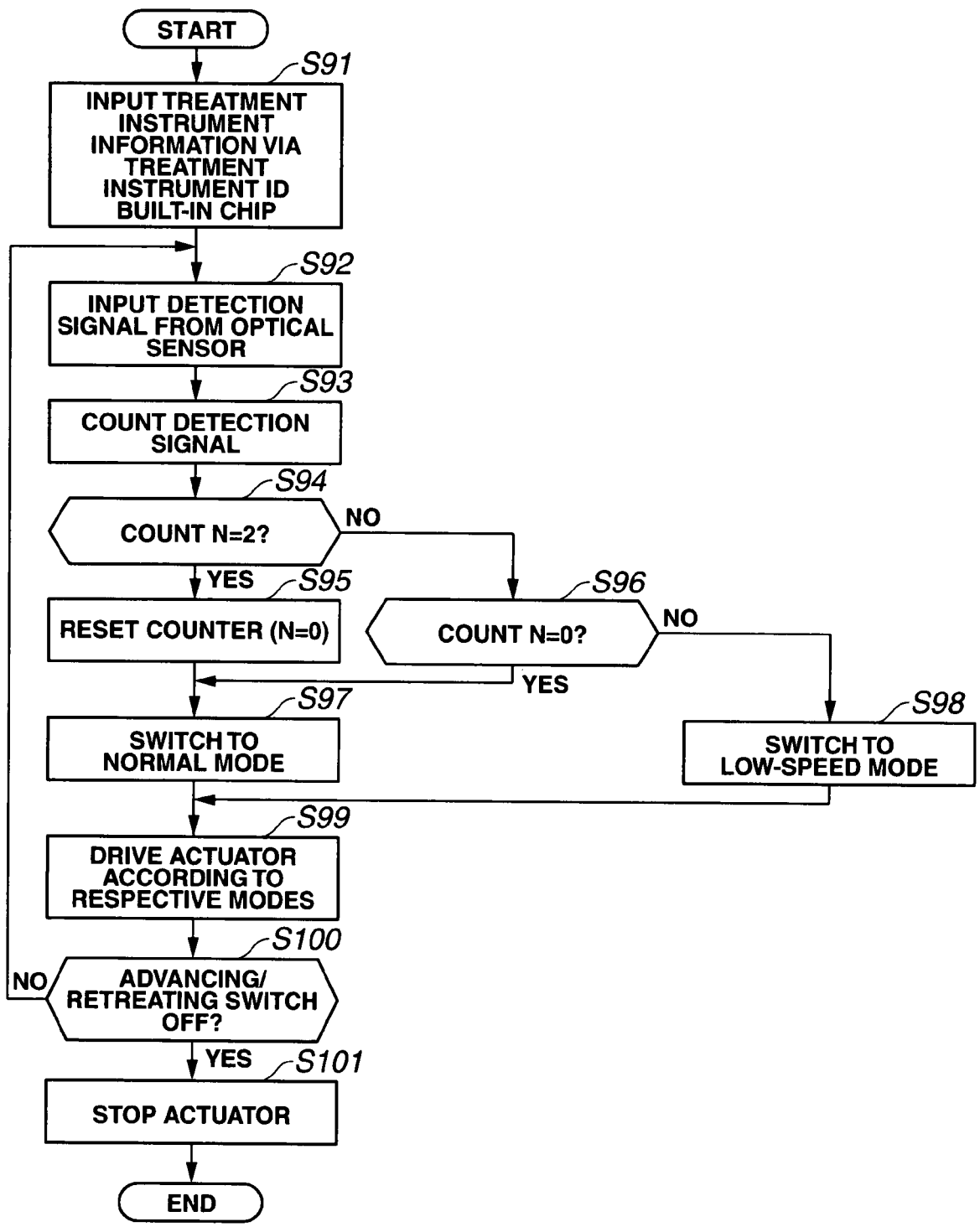
FIG. 24 is a flowchart illustrating control performed by a control apparatus of an endoscopic system.

Next, a sixth embodiment of the present invention will be described below with reference to FIGS. 21 to 24. FIGS. 21 to 24 show the sixth embodiment of the present invention, in which: FIG. 21 is a diagram showing a configuration of a distal end portion of grasping forceps that are treatment instruments having a light reflective portion provided at a rear end portion of a treatment portion thereof; FIG. 22 is a cross sectional diagram showing a distal end portion of an endoscope provided with an optical sensor and showing a state where grasping forceps project from the distal end portion; FIG. 23 shows a modification and is a cross sectional diagram showing a distal end of an endoscope provided with an optical sensor and showing a state where grasping forceps project from the distal end portion; and FIG. 24 is a flowchart illustrating control performed by a control apparatus of an endoscopic system.

In an endoscopic system 1 according to the present embodiment, the optical sensor of the endoscopic system 1 described with respect to the fourth embodiment is provided such that the positions of the light emitting portion and the light receiving portion are in proximity to each other, and the optical sensor is of a type that detects reflections of light emitted from the light emitting portion by the light receiving portion. Accordingly, for the present embodiment, detailed descriptions of like configurations and effects to the respective embodiments described above will be omitted, and only different portions shall be described below. Moreover, while a treatment instrument will be hereinafter described using, for example, grasping forceps 40, it is needless to say that the present embodiment is also applicable to various treatment instruments.

As shown in FIG. 21, with the grasping forceps 40 that are the treatment instruments of the present embodiment, a rear end portion of the treatment portion 41 that is connected to the distal end of the sheath 42 is provided with an approximately tubular-shaped reflector 47 having a reflecting surface 48 that is set to a predetermined curvature r such that the circumferential diameter decreases in a rearward direction. Moreover, the reflecting surface 48 of the reflector 47 is preferably mirror-finished.

In addition, the distal end portion 11 of the endoscope 10 according to the present embodiment is provided with an optical sensor 83 in which the light emitting portion and the light receiving portion are integrated. Therefore, since the endoscope 10 of the present embodiment is provided with only one optical sensor 83, the configuration of the distal end portion 11 may be simplified in comparison with the fifth embodiment.

Moreover, as shown in FIG. 23, the optical sensor 83 may be configured so that the light emitting portion and the light receiving portion face forward at a predetermined angle so as to correspond to the reflecting surface 48 that is set to a predetermined curvature r and which is formed on the reflector 47. As a result, since the optical sensor 83 mostly responds to light reflected off the reflecting surface 48 of the reflector 47, the optical sensor 83 may be prevented from coming close to the distal end portion 11 of the endoscope 10 and from responding to mucosa within the living body which may rise above the distal end face.

The endoscopic system 1 of the present embodiment configured as described above may either execute a control example by the control apparatus 20 in the same manner as in the fourth embodiment or execute a control example such as that illustrated by the flowchart of FIG. 24.

A control example of the flowchart shown in FIG. 24 and which is executed by the control apparatus 20 will now be described in detail. In the case of the control example shown in FIG. 24, when the optical sensor 83 detects reflected light from a passage made by the reflecting surface 48 of the reflector 47 of the grasping forceps 40, the control apparatus 20 is configured so as to count the number of detections N using an internal counter, not shown. Similarly, in this case, a drive instruction signal from the operation lever 34 of the controller 30 acts as a trigger and causes the control apparatus 20 to perform control based on the routine (steps) of the flowchart shown in FIG. 24.

More specifically, as shown in FIG. 24, the control apparatus 20 first reads treatment instrument information of the grasping forceps 40 inputted from the treatment instrument ID read sensor 52a and stored in the treatment instrument ID internal IC chip 49 at the treatment detection portion 20a. The treatment instrument information is inputted from the treatment detection portion 20a to the control portion 20b (S91).

Then, detected signals that are detected every time the reflector 47 of the grasping forceps 40 passes the light detection position of the optical sensor 83 is inputted to the control portion 20b from the optical sensor 83 (S92). In other words, when light illuminated by the light emitting portion is reflected by the reflecting surface 48 formed on the reflector 47 of the grasping forceps 40, the optical sensor 83 outputs a detected signal to the control apparatus 20.

At this point, the control portion 20b counts the number of passages N made by the reflector 47 of the grasping forceps 40 by counting the detected signals of the optical sensor 83 using an internal counter (S93).

Next, the control portion 20b judges whether the number of detected signals N of the optical sensor 83 that have been inputted to the counter is 2 (N=2) (S94). If the control portion 20b judges that the number of the detected signals is 2 (N=2), the control portion 20b resets the internal counter (S95), and proceeds to step S97.

On the other hand, if the control portion 20b judges that the number of the detected signals is not 2 (N≠2), the control portion 20b judges whether the number of detected signals N by the optical sensor 83 and inputted to the counter is 0 (N=0) (S96). At this point, if the number of detected signals N is 0 (N=0), the control portion 20b advances to step S97.

Then, in step S97, the control portion 20b switches the sheath 42 of the grasping forceps 40 to normal mode in which the sheath 42 advances/retreats at a preset predetermined speed (S97). In addition, in step S96, when the control portion 20b judges that the number of detected signals N is not 0 (N≠0), the control portion 20b switches the sheath 42 of the grasping forceps 40 to low-speed mode in which the sheath 42 advances/retreats at a predetermined speed that is slower than the normal mode (S98). Incidentally, since the respective modes are described with respect to the respective embodiments above, descriptions thereof will be omitted.

Next, in accordance with each switched mode, the control portion 20b drives the electrical advance/retreat apparatus 60 that is an actuator (S99). More specifically, when a transition is made to step S97, the control portion 20b switches to the normal mode and drives the electrical advance/retreat apparatus 60 in correspondence to a predetermined speed at which the sheath 42 of the grasping forceps 40 advances/retreats. On the other hand, when a transition is made to step S98, the control portion 20b switches to low-speed mode and drives the electrical advance/retreat apparatus 60 in correspondence to a predetermined speed that is slower than the normal mode at which the sheath 42 of the grasping forceps 40 advances/retreats.

Next, during driving of the electrical advance/retreat apparatus 60 according to the respective modes, the control portion 20b judges whether the operation lever 34 of the controller 30 is in an advance/retreat switch OFF state where the operation lever 34 is no longer operated (S100).

In other words, in the same manner as in the above-described first embodiment, a neutral state of the operation lever 34 of the controller 30 where the operation lever 34 is neither tilted forward nor backward is a state where no instruction signals for driving the electrical advance/retreat apparatus 60 are inputted to the control portion 20b. In this state, the control portion 20b judges that the advance/retreat switch is turned OFF. In addition, when the operation lever 34 of the controller 30 is being continuously tilted forward or backwards, the control portion 20b judges that the advance/retreat switch is turned ON.

Furthermore, when the control portion 20b judges that the advance/retreat switch is turned ON, the control portion 20b returns to step S92 to repeat the routine of steps S92 to S100. In addition, in step S100, when the electrical advance/retreat apparatus 60 is stopped or, in other words, when a drive signal is not being outputted to the electrical advance/retreat apparatus 60, the control portion 20b concludes the control flowchart shown in FIG. 24 as is.

As described above, the endoscopic system according to the present embodiment is also configured to include the effects of the respective embodiments. In addition, with the endoscopic system 1 according to the present embodiment, by having the reflector 47 of the grasping forceps 40 that are the treatment instruments advance/retreat so as to pass the detection position of the optical sensor 83 by arbitrary operations of the controller 30, the operator is able to switch between the normal mode and the low-speed mode.

Seventh Embodiment

Figure 25:
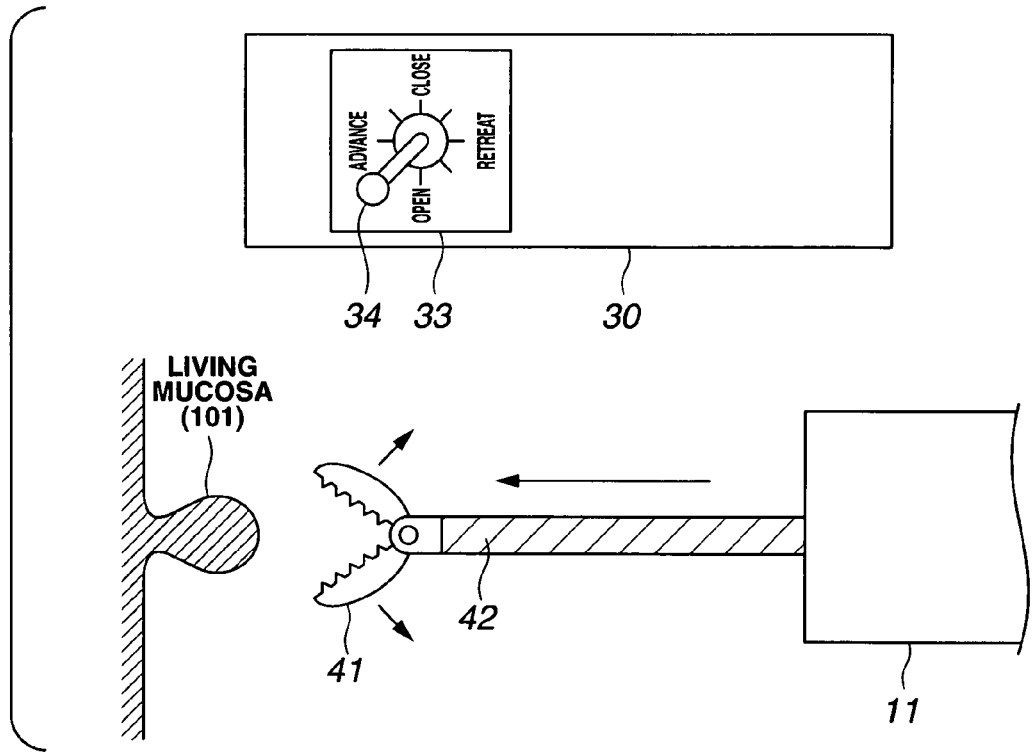
FIG. 25 is a diagram showing a treatment portion of biopsy forceps projecting from the distal end portion of an endoscope according to a seventh embodiment of the present invention in a state prior to the removal of living mucosa.
Figure 26:
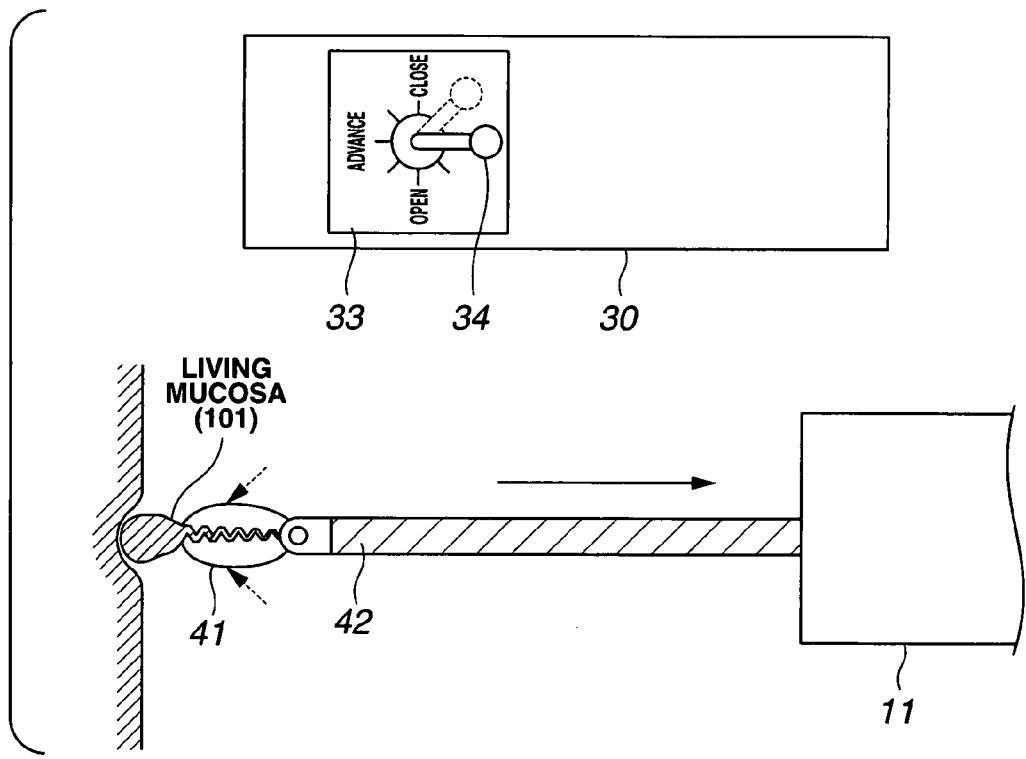
FIG. 26 is a diagram showing a state after the removal of living mucosa by a treatment portion 41 of biopsy forceps.
Figure 27:
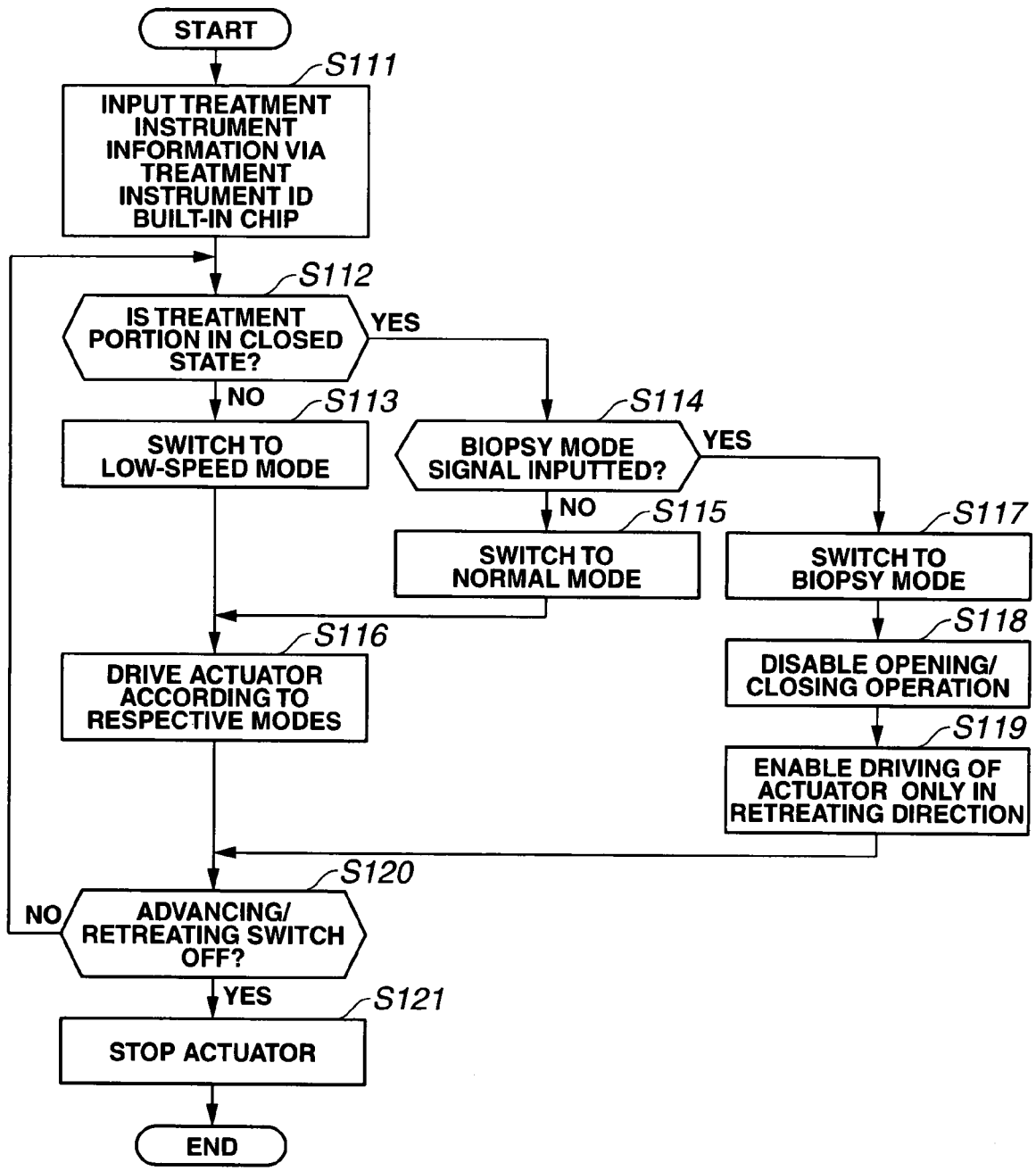
FIG. 27 is a flowchart illustrating control performed by a control apparatus of an endoscopic system.

Next, a seventh embodiment of the present invention will be described below with reference to FIGS. 25 to 27. FIGS. 25 to 27 show the seventh embodiment of the present invention, in which: FIG. 25 is a diagram showing a state prior to the removal of living mucosa by a treatment portion of the biopsy forceps projecting from the distal end of an endoscope; FIG. 26 is a diagram showing a state after the removal of living mucosa by the treatment portion of the biopsy forceps; and FIG. 27 is a flowchart illustrating control performed by a control apparatus of an endoscopic system.

In the present embodiment, the treatment instruments 40 to be used in the endoscopic system 1 are biopsy forceps (hereinafter described as the biopsy forceps 40). The present embodiment is a control example in which the advance/retreat displacement of the sheath 42 of the biopsy forceps 40 is controlled by the control apparatus 20. Accordingly, for the present embodiment as well, detailed descriptions of like configurations and effects to the respective embodiments described above will be omitted, and only different portions shall be described below.

Incidentally, as well known, the biopsy forceps 40 to be used in the endoscopic system 1 according to the present embodiment are for extracting living mucosa or living body tissue by the opening and closing treatment portion 41.

Extraction of living mucosa (denoted by reference character 101 as shown in FIGS. 25 and 26) using the biopsy forceps 40 is performed by the operator as shown in FIGS. 25 and 26 by predetermined tilt operations of the operation lever 34 provided at the operation instruction portion 33 of the controller 30.

To elaborate, as shown in FIG. 25, when feeding out the treatment portion 41 of the biopsy forceps 40 of the distal end portion 11 of the endoscope 10 in a forward direction, the operator tilts the operation lever 34 of the controller 30 forward. At the same time, when opening the treatment portion 41 towards the living mucosa 101, the operator tilt-operates the operation lever 34 in the direction displayed "open" that is displayed on the operation instruction portion 33. Consequently, the treatment portion 41 of the biopsy forceps 40 opens while moving forward together with the sent-out sheath 42.

Then, as shown in FIG. 26, when closing the treatment portion 41 of the biopsy forceps 40 to nip the living mucosa 101, the operator tilt-operates the operation lever 34 of the controller 30 in the direction displayed "open" that is displayed on the operation instruction portion 33, and when the operator desires to simultaneously retract the sheath 42, the operator simultaneously tilts the operation lever 34 backward. As a result, the treatment portion 41 of the biopsy forceps 40 moves backward together with the sheath 42 in a state where the living mucosa 101 is separated and nipped.

As this point where the living mucosa is being nipped, the living mucosa 101 may be separated from the living body wall more easily by having the treatment portion 41 of the biopsy forceps 40 retreat at high speed. Therefore, in addition to the normal mode and the low-speed mode of the respective embodiments described above, the endoscopic system 1 according to the present embodiment is configured to be also switchable to a biopsy mode that is a high-speed mode to be used during extraction of the living mucosa 101.

Accordingly, the control apparatus 20 of the endoscopic system 1 according to the present embodiment executes the control example of the flowchart shown in FIG. 27. Accordingly, for the present embodiment as well, detailed descriptions of like configurations and effects to the respective embodiments described above will be omitted, and only different portions shall be described below.

A control example of the flowchart shown in FIG. 27 and which is executed by the control apparatus 20 will now be described in detail. Moreover, in the case of the control example shown in FIG. 27, switching to the biopsy mode may be performed by the operator by arbitrary operations of the controller 30. This switching of modes may be performed by, for example, so-called one-click or double-click switching where the operation lever 34 of the controller 30 is pressed into the operation instruction portion 33, or a switch for switching to biopsy mode may be provided on the controller 30.

First, a drive instruction signal from the operation lever 34 of the controller 30 similarly acts as a trigger and causes the control apparatus 20 to perform control based on the routine (steps) of the flowchart shown in FIG. 27.

More specifically, when treatment instrument information informing that the treatment instrument to be used in step S11 are biopsy forceps is inputted (S111), the control portion 20b of the control apparatus 20 judges whether the treatment portion 41 of the biopsy forceps 40 is in a closed state (S112). For this judgment, the control portion 20b judges the open/closed state of the treatment portion 41 of the biopsy forceps 40 by the advance/retreat displacement position of the slider 46 of the handle portion 44 from detected signals of the slide detection sensor 53b of the retaining box 53.

Then, when the control portion 20b judges that the treatment portion 41 of the biopsy forceps 40 is not a closed state and is an open state instead, the control portion 20b switches the advance/retreat speed of the sheath 42 to the low-speed mode that is a speed slower than the normal mode (S113). On the other hand, when the control portion 20b judges that the treatment portion 41 of the biopsy forceps 40 is in a closed state, the control portion 20b judges whether a biopsy mode signal has been inputted (S114). At this point, if a biopsy mode signal has not been inputted, the control portion 20b switches the advance/retreat speed of the sheath 42 to the normal mode (S115).

Next, in accordance with each switched mode, the control portion 20b drives the electrical advance/retreat apparatus 60 that is an actuator (S116). More specifically, when a transition is made to step S113, the control portion 20b switches to low-speed mode and drives the electrical advance/retreat apparatus 60 in correspondence to a predetermined speed that is slower than the normal mode at which the sheath 42 of the biopsy forceps 40 advances/retreats. On the other hand, when a transition is made to step S115, the control portion 20b switches to the normal mode and drives the electrical advance/retreat apparatus 60 in correspondence to a predetermined speed at which the sheath 42 of the biopsy forceps 40 advances/retreats.

Additionally, in step S114, when the control portion 20b judges that a biopsy mode signal has been inputted, the control portion 20b switches to a biopsy mode (S117). In this case, the biopsy mode refers to a high-speed advance/retreat mode in which the sheath 42 of the biopsy forceps 40 advances/retreats at a predetermined speed that is faster than the preset normal mode.

Subsequently, the control portion 20b disables opening/closing operations of the treatment portion 41 of the biopsy forceps 40 (S118). In other words, the control portion 20b does not output a drive signal to the retaining box 53 of the electrical operation apparatus 50 even if an operation signal for changing to an open state is inputted by an operation of the controller 30 from a closed state of the treatment portion 41 of the biopsy forceps 40.

As a result, the closed state of the treatment portion 41 of the biopsy forceps 40 is maintained. In other words, when the biopsy mode is selected, a state where the living mucosa 101 is nipped by the treatment portion 41 of the biopsy forceps 40 is maintained. Therefore, the treatment portion 41 is prevented from opening when the operator accidentally tilt-operates the operation lever 34 of the controller 30 in a direction that changes the treatment portion 41 to an open state, thereby preventing the operator from missing the nipped living mucosa 101.

Subsequently, in a state where opening/closing operations of the treatment portion 41 of the biopsy forceps 40 are still disabled, the control portion 20b drives the electrical advance/retreat apparatus 60 that is an actuator only in the retreating direction of the sheath 42 (S119). Therefore, unnecessary operations where the sheath 42 advances at high speed may be avoided when the operator accidentally tilt-operates the operation lever 34 of the controller 30 in a forward advancing direction of the sheath 42 during biopsy mode.

In other words, when the biopsy mode is selected, the closed state of the treatment portion 41 of the biopsy forceps 40 is maintained, and only high-speed retreat of the sheath 42 of the biopsy forceps 40 will be possible.

Next, during driving of the electrical advance/retreat apparatus 60 according to the respective modes, the control portion 20b judges whether the operation lever 34 of the controller 30 is in an advance/retreat switch OFF state where the operation lever 34 is no longer operated (S120).

Furthermore, when the control portion 20b judges that the advance/retreat switch is turned ON, the control portion 20b returns to step S112 to repeat the routine of steps S112 to S119. On the other hand, when the control portion 20b judges that the advance/retreat switch is turned OFF, the control portion 20b suspends output of the drive signal of the electrical advance/retreat apparatus 60 that is an actuator and stops the electrical advance/retreat apparatus 60 (S121), thereby stopping the advance/retreat of the sheath 42 of the biopsy forceps 40 and concluding the control flowchart shown in FIG. 27.

As described above, a configuration of the endoscopic system 1 according to the present embodiment that achieves favorable operability may be realized in which, when a treatment instrument that extracts living mucosa 101 and the like, which, in this case are biopsy forceps 40, is used, the sheath 42 advances/retreats at low speed in a state where the treatment portion 41 is opened towards the living mucosa 101 to be extracted, while the sheath 42 retreats at high speed when biopsy mode is selected in order to separate the living mucosa 101 that is nipped by the treatment portion 41 in a speedy manner. In addition, since the endoscopic system 1 according to the present embodiment is unable to perform opening/closing operations of the treatment portion 41 and forward displacement operations of the sheath 42 during an extraction of the living mucosa 101 by the treatment portion 41, the living mucosa 101 and the like may be extracted in a secure manner.

Eight Embodiment

Figure 28:
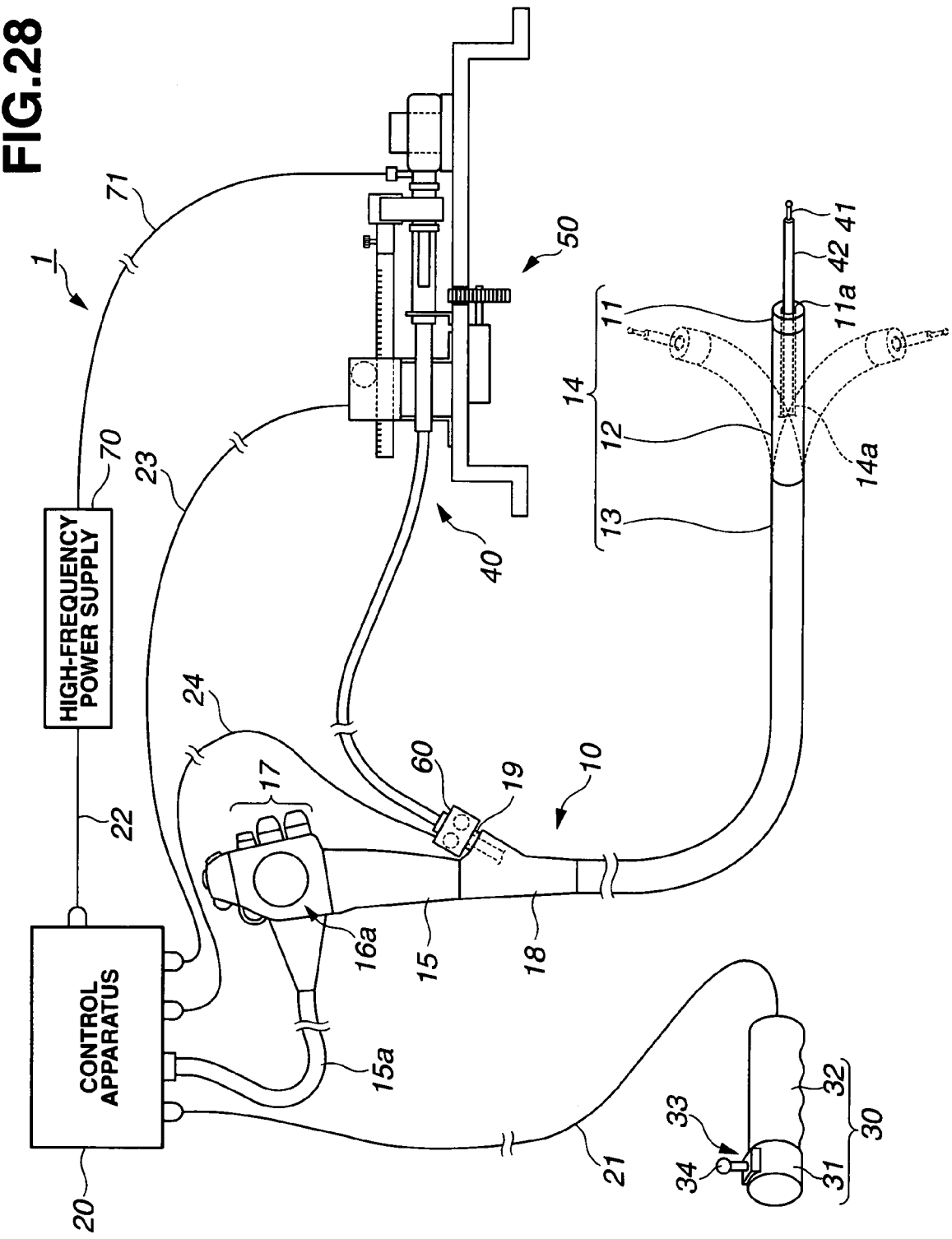
FIG. 28 is a diagram showing an overall configuration of an endoscopic system according to an eighth embodiment of the present invention to which a high-frequency knife has been set.
Figure 29:
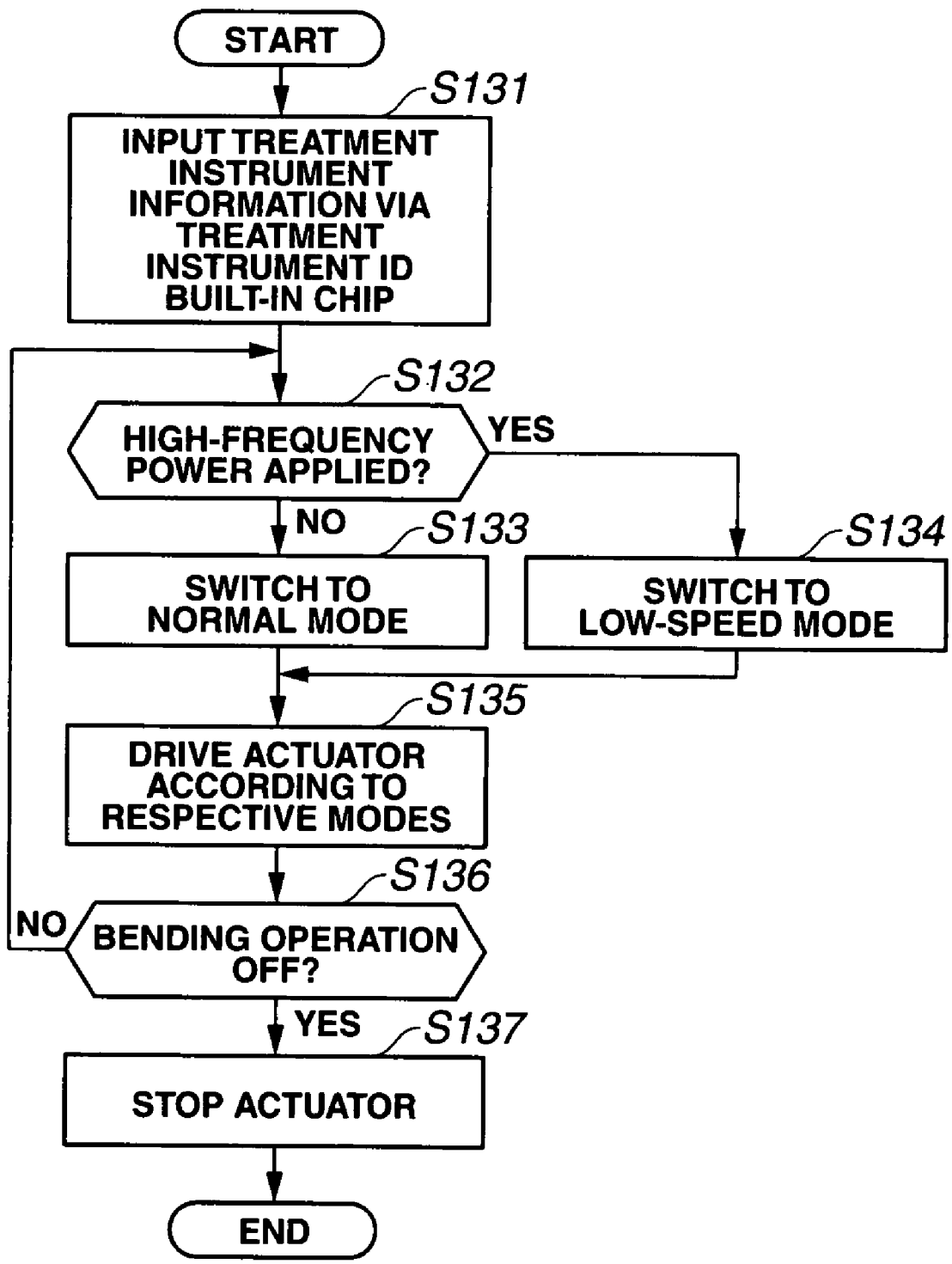
FIG. 29 is a flowchart illustrating control performed by a control apparatus of the endoscopic system shown in FIG. 28.

Next, an eighth embodiment of the present invention will be described below with reference to FIGS. 28 and 29. Moreover, FIGS. 28 and 29 show the eighth embodiment of the present invention, in which: FIG. 28 is a diagram showing an overall configuration of an endoscopic system to which a high-frequency knife has been set; while FIG. 29 is a flowchart illustrating control performed by the control apparatus of the endoscopic system shown in FIG. 28.

As shown in FIG. 28, an endoscope 10 of an endoscopic system 1 according to the present embodiment is configured so that a bending portion 12 of an insertion portion 14 is electrically bent by operations of a track ball 16a provided at an operation portion 15. Incidentally, the endoscope 10 having such an electrical bending mechanism by means of the track ball 16a is a conventional configuration. Therefore, a detailed description thereof will be omitted. In addition, while the present embodiment will be described using an example of the track ball 16a that bend-operates the bending portion 12, the present embodiment is not limited to this example, and a bending operation lever may be used instead.

As described, with the endoscopic system 1 according to the present embodiment, when the endoscope 10 that electrically drives the bending portion 12 is used, the control apparatus 20 executes the control example according to the respective steps of the flowchart shown in FIG. 29. Other configurations of the endoscopic system 1 are the same as the respective embodiments. Therefore, detailed descriptions of configurations and effects that are the same as those of the respective embodiments described above will be omitted, and only different portions shall be described below.

In addition, while the treatment instrument to be used in the present embodiment will be described using the high-frequency knife 40 as an example, the present embodiment is not limited to this example. Instead, the present embodiment is also applicable to any treatment instrument that applies high frequency to the treatment portion 41.

Furthermore, with this endoscopic system 1, when a bending instruction signal for bending the bending portion 12 of the endoscope 10 is inputted to the control apparatus 20, the input of the bending instruction signal acts as a trigger and causes the control apparatus 20 to perform control based on the routine (steps) of the flowchart shown in FIG. 29. In other words, when the track ball 16a of the endoscope 10 is operated by the operator, the control apparatus 20 outputs a drive signal to an electrical bending mechanism built into the endoscope 10 that causes the electrical bending mechanism to drive bending of the bending portion 12 based on the operation state of the track ball 16a. At this point, the control apparatus 20 executes a control example in accordance with the respective steps of the flowchart shown in FIG. 29.

First, as shown in FIG. 29, the control apparatus 20 reads treatment instrument information of the high-frequency knife 40 inputted from the treatment instrument ID read sensor 52a and stored in the treatment instrument ID internal IC chip 49 at the treatment detection portion 20a. The treatment instrument information is inputted from the treatment detection portion 20a to the control portion 20b (S131).

Then, the control portion 20b of the control apparatus 20 judges whether the high frequency power supply 70 has been energized (S132). At this point, when the high frequency power supply 70 is in an OFF state, the control portion 20b switches to the normal mode (S133). In this case, the normal mode refers to a normal bending mode in which the bending portion 12 of the endoscope 10 is bent at a predetermined speed.

At this point, when the high frequency power supply 70 is in an ON state, the control portion 20b switches to low-speed mode (S134). In this case, low-speed mode refers to a low-speed bending mode in which the bending portion 12 of the endoscope 10 is bent at a predetermined speed that is slower than the normal mode.

Next, in accordance with each switched mode, the control portion 20b drives the electrical bending mechanism that is an actuator in this case (S135). More specifically, when a transition is made to step S133, the control portion 20b switches to the normal mode and outputs a normal bending drive signal for performing bending in correspondence to a predetermined speed to the electrical bending mechanism that drives the bending portion 12 of the endoscope 10. On the other hand, when a transition is made to step S134, the control portion 20b switches to low-speed mode and outputs a low-speed bending drive signal for performing bending in correspondence to a predetermined speed that is slower than the normal mode to the electrical bending mechanism that drives the bending portion 12 of the endoscope 10. In other words, the speed at which the bending portion 12 of the endoscope 10 bends varies according to the ON/OFF state of the high frequency power supply 70.

In addition, during driving of the electrical bending mechanism according to the respective modes in step S135, the control portion 20b judges whether the current state is a bending operation OFF state where the track ball 16a of the operation portion 15 of the endoscope 10 is no longer operated (S136).

In other words, a state where no operations are performed on the track ball 16a by the operator is a state where instruction signals for driving the electrical bending mechanism are not inputted to the control portion 20b. In this state, the control portion 20b judges that bending operations are OFF.

In addition, in a state where the track ball 16a is being continuously operated, the control portion 20b judges that bending operations are ON.

Furthermore, when the control portion 20b judges that bending operations are ON, the control portion 20b returns to step S132 to repeat the routine of steps S132 to S136. On the other hand, when the control portion 20b judges that the bending operations are OFF, the control portion 20b suspends output of the drive signal of the electrical bending mechanism that is an actuator and stops the electrical bending mechanism (S137), thereby stopping the advance/retreat of the bending portion 12 of the endoscope 10 and concluding the control flowchart shown in FIG. 29.

As seen, with the endoscopic system 1 according to the present embodiment, since the bending displacement of the bending portion 12 of the endoscope 10 is performed at low speed when high frequency is being applied to the treatment portion 41 of the high-frequency knife 40, a configuration is realized in which dissection of living mucosa may be performed in an easy manner. Consequently, the operator is able to accurately perform dissection of target living mucosa.

Moreover, in addition to treatment instruments that use high frequency, various other treatment instruments may be used under the control of the control apparatus 20 by changing the judgment performed in step S132 with respect to the state where the treatment portion 41 becomes active, and control may be performed so that the bending speed of the bending portion 12 of the endoscope 10 is switched to low-speed mode.

REFERENCE EXAMPLES

Reference examples of each endoscopic system 1 described above will be described below.

First Reference Example

Figure 30:
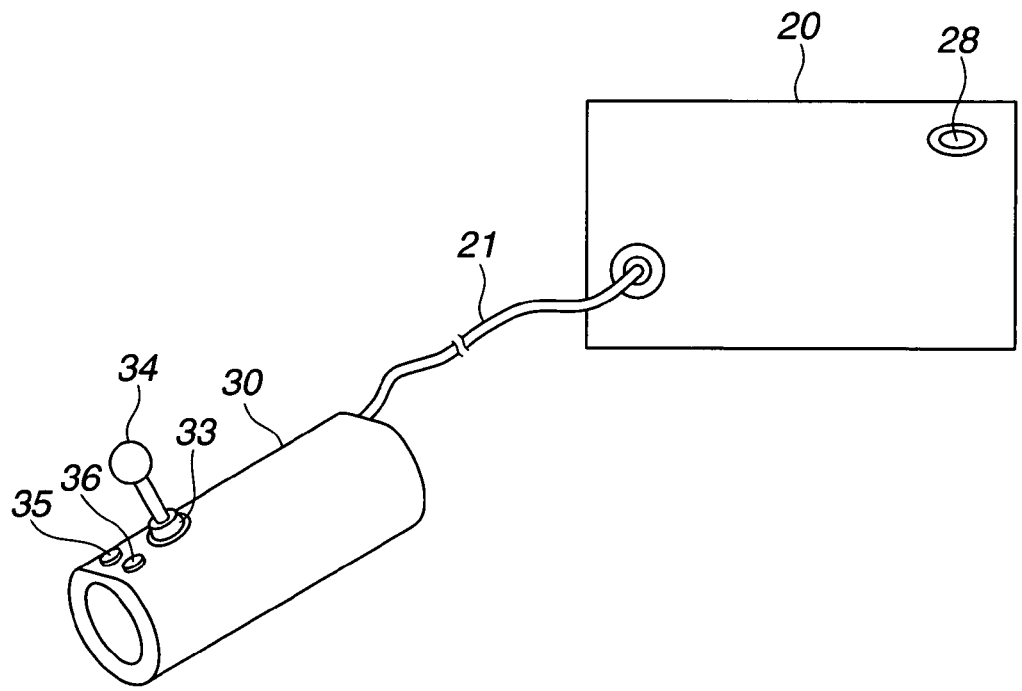
FIG. 30 is a perspective view showing a controller of an endoscopic system 1 and a control apparatus according to a first reference example.

First, a first reference example will be described. FIG. 30 is a perspective view showing a controller of an endoscopic system 1 and a control apparatus according to the first reference example.

As shown in FIG. 30, a controller 30 according to the present reference example is provided with two operation buttons 35 and 36. In addition, a main switch 28 is disposed on a front panel of the control apparatus 20. The two operation buttons 35 and 36 are capable of issuing various operation instructions separately from the main switch 28 of the control apparatus 20.

For instance, the operation buttons 35 and 36 are configured so that one of the operation buttons 35 and 36 is a controller activation switch while the other is a controller stopping switch. In the case of this configuration, the controller 30 cannot be energized or stopped unless the operator knowingly operates the operation buttons 35 and 36. In other words, it is possible to knowingly initiate or stop output of operation instruction signals from the controller 30 to the control apparatus 20.

Consequently, by setting the controller 30 to a stopped state when connecting the controller 30 to the control apparatus 20 and the like, an instruction signal is not outputted from the controller 30 to the control apparatus 20 even if the operation lever 34 is inadvertently touched. Therefore, at the treatment instrument 40, operations of the treatment portion 41 by the treatment instrument electrical operation apparatus 50 and advance/retreat movement of the sheath 42 by the treatment instrument electrical advance/retreat apparatus 60 are not performed. As a result, erroneous operations by the operator may be prevented and, in turn, failures, damages and the like of the endoscopic system 1 and the treatment instrument 40 may be prevented.

In addition, the two operation buttons 35 and 36 may be configured so that one of the two operation buttons 35 and 36 is an activation switch for the controller 30 and the other is a cancel switch that disables various switch operations of the control apparatus 20.

In other words, by turning ON both the controller-side activation switch and the cancel button, both the treatment instrument electrical operation apparatus 50 and the treatment instrument electrical advance/retreat apparatus 60 of the endoscopic system 1 may be driven solely by operations of the controller 30. In other words, all operation instructions by the operation buttons on the control apparatus 20 side are disabled.

Consequently, even when the various switches on the control apparatus 20 side are erroneously operated, the treatment instrument electrical operation apparatus 50 and the treatment instrument electrical advance/retreat apparatus 60 are not driven. As a result, erroneous operations on the control apparatus 20 side may be prevented, and the same effects as described above may be achieved.

Second Reference Example

Figure 31:
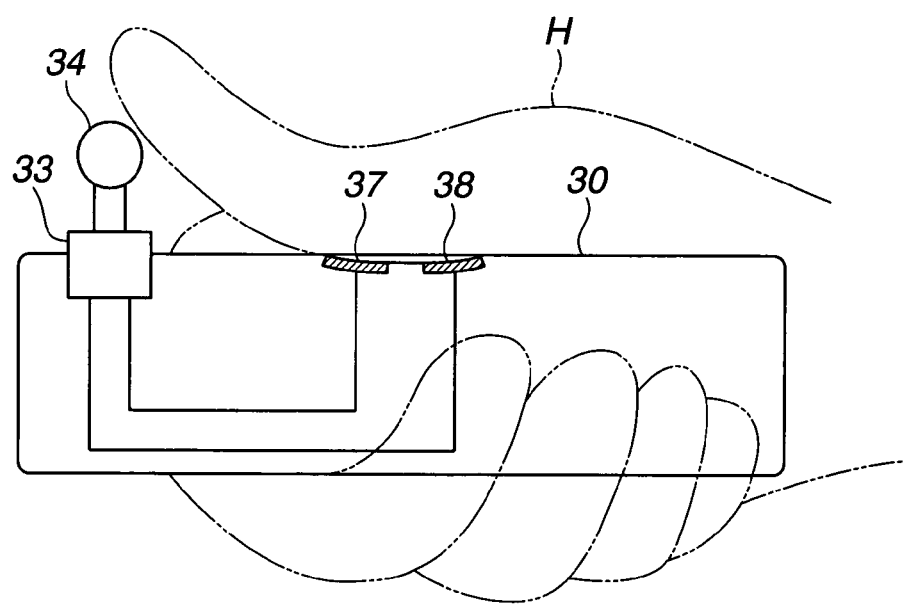
FIG. 31 is a cross sectional diagram showing a state where a controller is grasped by an operator according to a second reference example.

Next, a second reference example will be described. FIG. 31 is a cross sectional diagram showing a state where a controller is grasped by an operator according to the second reference example.

As shown in FIG. 31, for the present reference example, the controller 30 is configured so that the operation lever 34 of the operation instruction portion 33 is not enabled unless a user such as an operator grasps the controller 30 with a hand H represented by the dashed-two dotted line.

To elaborate, as shown in FIG. 31, the controller 30 is provided with a pair of electrodes 37 and 38 comprising bio-detection means that is touched by the hand H of the user on, in this case, a rearward side on the same surface thereof as the operation instruction portion 33. These electrodes 37 and 38 are disposed so as to be spaced by a predetermined distance, and are respectively electrically connected to the operation instruction portion 33.

By having the user grasp the controller 30 configured as described above, the hand H of the user touches the respective electrodes 37 and 38, whereby the respective electrodes 37 and 38 become conductive via the hand H that is a living body, and the operation instruction portion 33 of the controller 30 is enabled. In other words, the controller 30 is in a disabled state when not grasped by the user where instruction signals are not outputted to the control apparatus 20 even when the operation lever 34 of the operation instruction portion 33 is tilt-operated.

According to such a configuration, since operations by the operation lever 34 of the operation instruction portion 33 are enabled only when the controller 30 is securely grasped by the user, operation signals are not outputted to the control apparatus 20 even if the controller 30 inadvertently touches something and the operation lever 34 is tilted. Moreover, an activation switch may be provided instead which switches ON the functions of the endoscopic system 1 when the respective electrodes 37 and 38 of the controller 30 become conductive.

Third Reference Example

Figure 32:
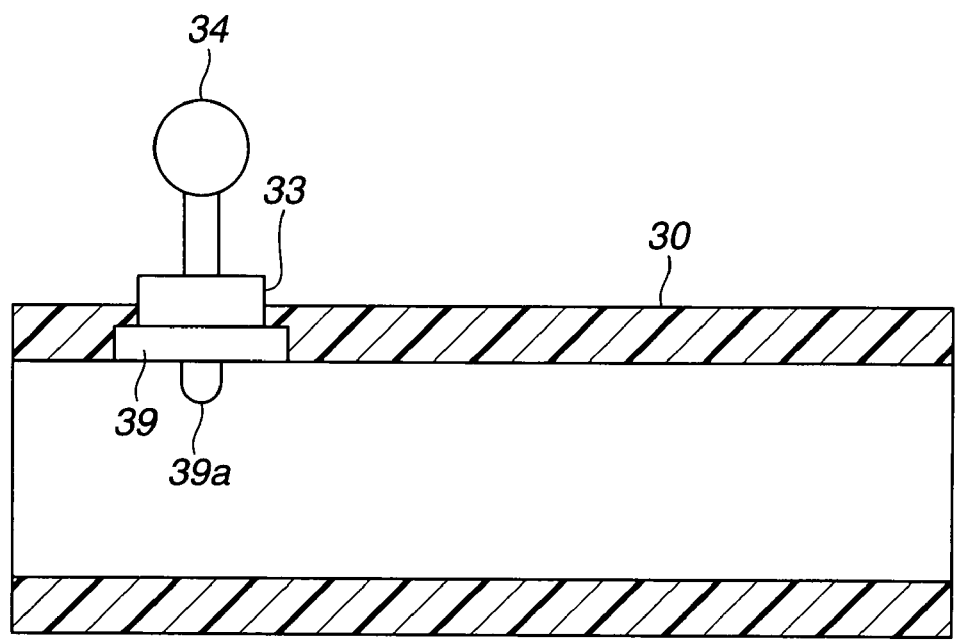
FIG. 32 is a cross sectional diagram showing a controller having a limit switch according to a third reference example.
Figure 33:
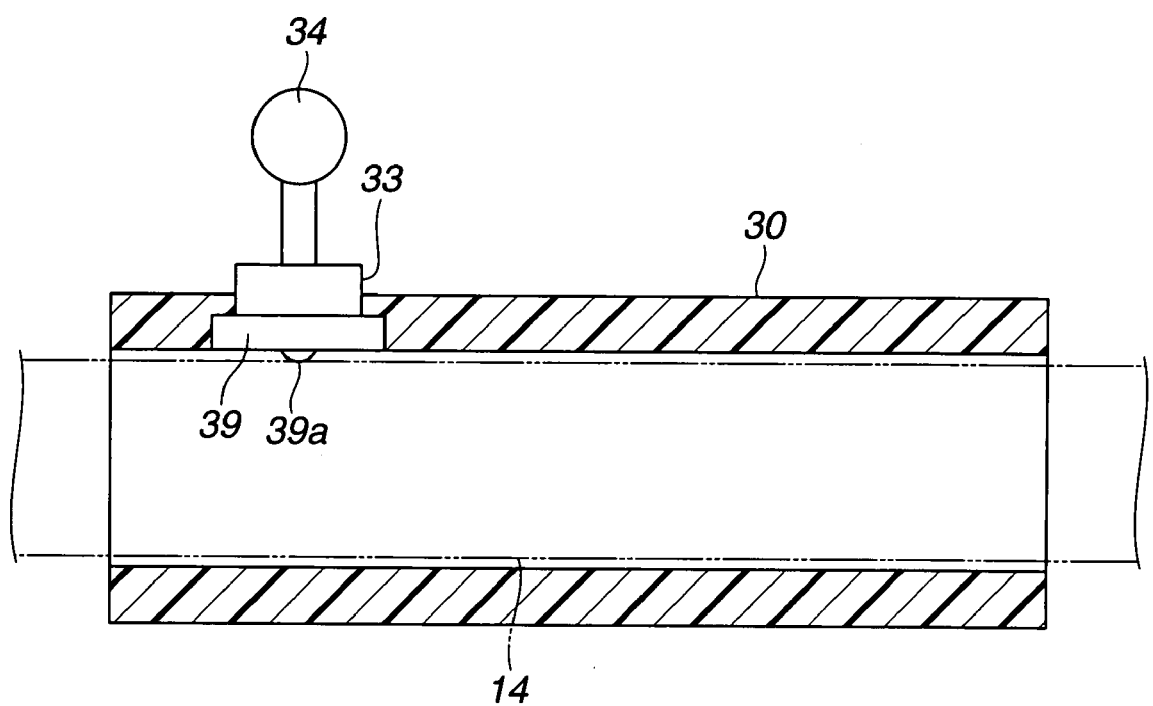
FIG. 33 is a cross sectional diagram showing a state where an insertion portion is inserted into the controller shown in FIG. 32.

Next, a third reference example will be described. FIG. 32 is a cross sectional diagram showing a controller provided with a limit switch according to the third reference example, while FIG. 33 is a cross sectional diagram showing a state where an insertion portion is inserted into the controller shown in FIG. 32.

As shown in FIG. 32, the controller 30 according to the present reference example is provided below the operation instruction portion 33 thereof with a limit switch 39 that is scope detection means having a limit button 39a that protrudes into an insertion hole of the insertion portion. In other words, as shown in FIG. 32, the limit switch 39 of the controller 30 is turned off when the insertion portion 14 of the endoscope 10 is not inserted, and when the insertion portion 14 of the endoscope 10 is inserted, the limit button 39a touches and is inserted into the insertion portion 14, thereby turning the limit switch 39 on.

Consequently, the controller 30 is arranged to be energized by having the limit switch 39 recognize the insertion of the insertion portion 14 that enables the operation instruction portion 33 only in a state where the insertion portion 14 is inserted to the controller 30. As a result, since the operation instruction portion 33 of the controller 30 is enabled and is energized only when the insertion portion 14 of the endoscope 10 is securely inserted into the controller 30, similar effects to the respective reference examples described above may be achieved.

Fourth Reference Example

Figure 34:
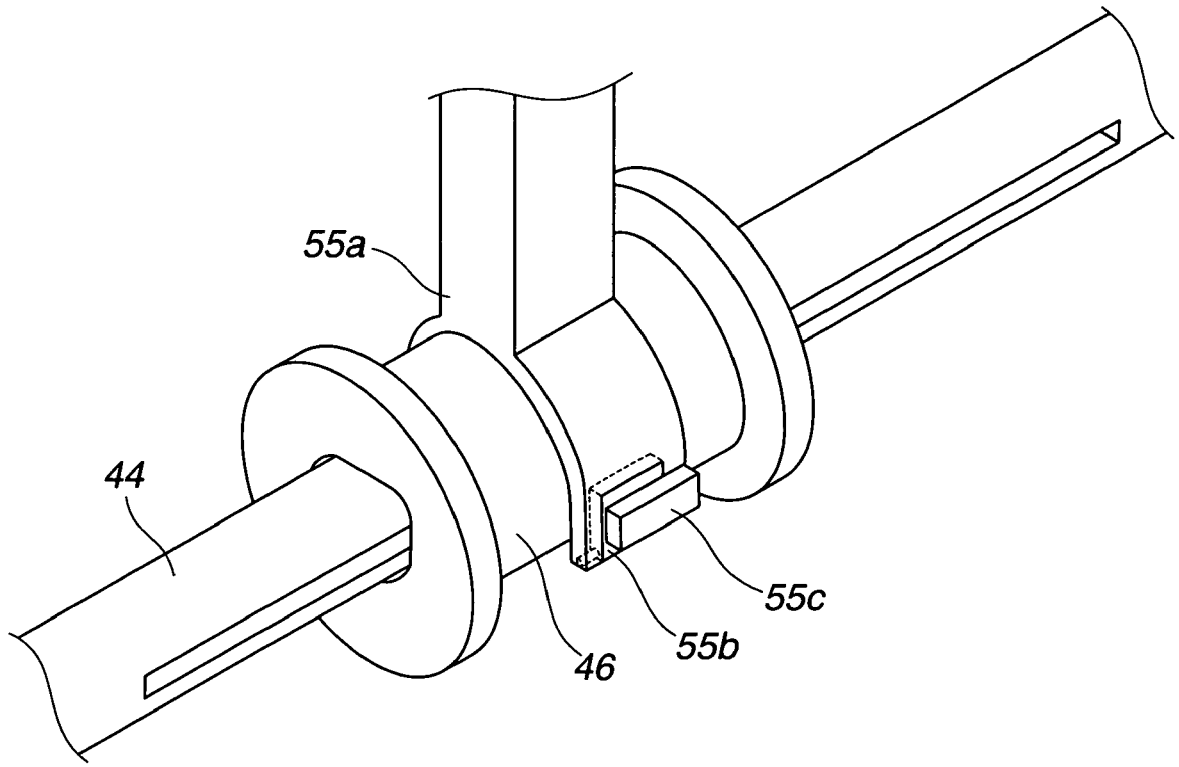
FIG. 34 is a perspective view showing a state where a slider of a treatment instrument is mounted to a retaining portion of a treatment instrument electrical operation apparatus having a limit switch according to a fourth reference example.
Figure 35:
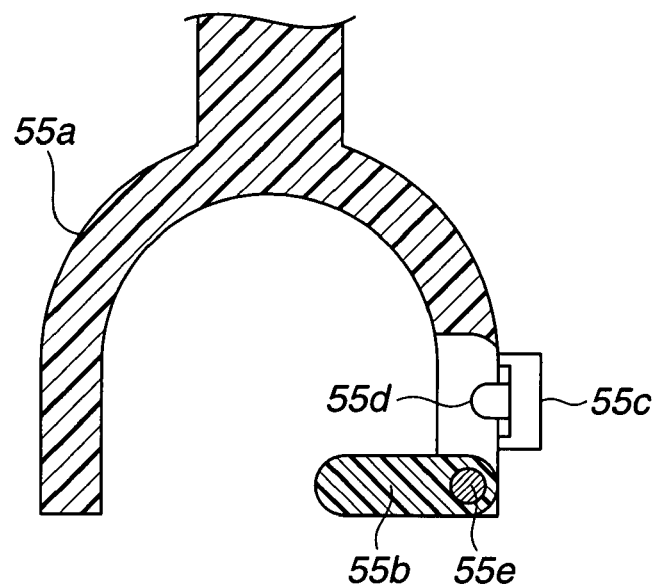
FIG. 35 is a cross sectional diagram showing a retaining portion in a state where a slider is not mounted.
Figure 36:
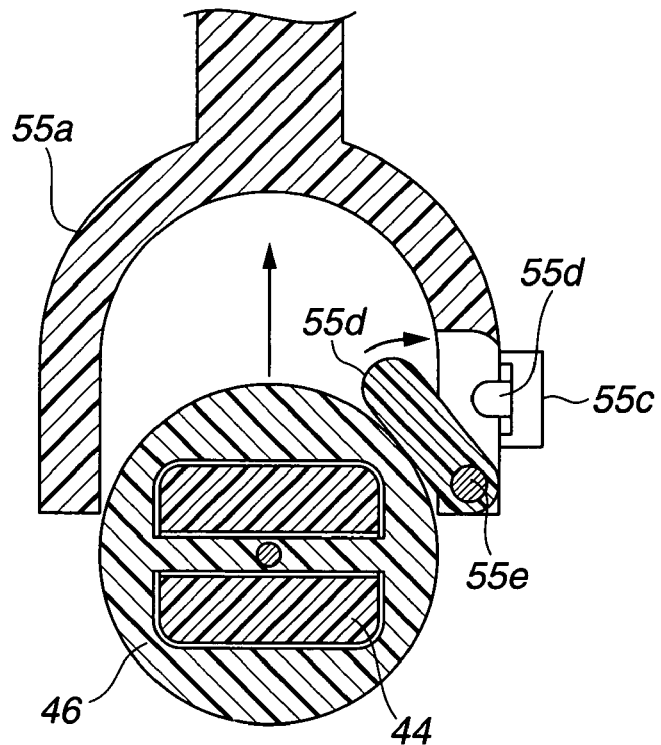
FIG. 36 is a cross sectional diagram for describing a state where a slider is mounted.
Figure 37:
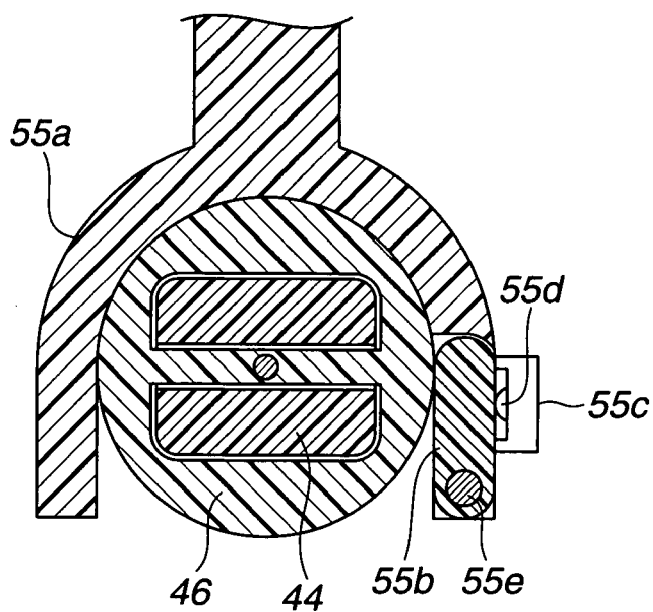
FIG. 37 is a cross sectional diagram showing a state where a slider is mounted to a retaining portion.

Next, a fourth reference example will be described. FIG. 34 is a perspective view showing a state where a slider of a treatment instrument is mounted to a retaining portion of a treatment instrument electrical operation apparatus provided with a limit switch according to the fourth reference example; FIG. 35 is a cross sectional diagram showing the retaining portion in a state where a slider is not mounted; FIG. 36 is a cross sectional diagram for describing a state where a slider is mounted; and FIG. 37 is a cross sectional diagram showing a state where a slider is mounted to the retaining portion.

As shown in FIG. 34, in the present reference example, a limit switch 55c that detects the mounting of a slider 46 slideably set on a handle portion 44 of the treatment instrument 40 is provided on a retaining portion 55a of the treatment instrument electrical operation apparatus 50.

The retaining portion 55a comprises a rotary plate body 55b rotatably mounted to a lateral wall portion by a shaft 55e. A limit switch 55c having a limit button 55d is provided on a wall portion on the side to which the rotary plate body 55b is provided. The limit switch 55c is a switch for turning ON/OFF the controller 30.

Moreover, as shown in FIG. 35, the own weight of the rotary plate body 55b causes the rotary plate body 55b to assume a toppled horizontal state. In addition, an elastic member such as a spring may be provided on a lateral wall portion of the retaining portion 55a so that the rotary plate body 55b assumes the toppled horizontal state.

As seen, in the course of mounting the slider 46 of the treatment instrument 40 to the retaining portion 55a, as shown in FIG. 36, the slider 46 is mounted into the retaining portion 55a while, in this case, pushing up the rotary plate body 55b. As shown in FIG. 37, when the slider 46 is completely mounted to the retaining portion 55a, the rotary plate body 55b that is pushed up causes the limit button 55d of the limit switch 55c to sink so that the limit switch 55c is turned ON.

An activation state that is an operable state where the operation instruction portion 33 of the controller 30 is enabled is realized only when the limit switch 55c is turned ON. In other words, when the slider 46 of the treatment instrument 40 is mounted to the retaining portion 55a, operations of the treatment instrument electrical operation apparatus 50 and the treatment instrument electrical advance/retreat apparatus 60 by the controller 30 are enabled, and when the slider 46 of the treatment instrument 40 is not mounted to the retaining portion 55a, operations of the treatment instrument electrical operation apparatus 50 and the treatment instrument electrical advance/retreat apparatus 60 by the controller 30 are disabled.

According to such a configuration, even when the operation lever 34 of the operation instruction portion 33 of the controller 30 is tilt-operated when replacing the treatment instrument 40, operations of the treatment instrument electrical operation apparatus 50 and the treatment instrument electrical advance/retreat apparatus 60 are disabled unless the slider 46 of the treatment instrument 40 is securely mounted to the retaining portion 55a. As a result, the treatment instrument electrical operation apparatus 50 and the treatment instrument electrical advance/retreat apparatus 60 are not driven even in cases of attachment deviation of the slider 46 and inadvertent, erroneous operations when replacing the treatment instrument 40. Consequently, the configuration of the present reference example achieves effects similar to the respective reference examples.

Fifth Reference Example

Figure 38:
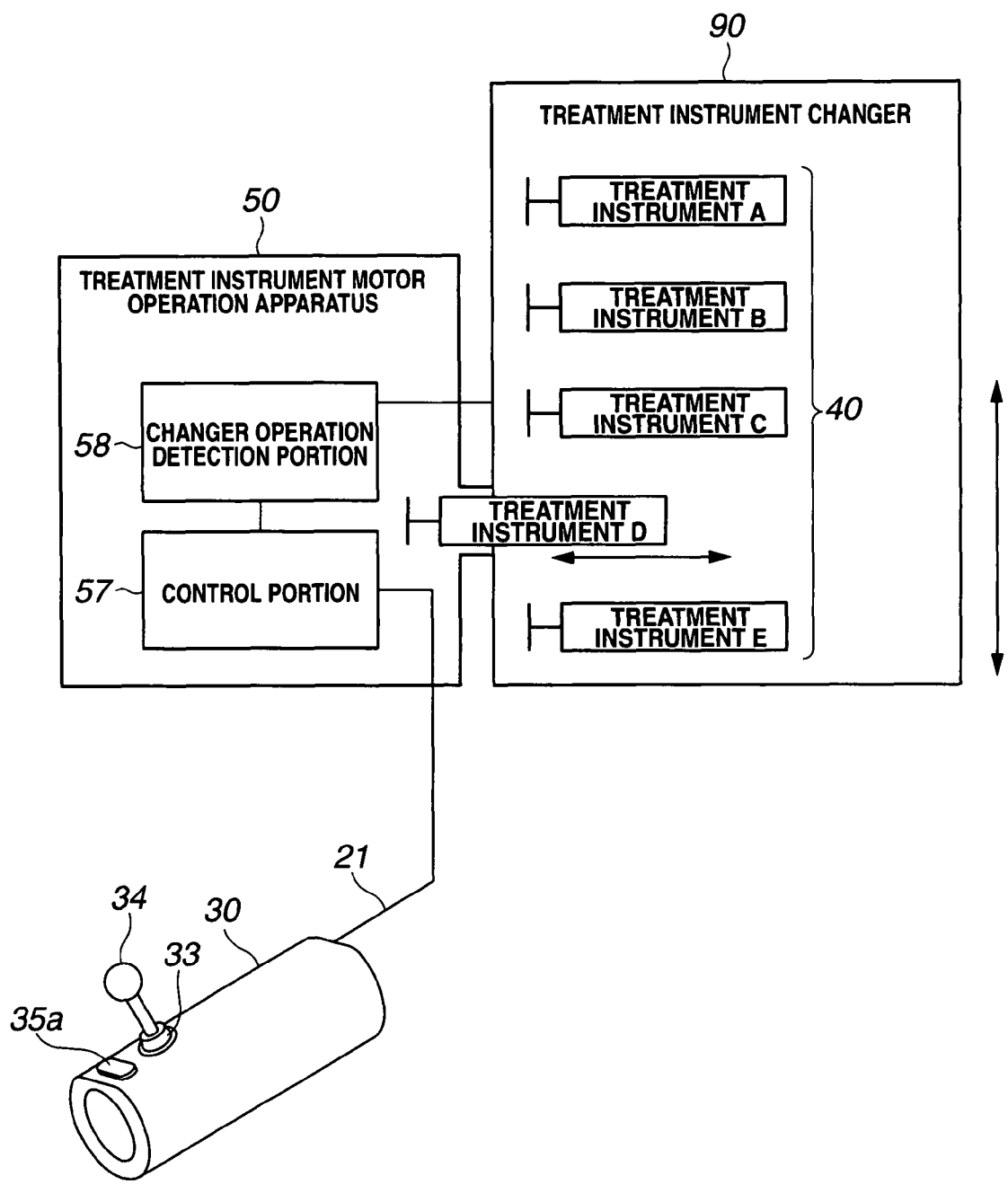
FIG. 38 is a configuration diagram showing a controller, a treatment instrument electrical operation apparatus and a treatment instrument changer according to a fifth reference example.

Next, a fifth reference example will be described. FIG. 38 is a configuration diagram showing a controller, a treatment instrument electrical operation apparatus and a treatment instrument changer according to the fifth reference example.

For the present reference example, a description is provided on a treatment instrument changer 90 that is an automatic changer capable of automatically changing a plurality of various treatment instruments (A to E) 40 for the treatment instrument electrical operation apparatus 50 by means of a treatment instrument changing-over switch 35a provided on the controller 30.

In addition, a control portion 57 that is electrically connected to the controller 30, and a changer operation detection portion 58 are built into the treatment instrument electrical operation apparatus 50. Furthermore, the treatment instrument changer 90 has, for instance, an array of various treatment instruments (A to E) 40 respectively having different treatment functions, and changes, while sliding, the treatment instruments (A to E) 40 that are selected by the treatment instrument electrical operation apparatus 50 so as to be operable.

Additionally, the changer operation detection portion 58 detects changing operations of the treatment instruments (A to E) 40 by the treatment instrument changer 90 or, in other words, whether the treatment instrument changer 90 is driven or stopped.

To elaborate, when the various treatment instruments (A to E) 40 are being changed and the treatment instrument changer 90 is being driven, the changer operation detection portion 58 outputs a changer ON signal to the control portion 57. In response, the control portion 57 disables the treatment instrument changing-over switch 35a of the controller 30.

On the other hand, when the various treatment instruments (A to E) 40 are not being changed and the treatment instrument changer 90 is stopped, the changer operation detection portion 58 outputs a changer OFF signal to the control portion 57. In response, the control portion 57 enables the treatment instrument changing-over switch 35a of the controller 30.

Accordingly, even when the treatment instrument changing-over switch 35a of the controller 30 is erroneously turned ON during driving of the treatment instrument changer 90, the treatment instrument electrical operation apparatus 50 slides an originally selected treatment instrument 40 to an operable condition, and the treatment instrument 40 is set to a predetermined position in the treatment instrument electrical operation apparatus 50. In other words, even when the treatment instrument changing-over switch 35a of the controller 30 is inadvertently operated, the slide movement of the treatment instrument changer 90 is regulated until the originally selected treatment instrument 40 is set to the treatment instrument electrical operation apparatus 50.

As a result, the selected treatment instrument 40 is securely set in the treatment instrument electrical operation apparatus 50, and damages to the treatment instrument 40 due to inadvertent slide movement of the treatment instrument changer 90 may be prevented.

Moreover, two functions for activating the treatment instrument changer 90 and changing the entire controller 30 to a drive-disabled state through operations of the treatment instrument changing-over switch 35a of the controller 30 may be provided. As a result, detection by the changer operation detection portion 58 may be simplified.

Furthermore, after the treatment instrument changing-over switch 35a of the controller 30 is turned ON, the controller 30 may be changed to a stopped state where the functions of the controller 30 are disabled for a period of time sufficient for the treatment instrument 40 to be securely set by the treatment instrument changer 90 to the treatment instrument electrical operation apparatus 50, and after the lapse of the controller non-active time, the controller 30 may automatically be restored to a driven state where the functions of the controller are enabled. As a result, the changer operation detection portion 58 is no longer required and a simple configuration is realized.

The invention described above is not limited to the respective embodiments, and various modifications may be achieved in the implementation phase of the invention without departing from the scope of the invention. In addition, each embodiment includes inventions of various stages, and various inventions may be extracted according to appropriate combinations of a plurality of disclosed constituent features.

For example, even when several constituent features are deleted from all constituent features shown in the respective embodiments, in the event that advantageous effects described in relevant sections herein may be achieved with respect to problems to be solved by the invention, a configuration from which such constituent features are deleted may be extracted as an invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical system comprising:
a treatment instrument configured to be inserted into a channel of an insertion portion of an endoscope, the treatment instrument including at a distal end thereof a treatment portion for performing treatment operations on living body tissue;
a treatment instrument advance/retreat apparatus configured to advance and retreat the treatment instrument in accordance with a user input such that the treatment instrument moves at a first speed in the channel or at a second speed that is lower than the first speed outside the channel by switching an advance/retreat speed without stopping advancement/retreat of the treatment instrument;
a detection portion configured to detect whether the treatment portion of the treatment instrument is led out and positioned distally from a distal end of the insertion portion of the endoscope; and
a control portion configured to control the treatment instrument advance/retreat apparatus to vary an advance/retreat speed of the treatment instrument according to detection results from the detection portion, wherein the control portion is configured:
in a state where the detection portion detects that the treatment portion is not led out distally from the distal end of the insertion portion and positioned in the channel, to control the treatment instrument advance/retreat apparatus to advance/retreat the treatment instrument at the first speed, and
in a state where the detection portion detects that the treatment portion is led out and positioned distally from the distal end of the insertion portion, to control the treatment instrument advance/retreat apparatus to advance/retreat the treatment instrument at the second speed that is lower than the first speed by switching the advance/retreat speed without stopping advancement/retreat of the treatment instrument.

2. The medical system according to claim 1, wherein the medical instrument is a high-frequency treatment instrument that performs treatment operations using high frequency applied to the treatment portion, and the treatment detection portion detects a treatment state or a non-treatment state based on the high-frequency energization state to the treatment portion.

3. The medical system according to claim 1, wherein the medical instrument is a rotating treatment instrument that performs treatment operations by the rotation of the treatment portion, and the treatment detection portion detects a treatment state or a non-treatment state based on the rotating state of the treatment portion.

4. The medical system according to claim 1, wherein based on the detection result of the treatment detection portion, the control portion stops the treatment portion displacement mechanism so that the mode changes to a stop mode in which the advance/retreat of the treatment portion is stopped.

5. The medical system according to claim 1, wherein based on the detection result of the treatment detection portion, the control portion drives the treatment portion displacement mechanism so that the advance/retreat displacement of the treatment portion is regulated based on a preset specified displacement value of the treatment portion.

6. The medical system according to claim 1 further comprising
a treatment storage portion that stores the state where the treatment portion is introduced into or led out from the distal end of the insertion portion.

7. The medical system according to claim 1, further comprising
an operation instruction portion that outputs an instruction signal that advances/retreats the treatment portion to the control portion, wherein
the control portion drives the treatment portion displacement mechanism at a high-speed mode that increases to a predetermined speed in the retreating direction of the treatment portion based on detection results of the treatment detection portion and predetermined operations of the operation instruction portion.

8. The medical system according to claim 7, wherein the treatment detection portion detects a treatment state or a non-treatment state of the treatment portion based on a light modulation function executed by the endoscope.

9. The medical system according to claim 1, wherein the medical instrument is an endoscopic treatment instrument that is inserted into a channel disposed in an insertion portion of an endoscope, and the displacement mechanism is a bending portion disposed to the insertion portion of the endoscope.

10. The medical system according to claim 1, further comprising
a treatment portion operation apparatus that drives the treatment portion.

11. The medical system according to claim 1, wherein the detection portion comprises an optical sensor provided on a distal end portion of the endoscope, and which detects whether the treatment portion is introduced into or led out from the distal end portion.

12. The medical system according to claim 11, wherein the treatment portion comprises a reflector that reflects light from a light emitting portion of the optical sensor, and the reflector includes a reflecting surface set to a predetermined curvature so as to reflect the light toward a light receiving portion of the optical sensor.

13. The medical system according to claim 1, wherein the detection portion is provided on a section protruding from a distal end face of a distal end portion of the insertion portion.

* * * * *